US011602528B2

(12) United States Patent
Mugrage et al.

(10) Patent No.: US 11,602,528 B2
(45) Date of Patent: *Mar. 14, 2023

(54) METHOD FOR THE TREATMENT OF POMPE DISEASE USING 1-DEOXYNOJIRIMYCIN DERIVATIVES

(71) Applicant: AMICUS THERAPEUTICS, INC., Cranbury, NJ (US)

(72) Inventors: Benjamin Mugrage, Cranbury, NJ (US); Gary Lee, West Windsor, NJ (US); Xiaoxiang Zhu, Cranbury, NJ (US); Robert Boyd, Horsham, PA (US); Kamlesh Sheth, North Brunswick, NJ (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 375 days.

This patent is subject to a terminal disclaimer.

(21) Appl. No.: 15/838,986

(22) Filed: Dec. 12, 2017

(65) Prior Publication Data

US 2018/0221357 A1     Aug. 9, 2018

Related U.S. Application Data

(63) Continuation of application No. 14/876,018, filed on Oct. 6, 2015, now abandoned, which is a continuation of application No. 11/440,473, filed on May 17, 2006, now Pat. No. 9,181,184.

(60) Provisional application No. 60/729,329, filed on Oct. 21, 2005, provisional application No. 60/682,241, filed on May 17, 2005.

(51) Int. Cl.
| | | |
|---|---|---|
| *A61K 31/44* | (2006.01) |
| *A61K 38/47* | (2006.01) |
| *A61P 3/00* | (2006.01) |
| *C07D 211/46* | (2006.01) |
| *C07D 405/06* | (2006.01) |
| *C07D 409/06* | (2006.01) |
| *A61K 31/445* | (2006.01) |
| *A61K 31/4525* | (2006.01) |
| *A61K 31/4545* | (2006.01) |

(52) U.S. Cl.
CPC ............ *A61K 31/44* (2013.01); *A61K 31/445* (2013.01); *A61K 31/4525* (2013.01); *A61K 31/4545* (2013.01); *A61K 38/47* (2013.01); *A61P 3/00* (2018.01); *C07D 211/46* (2013.01); *C07D 405/06* (2013.01); *C07D 409/06* (2013.01)

(58) Field of Classification Search
CPC ............ A61K 31/44; A61K 38/47; A61P 3/00
See application file for complete search history.

(56) References Cited

U.S. PATENT DOCUMENTS

| | | | |
|---|---|---|---|
| 4,837,237 | A | 6/1989 | Rohrschneider et al. |
| 4,985,445 | A | 1/1991 | Tsuruoka et al. |
| 5,011,829 | A | 4/1991 | Hirsch et al. |
| 5,103,008 | A | 4/1992 | Scudder et al. |
| 5,236,838 | A | 8/1993 | Rasmussen et al. |
| 5,399,567 | A | 3/1995 | Platt et al. |
| 5,472,969 | A | 12/1995 | Platt et al. |
| 5,580,757 | A | 12/1996 | Desnick et al. |
| 5,786,369 | A | 7/1998 | Platt et al. |
| 5,801,185 | A | 9/1998 | Platt et al. |
| 5,879,680 | A | 3/1999 | Ginns et al. |
| 6,083,725 | A | 7/2000 | Selden et al. |
| 6,118,045 | A | 9/2000 | Reuser et al. |
| 6,210,666 | B1 | 4/2001 | Miyamura |
| 6,225,325 | B1 | 5/2001 | Jacob |
| 6,274,597 | B1 | 8/2001 | Fan et al. |
| 6,395,884 | B1 | 5/2002 | Selden et al. |
| 6,451,600 | B1 | 9/2002 | Rasmussen et al. |
| 6,458,574 | B1 | 10/2002 | Selden et al. |
| 6,461,609 | B1 | 10/2002 | Calhoun et al. |
| 6,465,488 | B1 | 10/2002 | Butters et al. |
| 6,534,300 | B1 | 3/2003 | Canfield |
| 6,537,785 | B1 | 3/2003 | Canfield |
| 6,545,021 | B1 | 4/2003 | Mueller et al. |
| 6,583,158 | B1 | 6/2003 | Fan et al. |
| 6,589,964 | B2 | 7/2003 | Fan et al. |

(Continued)

FOREIGN PATENT DOCUMENTS

| | | |
|---|---|---|
| EP | 1137762 B1 | 10/2008 |
| EP | 2020438 A1 | 2/2009 |

(Continued)

OTHER PUBLICATIONS

Winkel et al., "Enzyme replacement therapy in late-onset Pompe's disease: a three-year follow-up," Ann. Neurol. Apr. 2004;55(4):495-502. PMID: 15048888. (Year: 2004).*

(Continued)

*Primary Examiner* — Theodore R. Howell
(74) *Attorney, Agent, or Firm* — Servilla Whitney LLC

(57) ABSTRACT

The present invention provides a method for increasing the activity of a mutant or wild-type α-glucosidase enzyme in vitro and in vivo by contacting the enzyme with a specific pharmacological chaperone which is a derivative of 1-deoxynojirimycin. The invention also provides a method for the treatment of Pompe disease by administration of chaperone small molecule compound which is a derivative of 1-deoxynojirimycin. The 1-deoxynojirimycin derivative is substituted at the N or C1 position. Combination therapy with replacement α-glucosidase gene or enzyme is also provided.

10 Claims, 9 Drawing Sheets
Specification includes a Sequence Listing.

(56) References Cited

U.S. PATENT DOCUMENTS

| | | |
|---|---|---|
| 6,599,919 B2 | 7/2003 | Fan et al. |
| 6,696,059 B2 | 2/2004 | Jacob et al. |
| 6,916,829 B2 | 7/2005 | Fan et al. |
| 7,141,582 B2 | 11/2006 | Fan et al. |
| 7,351,410 B2 | 4/2008 | van Bree et al. |
| 7,371,366 B2 | 5/2008 | Canfield |
| 7,396,811 B2 | 7/2008 | LeBowitz et al. |
| 7,560,424 B2 | 7/2009 | LeBowitz et al. |
| 7,655,226 B2 | 2/2010 | Van Bree et al. |
| 7,658,916 B2 | 2/2010 | Zhu et al. |
| 7,785,856 B2 | 8/2010 | LeBowitz et al. |
| 7,858,576 B2 | 12/2010 | LeBowitz et al. |
| 7,910,545 B2 | 3/2011 | Meeker et al. |
| 7,981,864 B2 | 7/2011 | LeBowitz |
| 8,940,766 B2 | 1/2015 | Boyd et al. |
| 9,181,184 B2 | 11/2015 | Mugrage et al. |
| 2002/0049233 A1 | 4/2002 | Kararli et al. |
| 2002/0095135 A1 | 7/2002 | Meeker et al. |
| 2004/0180419 A1 | 9/2004 | Fan |
| 2004/0204379 A1 | 10/2004 | Cheng et al. |
| 2005/0244400 A1 | 11/2005 | LeBowitz et al. |
| 2006/0121018 A1 | 6/2006 | LeBowitz |
| 2007/0178081 A1 | 8/2007 | Fan |
| 2009/0117091 A1 | 5/2009 | LeBowitz et al. |
| 2009/0203575 A1 | 8/2009 | LeBowitz et al. |
| 2010/0119502 A1 | 5/2010 | Do et al. |
| 2010/0260740 A1 | 10/2010 | Boyd et al. |
| 2011/0136151 A1 | 6/2011 | Wustman et al. |

FOREIGN PATENT DOCUMENTS

| | | |
|---|---|---|
| FR | 2861991 | 5/2005 |
| WO | WO-2000/034451 A1 | 6/2000 |
| WO | WO-2001/019955 A2 | 3/2001 |
| WO | WO 01/97829 | 12/2001 |
| WO | WO-2004/069190 A2 | 8/2004 |
| WO | WO-2005/077093 A2 | 8/2005 |
| WO | WO-2006/125141 A2 | 11/2006 |
| WO | WO-2008/112525 A2 | 9/2008 |
| WO | WO-2009/066069 A1 | 5/2009 |
| WO | WO-2010/015816 A2 | 2/2010 |
| WO | WO-2010148253 A2 | 12/2010 |

OTHER PUBLICATIONS

Anthropometric Reference Data for Children and Adults: United States 2007-2010, *Vital and Health Statistics, Series 11, No. 252, U.S. Department of Health and Human Services, Center for Disease Control*, Oct. 2012, 48 pages.

Asano et al., Nitrogen-in-the-ring pyranoses and furanoses: structural basis of inhibition of mammalian glycosidases. J. Med. Chem. 1994; 37:3701-06.

Banati et al., Enzyme replacement therapy induces T-cell responses in late-onset Pompe disease. Muscle Nerve. Nov. 2011; 44(5):720-6.

Barton et al., Replacement Therapy for Inherited Enzyme Deficiency—Macrophage-Targeted Glucocerebrosidase for Gaucher's Disease, N. Eng. J. Med. 1991; 324:1464-1470.

Butters, et al. Imino Sugar Inhibitors for Treating the lysosomal Glycosphingolipidoses, Glycobiology, 2005; 15(10):43E-52R.

Courageot et al., α-Glucosidase inhibitors reduce dengue virus production by affecting the initial steps of virion morphogenesis in the endoplasmic reticulum, Journal of Virology, 2000, 74:564-572.

Cox et al., Novel oral treatment of Gaucher's disease with N-butyldeoxynojirimycin (OGT 918) to decrease substrate biosynthesis, The Lancet, 2000; 355:1481-1485.

Dale et al., Reversible inhibitors of beta-glucosidase. Biochemistry 1985; 24:3530-39.

Duke University, *Duke Obtains FDA Designation for Pompe Disease Therapy*, press release dated Sep. 2, 1997, 2 pages.

Final Office Action in U.S. Appl. No. 11/440,473, dated May 19, 2010, 7 pages.

Final Office Action in U.S. Appl. No. 11/440,473, dated May 15, 2009, 8 pages.

Final Office Action in U.S. Appl. No. 11/440,473, dated May 9, 2011, 8 pages.

Final Office Action in U.S. Appl. No. 11/440,473, dated Jan. 5, 2015, 8 pages.

Genzyme Corporation. Myozyme®. Cambridge, MA: Genzyme Corporation, Jun. 2010.

Jeyakumar et al. Delayed symptom onset and increased life expectancy in Sandhoff disease mice treated with N-butyldeoxynojirimycin, Proc. Acad. Sci. USA, Medical Sciences, 1999; 96:6388-6393.

Khanna et al., The pharmacological chaperone AT2220 increases recombinant human acid α-glucosidase uptake and glycogen reduction in a mouse model of Pompe disease. PLoS ONE (2012) 7(7):e40776.

Kishnani et al., Duvoglustat HCl Increases Systemic and Tissue Exposure of Active Acid α-Glucosidase in Pompe Patients Co-administered with Alglucosidase α. Molecular Therapy, 2017, 25(5): 1199-1208.

Klinge et al., Enzyme replacement therapy in classical infantile pompe disease: results of a ten-month follow-up study. Neuropediatrics. 2005; 36(1):6-11.

Legler et al., Synthesis of 5-amino-5-deoxy-D-galactopyranose and 1,5-dideoxy-1,5-imino-D-galactitol, and their inhibition of alpha- and beta-D-galactosidases. Carbohydrate Res. 1986; 155:119-29.

Lembcke et al., "Lysosomal storage of glycogen as a sequel of alpha-glucosidase inhibition by the absorbed deoxynojirimycin derivative emiglitate (BAYo1248). A drug-induced pattern of hepatic glycogen storage mimicking Pompe's disease (glycogenesis type II)", Res. Exp. Med., 1991, 191(6): 389-404.

Mellor, Howard R., et al., Cellular effects of deoxynojirimycin analogues; uptake, retention and inhibition of glycosphingolipid biosynthesis, Biochem J. 2004; 381:861-866.

National Institutes of Health Clinical Center. Patient Education: Giving a subcutaneous injection. Bethesda, MD: NIH Clinical Center, 2002.

Non-Final Office Action in U.S. Appl. No. 14/379,131, dated Sep. 15, 2015, 13 pages.

Non-Final Office Action in U.S. Appl. No. 11/440,473, dated Sep. 14, 2009, 6 pages.

Non-Final Office Action in U.S. Appl. No. 11/440,473, dated Dec. 5, 2008, 8 pages.

Non-Final Office Action in U.S. Appl. No. 11/440,473, dated May 7, 2008, 8 pages.

Non-Final Office Action in U.S. Appl. No. 11/440,473, dated Sep. 30, 2010, 8 pages.

Non-Final Office Action in U.S. Appl. No. 11/440,473, dated Mar. 28, 2014, 9 pages.

Overkleeft, Herman S. et al., "Generation of Specific Deoxynojirimycin-type Inhibitors of the Non-lysosomal Glucosylceramidase," The Journal of Biological Chemistry, 273(41):26522-26527 (1998).

Parenti, G., et al., Alpha-Glucosidase Enhancement in Fibroblasts from Patients with Pompe Disease, J. Inherit. Metab. Dis. 2005: 28:193.

PCT International Search Report in PCT/US2013/029660, dated May 8, 2013, 2 pages.

Platt, Francis M. et al., "N-Butyldeoxygalactonojirimycin Inhibits Glycolipid Biosynthesis but Does Not Affect N-Linked Oligosaccharide Processing," The Journal of Biological Chemistry, 269(43):27108-27114 (1994).

Platt, et al. Prevention of Lysosomal Storage in Tay-Sachs Mice Treated with N-butyldeoxynojirimycin, Science, 1997:276:428-431.

Porto et al. The Pharmacological Chaperone N-butyldeoxynojirimycin Enhances Enzyme Replacement Therapy in Pompe Disease Fibroblasts. Mol Ther. 2009;17(6):964-71.

Raben et al., Replacing acid alpha-glucosidase in Pompe disease: recombinant and transgenic enzymes are equipotent, but neither completely clears glycogen from type II muscle fibers. Mol Ther. 2005; 11(1):48-56.

Ruvinov et al., Monovalent Cations Partially Repair a Conformational Defect in a Mutant Tryptophan Synthase α2 β2 Complex (β-E109A); J. Biol. Chem. 1995; 270: 17333-38.

(56) References Cited

OTHER PUBLICATIONS

Van der Ploeg et al., Receptor-Mediated Uptake of Acid α-Glucosidase Corrects Lysosomal Glycogen Storage in Cultured Skeletal Muscle, Pediatric Research, 1988; 24(1):90-94.
Van Hove et al., "High-level production of recombinant human lysosomal acid α-glucosidase in Chinese hampster ovary cells which targets to heart muscle and corrects glycogen accumulation in fibroblasts from patients with Pompe disease," Proc. Natl. Acad. Sci., 1996; 93:65-70.
Van Hove et al., "Purification of recombinant human precursor acid α-glucosidase," 43(3) Biochem. Mol. Biol. Int. 1997: 43(3):613-23.
The extended European search report dated Jan. 27, 2021, issued in European Application No. 20177473.4, 11 pages.

\* cited by examiner

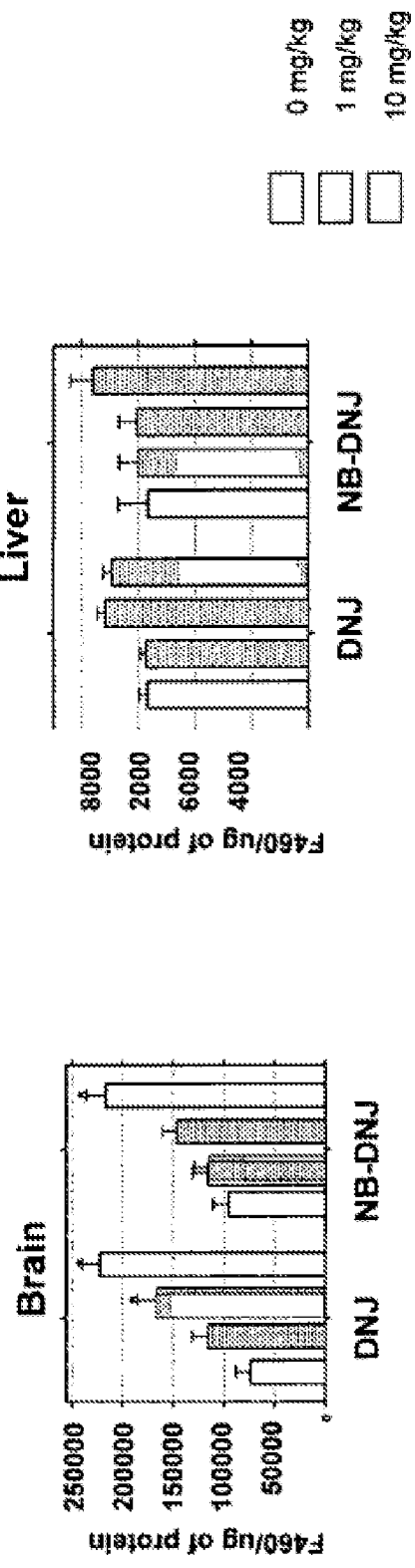
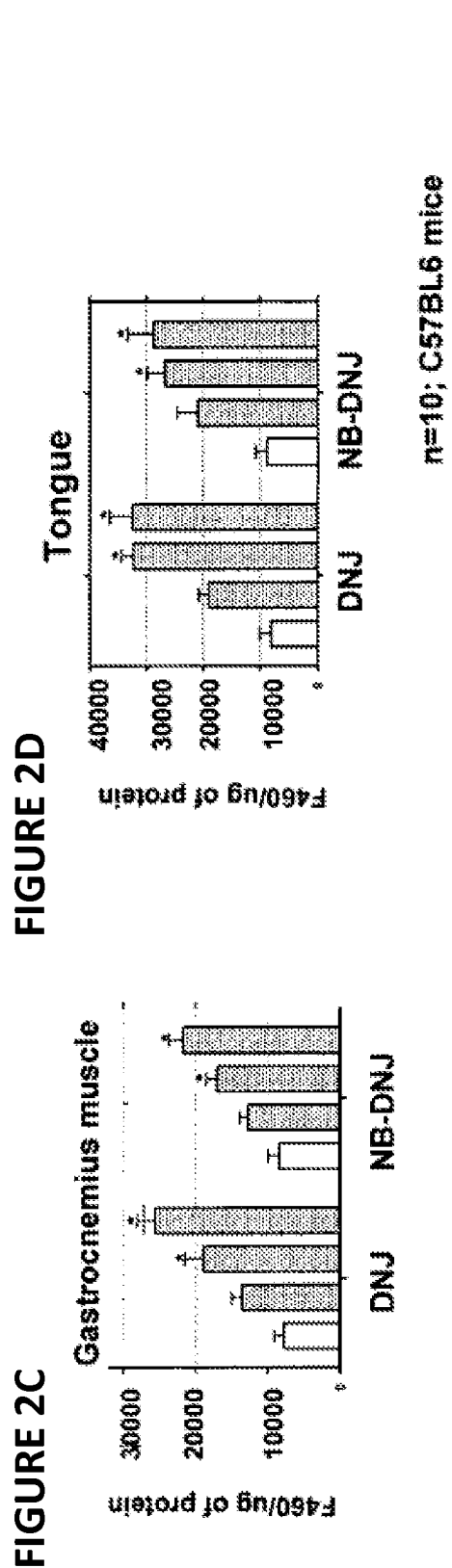

Comparison of 2 weeks treatment of AT2220 and AT2221 on GAA activity in vivo

Comparison of 4 weeks treatment of AT2220 and AT2221 on GAA activity in-vivo

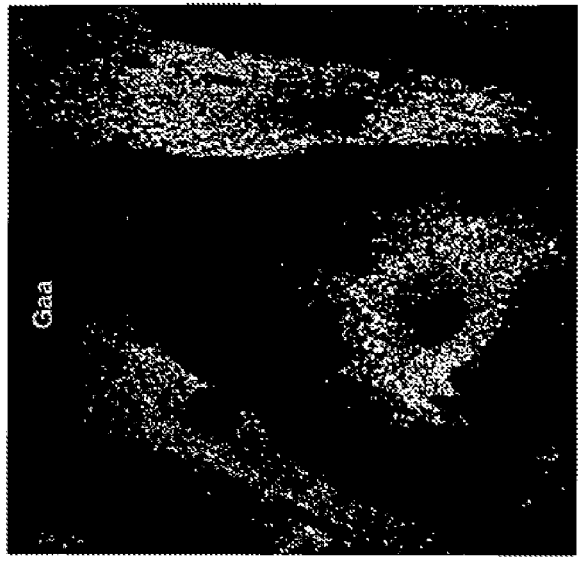
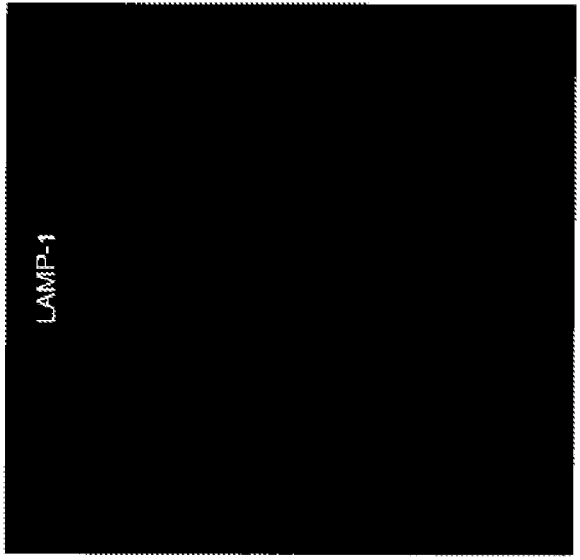
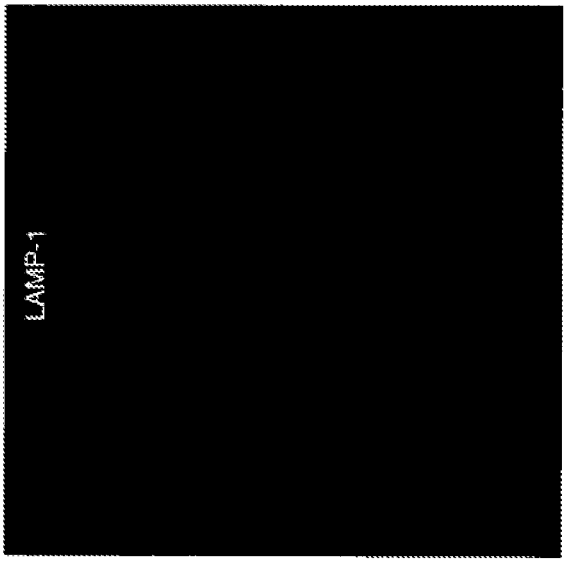
FIGURE 6A
PM8
(slicing defect)
FIGURE 6B
FIGURE 6C
WT
FIGURE 6D

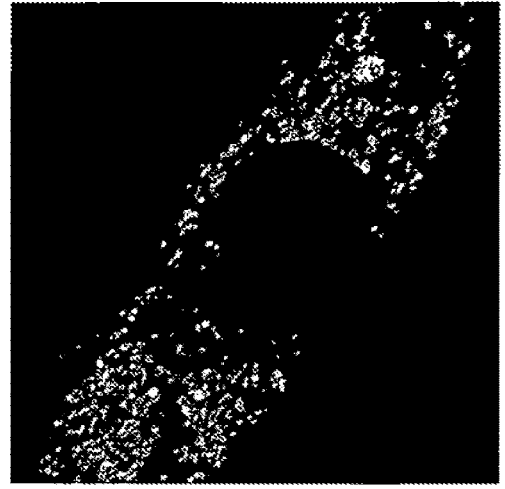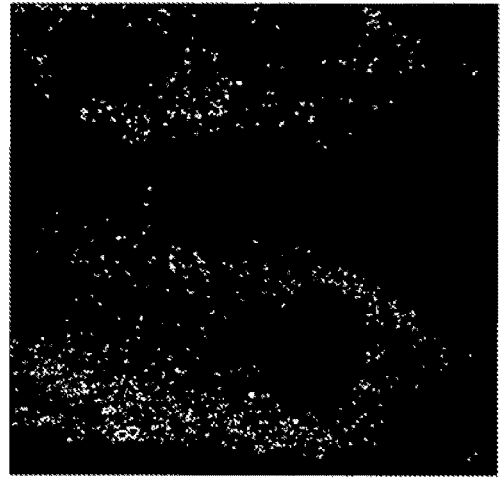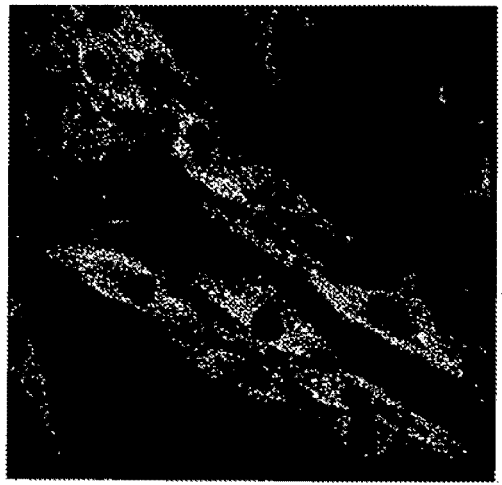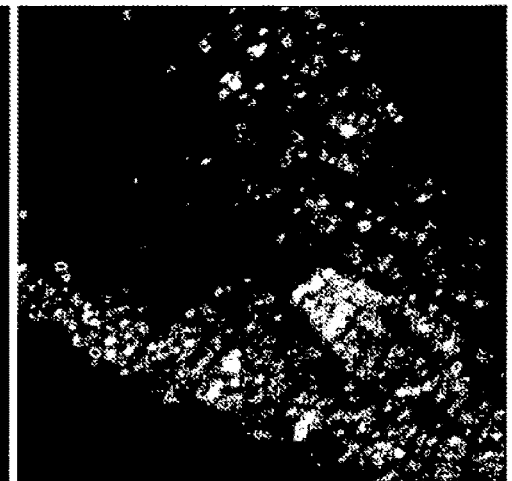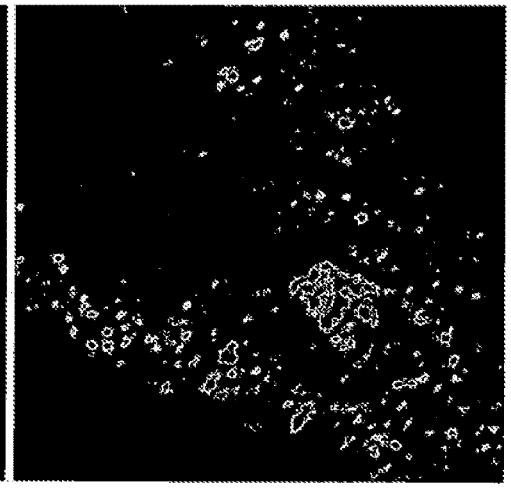

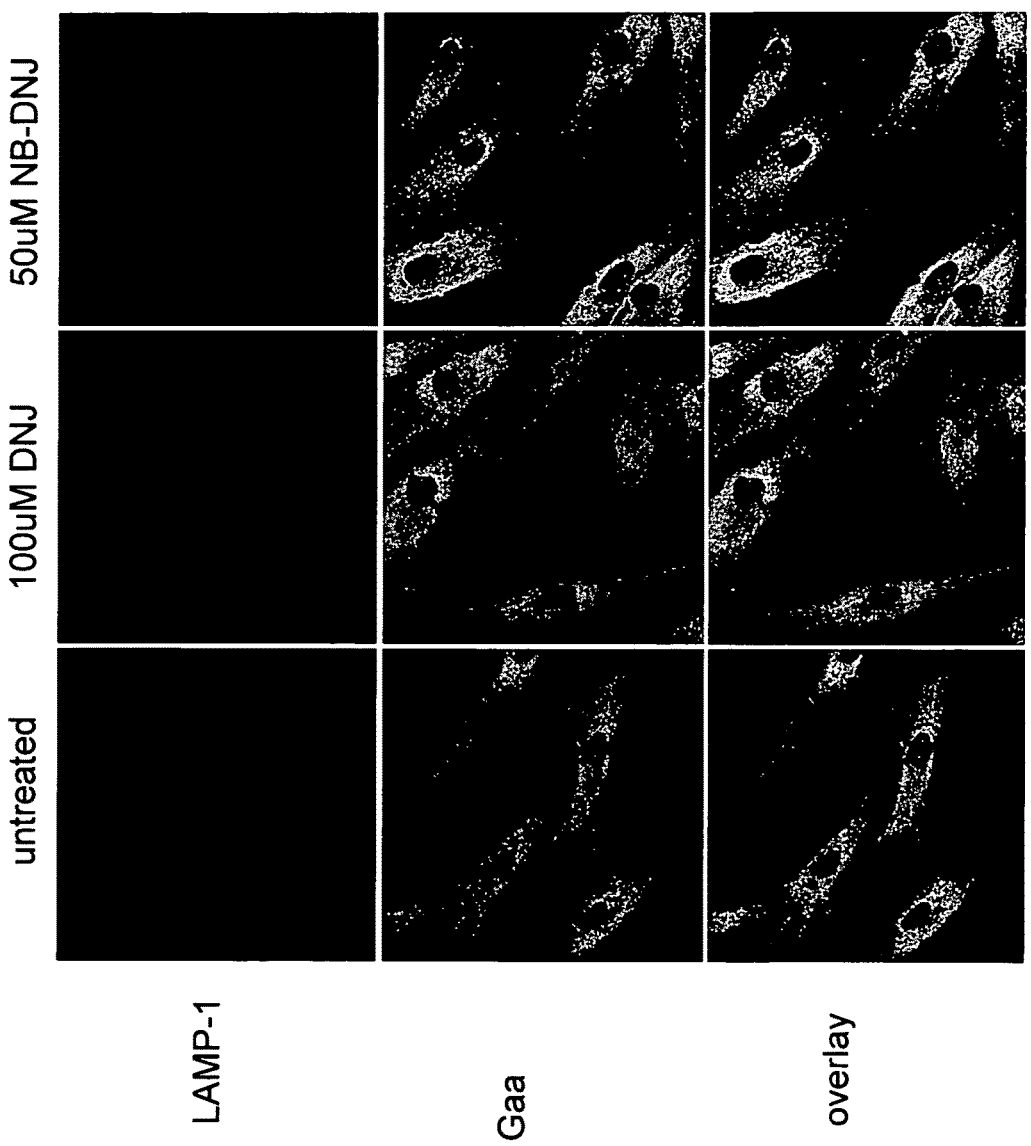

METHOD FOR THE TREATMENT OF POMPE DISEASE USING 1-DEOXYNOJIRIMYCIN DERIVATIVES

CROSS REFERENCE TO RELATED APPLICATIONS

This is a continuation of application Ser. No. 14/876,018, filed Oct. 6, 2015, which is a continuation of application Ser. No. 11/440,473, filed May 17, 2006, now U.S. Pat. No. 9,181,184, which claims the benefit of U.S. Provisional Application Nos. 60/682,241, filed May 17, 2005, and 60/729,329, filed Oct. 21, 2005, the entire disclosures of which are hereby incorporated by reference.

FIELD OF THE INVENTION

The present invention provides a method for increasing the activity of an α-glucosidase enzyme and a method for treating Pompe disease comprising administering to an individual an effective amount of 1-deoxynojirimycin (1-DNJ) and 1-DNJ derivatives, including for example, N-butyl-1-deoxynojirimycin (NB-DNJ). It has unexpectedly been shown that these compounds enhance acid α-glucosidase, the enzyme responsible for Pompe disease pathology.

BACKGROUND OF THE INVENTION

Pompe Disease

Pompe disease is one of several lysosomal storage disorders. Lysosomal storage disorders are a group of autosomal recessive diseases caused by the accumulation of cellular glycosphingolipids, glycogen, or mucopolysaccharides, due to defective hydrolytic enzymes. Examples of lysosomal disorders include but are not limited to Gaucher disease (Beutler et al., *The Metabolic and Molecular Bases of Inherited Disease,* 8th ed. 2001 Scriver et al., ed. pp. 3635-3668, McGraw-Hill, New York), $G_{M1}$-gangliosidosis (id. at pp 3775-3810), fucosidosis (*The Metabolic and Molecular Bases of Inherited Disease* 1995. Scriver, C. R., Beaudet, A. L., Sly, W. S. and Valle, D., ed pp. 2529-2561, McGraw-Hill, New York), mucopolysaccharidoses (id. at pp 3421-3452), Pompe disease (id. at pp. 3389-3420), Hurler-Scheie disease (Weismann et al., *Science.* 1970; 169, 72-74), Niemann-Pick A and B diseases, (*The Metabolic and Molecular Bases of Inherited Disease* 8th ed. 2001. Scriver et al. Ed., pp 3589-3610, McGraw-Hill, New York), and Fabry disease (Id. at pp. 3733-3774).

Pompe disease is caused by a deficiency in the enzyme acid α-glucosidase (Gaa). Gaa metabolizes glycogen, a storage form of sugar used for energy, into glucose. The accumulation of glycogen is thought to lead to progressive muscle myopathy throughout the body which affects various body tissues, particularly the heart, skeletal muscles, liver, and nervous system. According to the National Institute of Neurological Disorders and Stroke, Pompe disease is estimated to occur in about 1 in 40,000 births.

There are three recognized types of Pompe disease—infantile, juvenile, and adult onset. Infantile is the most severe, and presents with symptoms that include severe lack of muscle tone, weakness, enlarged liver and heart, and cardiomyopathy. Swallowing may become difficult and the tongue may protrude and become enlarged. Most children die from respiratory or cardiac complications before the age of two. Juvenile onset Pompe disease first presents in early to late childhood and includes progressive weakness of the respiratory muscles in the trunk, diaphragm, and lower limbs, as well as exercise intolerance. Most juvenile onset Pompe patients do not live beyond the second or third decade of life. Adult onset symptoms involve generalized muscle weakness and wasting of respiratory muscles in the trunk, lower limbs, and diaphragm. Some adult patients are devoid of major symptoms or motor limitations.

Current Treatment

Current treatment of Pompe disease involves symptomatic treatment of the cardiac and respiratory symptoms. There is no approved treatment for the underlying genetic defect. Recently, use of replacement Gaa (Myozyme; Genzyme, Inc.) was approved by the F.D.A. in the United States. However, clinical evaluations using enzyme replacement therapy to replace defective Gaa in infantile Pompe patients was only moderately successful in improving cardiac and skeletal function (Klinge et al., *Neuropediatrics.* 2005; 36(1): 6-11). Recombinant Gaa was shown to be more effective in resolving the cardiomyopathy than the skeletal muscle myopathy (Raben et al., *Mol Ther.* 2005; 11(1): 48-56), largely because recombinant enzyme cannot penetrate connective tissue. A method for treating Pompe disease using recombinant Gaa is specifically described in U.S. Pat. No. 6,537,785 to Canfield.

One of the main complications with enzyme replacement therapy (ERT) is the attainment and maintenance of therapeutically effective amounts of enzyme due to rapid degradation of the infused enzyme. As a result, ERT requires numerous, high-dose infusions and is costly and time consuming. ERT therapy has several additional caveats, such as difficulties with large-scale generation, purification and storage of properly folded protein, obtaining glycosylated native protein and the generation of an anti-protein immune response and failure of protein to cross the blood-brain barrier in sufficient quantities to affect diseases having significant central nervous system involvement. In addition, recombinant enzyme cannot cross barriers surrounding organs such as the kidney, nor can they penetrate connective tissue, and thus are not effective at restoring function to numerous affected tissues.

Gene therapy using recombinant vectors containing nucleic acid sequences that encode a functional protein, or genetically modified human cells that express a functional protein, is also being used to treat protein deficiencies and other disorders that benefit from protein replacement. Although promising, this approach is also limited by technical difficulties, such as the inability of vectors to infect or transduce dividing cells, low expression of the target gene, and regulation of expression once the gene is delivered (e.g., many viral vectors require cells to be dividing for efficacy).

A third, relatively recent approach to treating enzyme deficiencies involves the use of small molecule inhibitors to reduce the natural substrate of deficient enzyme proteins, thereby ameliorating the observed pathology. This "substrate deprivation" approach has been specifically described for treatment of some lysosomal storage disorders involving glycolipid accumulation (see U.S. Pat. Nos. 5,798,366, 6,291,657, and 6,660,749). The small molecule inhibitors proposed for use as therapy include N-alkyl-deoxynojirymycin (N-alkyl-DNJ) derivatives, and are reported to be specific for inhibiting the enzymes involved in synthesis of glycolipids, thereby reducing the amount of cellular glycolipid that needs to be broken down by the deficient enzyme. This approach is also limited in that glycolipids are necessary for biological function, and excess deprivation may cause adverse effects. Specifically, glycolipids are used by the brain to send signals from the gangliosides of one neuron to another. If there are too few or too many glycolipids, the ability of the neuron to send signals is impeded.

A fourth approach, a specific chaperone strategy, rescues mutated proteins from degradation presumably in the endoplasmic reticulum (ER) or in other cellular protein degradation/disposal systems. Previous patents and publications describe a therapeutic strategy for rescuing endogenous enzyme proteins, including misfolded lysosomal enzymes, from degradation by the ER quality control machinery. In particular embodiments, this strategy employs small molecule pharmcological chaperones which specifically bind to a defective lysosomal enzyme associated with a particular lysosomal disorder. In the absence of therapy, the mutated enzyme protein is unstable in the ER (Ishii et al., *Biochem. Biophys. Res. Comm.* 1996; 220: 812-815), is retarded in its maturation to a final product, and is subsequently degraded in the ER. The chaperone strategy involves the use of a compound that facilitates the folding and enhances the stability of a mutated protein, to prevent undue or abnormal degradation from the ER quality control system. These specific chaperones are designated as active site-specific chaperones or are also referred to as specific pharmacological chaperones.

The original theory behind this strategy is as follows: since the mutant enzyme protein folds improperly in the ER (Ishii et al., *Biochem. Biophys. Res. Comm.* 1996; 220: 812-815), the enzyme protein is retarded in the normal transport pathway (ER→Golgi apparatus→endosome→lysosome) and rapidly degraded. Therefore, a compound which facilitates the correct folding of a mutant protein will serve as an active site-specific chaperone for the mutant protein to promote its smooth escape from the ER quality control system. Some enzyme inhibitors were known to occupy the catalytic center, resulting in stabilization of enzyme conformation in vitro.

The specific pharmacological chaperone strategy has been demonstrated for numerous enzymes involved in lysosomal storage disorders as in U.S. Pat. Nos. 6,274,597, 6,583,158, 6,589,964, 6,599,919, and 6,916,829 to Fan et al., which are incorporated herein by reference in their entirety. For example, a small molecule derivative of galactose, 1-deoxygalactonojirimycin (DGJ), a potent competitive inhibitor of the mutant Fabry enzyme α-galactosidase A (α-Gal A; Gla), effectively increased in vitro stability of the human mutant α-Gal A (R301Q) at neutral pH, and it enhanced the mutant enzyme activity in lymphoblasts established from Fabry patients with R301Q or Q279E mutations. Furthermore, oral administration of DGJ to transgenic mice overexpressing a mutant (R301Q) α-Gal A substantially elevated the enzyme activity in major organs (Fan et al., *Nature Med.* 1999; 5: 112-115). Similar rescue of glucocerebrosidase (acid β-glucosidase, Gba) from Gaucher patient cells has been described using another iminosugar, isofagomine (IFG), and its derivatives, described in U.S. Pat. No. 6,916,829, and using other compounds specific for glucocerebrosidase (described in pending U.S. patent application Ser. No. 10/988,428, and U.S. patent application Ser. No. 10/988,427, both filed Nov. 12, 2004). U.S. Pat. No. 6,583,158, described above, discloses several small molecule compounds that would be expected to work in rescuing Gaa for the treatment of Pompe disease, including 1-deoxynojirimycin (DNJ), α-homonojirimycin, and castanospermine.

The present invention is based upon unexpected results obtained using DNJ derivatives, such as N-butyl DNJ, which were found to be effective specific pharmcological chaperones for mutant Gaa.

SUMMARY OF THE INVENTION

The present invention provides a method for inducing or stabilizing a proper conformation of an α-glucosidase (Gaa) enzyme in a cell by contacting the enzyme and a deoxynojirmicyin (DNJ) derivative, such as 1-dexoynorjirmicyin (1) or N-butyl DNJ (5). Preferably, the ratio of Gaa activity in the presence of the DNJ derivative over Gaa activity without the DNJ derivative is at least 1.5-fold at the concentration of the DNJ derivative that provides for the maximum Gaa activity. In another embodiment, the increase of Gaa activity is at least 5-fold.

In one embodiment, the DNJ derivative has the following structure:

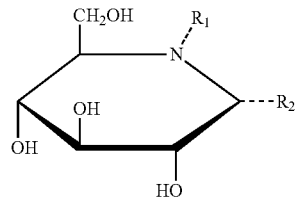

where $R_1$ is H or a straight or branched alkyl, cycloalkyl, alkenyl, alkoxyalkyl or aminoalkyl containing 1-12 carbon atoms, an aryl, alkylaryl, heteroaryl, or heteroaryl alkyl containing 5-12 ring atoms, where $R_1$ is optionally substituted with one or more —OH, —COOH, —Cl, —F, —CF$_3$, —OCF$_3$, —O—C(=O)N-(alkyl)$_2$;

$R_2$ is H; a straight or branched alkyl, cycloalkyl, alkenyl, alkylaryl, or alkoxyalkyl, containing 1-9 carbon atoms or aryl containing 5-12 carbon atoms, wherein $R_2$ is optionally substituted with —OH, —COOH, —CF$_3$, —OCF$_3$ or a heterocyclic ring; and at least one of $R_1$ and $R_2$ is not H; or a pharmaceutically acceptable salt thereof. Preferably the increase of Gaa activity in the presence of the DNJ derivative over Gaa activity without the DNJ derivative is at least 1.5 at the concentration of the DNJ derivative that provides for the maximum Gaa activity in a cell, with the proviso that the DNJ derivative is not 1-deoxynojirimycin or α-homonojirimycin.

In another embodiment, the DNJ derivative has the following structure:

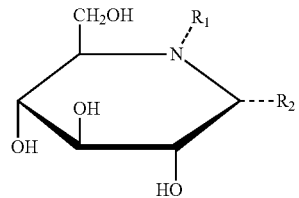

where $R_1$ is H or a straight or branched alkyl, cycloalkyl, alkoxyalkyl or aminoalkyl containing 1-12 carbon atoms optionally substituted with an —OH, —COOH, —Cl, —F, —CF$_3$, —OCF$_3$, —O—C(=O)N-(alkyl)$_2$;

$R_2$ is H or a straight or branched alkyl, cycloalkyl, or alkoxylalkyl containing 1-9 carbon atoms; and at least one of $R_1$ and $R_2$ is not H; or a pharmaceutically acceptable salt thereof. Preferably, the ratio of Gaa activity in the presence of the DNJ derivative over Gaa activity without the DNJ derivative is at least 1.5 at the concentration of the DNJ derivative that provides for the maximum Gaa activity in a cell, with the proviso that the DNJ derivative is not 1-deoxynojirimycin or α-homonojirimycin.

The maximum Gaa activity in a cell can be determined in vitro or in vivo as set forth in the examples, and for any DNJ derivative, one can use any of the exemplified assays to show this activity ratio.

In a specific embodiment, $R_1$ is a straight or branched alkyl, cycloalkyl, or alkoxyalkyl containing 1-9 carbon atoms optionally substituted with a —OH, —COOH, $CF_3$, $OCF_3$, or —C(=O)N—$(Me)_2$; and $R_2$ is H. In another embodiment, $R_1$ is n-methyl, n-ethyl, n-butyl, n-cyclopropyl methyl, or n-nonyl. In yet another embodiment, wherein $R_1$ is n-ethyl or n-butyl substituted with a —OH, —COOH, $CF_3$, $OCF_3$, or —C(=O)N—$(Me)_2$.

In one embodiment, $R_1$ is

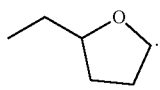

In another embodiment, $R_1$ is H and $R_2$ is a straight chain or branched alkyl, alkenyl, aryl or ether optionally substituted with —$CF_3$ or a heterocycle.

In one embodiment, $R_2$ is an n-nonyl group.

In further embodiments of the claimed method, the compound is selected from the group consisting of N-methyl-DNJ, N-butyl-DNJ, N-cyclopropylmethyl-DNJ, N-(2-(N,N-dimethylamido)ethyloxy-DNJ, N-4-t-butyloxycarbonyl-piperidnylmethyl-DNJ, N-2-R-tetrahydrofuranylmethyl-DNJ, N-2-R-tetrahydrofuranylmethyl-DNJ, N-(2-(2,2,2-trifluoroethoxy)ethyl-DNJ, N-2-methoxyethyl-DNJ, N-2-ethoxyethyl-DNJ, N-4-trifluoromethylbenzyl-DNJ, N-alpha-cyano-4-trifluoromethylbenzyl-DNJ, N-4-trifluoromethoxybenzyl-DNJ, N-4-n-pentoxybenzyl-DNJ, and N-4-n-butoxybenzyl-DNJ, or C1-nonyl DNJ.

In another embodiment, the compound increases lysosomal Gaa activity at a concentration at or below the $IC_{50}$ value for inhibition of intestinal Gaa.

In one embodiment, the Gaa enzyme is a mutant α-glucosidase. In specific embodiments, the mutant α-glucosidase is selected from the group consisting of D645E; D645H; R224W; S619R; R660H; T1064C; C2104T; D645N; L901Q; G219R; E262K; M408V; G309R; D645N; G448S; R672W; R672Q; P545L; C647W; G643R; M318T; E521K; W481R; L552P; G549R; R854X; V816I; and T927I and combinations thereof.

In another embodiment, the Gaa is a purified or recombinant functional Gaa.

In further embodiment, the contacting occurs in vivo or in vitro.

The invention also provides a method for the treatment of Pompe disease by administering an effective amount of a deoxynojirmicyin derivative, such as N-butyl DNJ.

In one embodiment, the DNJ derivative has the following structure:

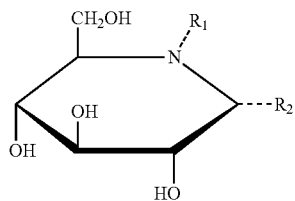

where $R_1$ is H or a straight or branched alkyl, cycloalkyl, alkenyl, alkoxyalkyl or aminoalkyl containing 1-12 carbon atoms, an aryl, alkylaryl, heteroaryl, or heteroaryl alkyl containing 5-12 ring atoms, where $R_1$ is optionally substituted with one or more —OH, —COOH, —Cl, —F, —$CF_3$, —$OCF_3$, —O—C(=O)N-$(alkyl)_2$;

$R_2$ is H; a straight or branched alkyl, cycloalkyl, alkenyl, or alkoxylalkyl, containing 1-9 carbon atoms or aryl containing 5-12 carbon atoms, wherein $R_2$ is optionally substituted with —OH, —COOH, —$CF_3$, —$OCF_3$ or a heterocyclic ring; and wherein at least one of $R_1$ and $R_2$ is not H; or a pharmaceutically acceptable salt thereof.

Preferably, the ratio of Gaa activity in the presence of the DNJ derivative over Gaa activity without the DNJ derivative is at least 1.5 at the concentration of the DNJ derivative that provides for the maximum Gaa activity in a cell, with the proviso that the DNJ derivative is not 1-deoxynojirimycin or α-homonojirimycin.

In another embodiment, the DNJ derivative has the following structure:

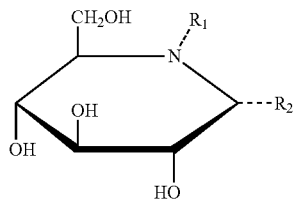

where $R_1$ is H a straight or branched alkyl, cycloalkyl, alkoxyalkyl or aminoalkyl containing 1-12 carbon atoms optionally substituted with an —OH, —COOH, —Cl, —F, —$CF_3$, —$OCF_3$, —O—C(=O)N-$(alkyl)_2$;

$R_2$ is H or a straight or branched alkyl, cycloalkyl, or alkoxylalkyl containing 1-9 carbon atoms; and at least one of $R_1$ and $R_2$ is not H; or a pharmaceutically acceptable salt thereof. Preferably, the ratio of Gaa activity in the presence of the DNJ derivative over Gaa activity without the DNJ derivative is at least 1.5 at the concentration of the DNJ derivative that provides for the maximum Gaa activity in a cell, with the proviso that the DNJ derivative is not 1-deoxynojirimycin or α-homonojirimycin.

In one embodiment, $R_1$ is a straight or branched alkyl, cycloalkyl, or alkoxyalkyl containing 1-9 carbon atoms optionally substituted with a —OH, —COOH, $CF_3$, $OCF_3$, or —C(=O)N—$(Me)_2$; and $R_2$ is H. In a specific embodiment, $R_1$ is n-methyl, n-ethyl, n-butyl, n-cylcopropyl methyl, or n-nonyl. In another embodiment, $R_1$ is n-ethyl or n-butyl substituted with a —OH, —COOH, $CF_3$, $OCF_3$, or —C(=O)N—$(Me)_2$. In yet another embodiment, $R_1$ is

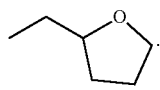

In another embodiment, $R_1$ is H, and $R_2$ is a straight chain or branched alkyl, alkenyl, aryl or ether optionally substituted with $CF_3$ or a heterocycle. In yet another embodiment, $R_2$ is an n-nonyl group.

In a particular embodiment, the compound is selected from the group consisting of N-methyl-DNJ, N-butyl-DNJ, N-cyclopropylmethyl-DNJ, N-(2-(N,N-dimethylamido)ethyloxy-DNJ, N-4-t-butyloxycarbonyl-piperidnylmethyl-DNJ, N-2-R-tetrahydrofuranylmethyl-DNJ, N-2-R-tetrahydrofuranylmethyl-DNJ, N-(2-(2,2,2-trifluoroethoxy)ethyl-DNJ, N-2-methoxyethyl-DNJ, N-2-ethoxyethyl-DNJ, N-4-trifluoromethylbenzyl-DNJ, N-alpha-cyano-4-trifluoromethylbenzyl-DNJ, N-4-trifluoromethoxybenzyl-DNJ, N-4-n-pentoxybenzyl-DNJ, and N-4-n-butoxybenzyl-DNJ, or C1-nonyl DNJ.

In another embodiment, the compound enhances lysosomal Gaa at a concentration at or below the $IC_{50}$ value for inhibition of intestinal Gaa.

In another embodiment, the effective amount of 1-deoxynojirmicyin derivative is from about 1 mg to 300 mg per day. In an alternative embodiment, the effective amount is from about 5 mg to about 150 mg per day. In still another embodiment, the effective amount is from about 5 to about 75 mg per day.

In one embodiment, the deoxynojirmicyin derivative is administered in an oral dosage form, such as a tablet or a capsule.

In another embodiment, the deoxynojirmicyin derivative is administered in combination with Gaa replacement enzyme.

In this embodiment, the deoxynojirmicyin derivative and Gaa replacement enzyme can be administered in separate formulations or as a single formulation.

For example, in one such embodiment, the deoxynojirmicyin derivative is administered in an oral dosage form and the Gaa replacement enzyme is administered in a parenteral dosage form.

In an alternative embodiment, the deoxynojirmicyin derivative is administered in combination with gene therapy.

In one embodiment of the invention, the above treatments result in an amelioration of Pompe disease pathology.

In a specific embodiment, the pathology is characterized by the presence of at least one of: decreased Gaa skeletal tissue activity; cardiomyopathy; cardiomegaly; progressive muscle weakness; hypotonia; macroglossia; difficulty swallowing, sucking, and/or feeding; respiratory insufficiency; hepatomegaly; laxity of facial muscles; areflexia; exercise intolerance; exertional dyspnea; orthopnea; sleep apnea; morning headaches; somnolence; lordosis and/or scoliosis; decreased deep tendon reflexes; lower back pain; and failure to meet developmental motor milestones.

The present invention also provides a method of relieving or reducing a symptom of Pompe disease by administering an effective amount of deoxynojirmicyin derivative.

In one embodiment, the symptom is at least on of: decreased Gaa skeletal tissue activity; cardiomyopathy; cardiomegaly; progressive muscle weakness; hypotonia; macroglossia; difficulty swallowing, sucking, and/or feeding; respiratory insufficiency; hepatomegaly; laxity of facial muscles; areflexia; exercise intolerance; exertional dyspnea; orthopnea; sleep apnea; morning headaches; somnolence; lordosis and/or scoliosis; decreased deep tendon reflexes; lower back pain; and failure to meet developmental motor milestones.

In alternative embodiments, the deoxynojirmicyin derivative is administered in combination with a replacement α-glucosidase protein or gene.

The present invention further includes DNJ derivatives, compositions comprising such DNJ derivatives, and pharmaceutical compositions comprising such DNJ derivatives. The DNJ Derivatives have structural formulas as set forth above, with the proviso that the DNJ derivative is not 1-deoxynojirimycin or α-homonojirimycin.

BRIEF DESCRIPTION OF THE DRAWINGS

FIG. 1 depicts the effects of 1-DNJ, NB-DNJ and N-(cyclopropyl)methyl DNJ iminosugar derivatives on the activity of acid α-glucosidase in the Pompe disease cell line PM-11.

FIGS. 2A-D. FIG. 2 shows Gaa enhancement in brain (2A), liver (2B), gastrocnemius (2C), and tongue (2D) of normal C57BL6 mice treated with various concentrations of DNJ and NB-DNJ for 2 weeks.

FIG. 3 shows Gaa enhancement in kidney (3A), diaphragm (3B), heart (3C), and soleus (3D) of normal C57BL6 mice treated with various concentrations of DNJ and NB-DNJ for 2 weeks.

FIG. 4 shows Gaa enhancement in brain (4A), liver (4B), gastrocnemius (4C), and tongue (4D) of normal C57BL6 mice treated with various concentrations of DNJ and NB-DNJ for 4 weeks.

FIG. 5 shows Gaa enhancement in kidney (5A), diaphragm (5B), heart (5C), and soleus (5D) of normal C57BL6 mice treated with various concentrations of DNJ and NB-DNJ for 4 weeks.

FIGS. 6A-H. FIG. 6 depicts Gaa immunostaining in wild-type (6C) and Pompe PM8 (6A and 6F) fibroblasts. This figure also depicts lysosomal staining for lysosomal marker LAMP-1 in wild-type (6D) and Pompe PM8 fibroblasts (6B and 6E). An overlay of Gaa and LAMP-1 staining for wild-type (6H) and PM8 (6G) fibroblasts is also shown.

FIGS. 7A-F. FIG. 7 depicts immunofluorescent staining for Gaa (7B and D) and LAMP-1 (7E) in PM9 Pompe fibroblasts. Overlays of Gaa and LAMP-1 staining are also depicted (7A, 7C and 7F).

FIG. 8. FIG. 8 depicts Gaa, LAMP-1, and Gaa/LAMP-1 dual staining PM11 Pompe cell lines that have been treated with DNJ or NB-DNJ.

DETAILED DESCRIPTION

Figure 1:
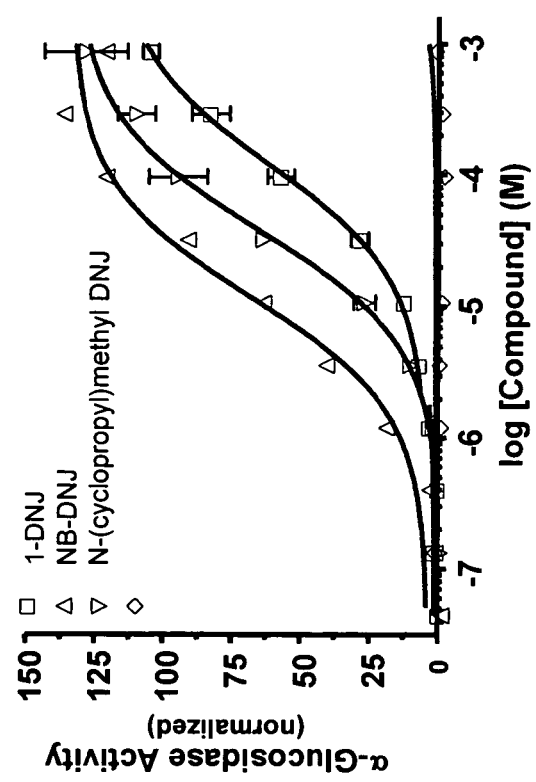
FIG. 1.
Figure 3A:
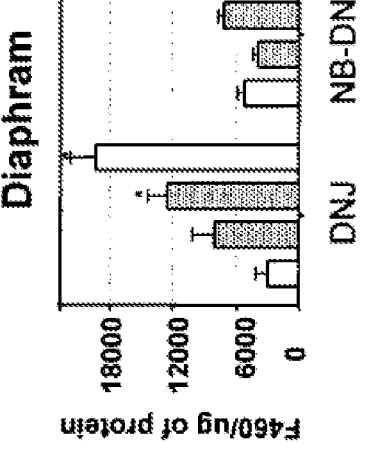
FIGS. 3A-D.
Figure 3B:
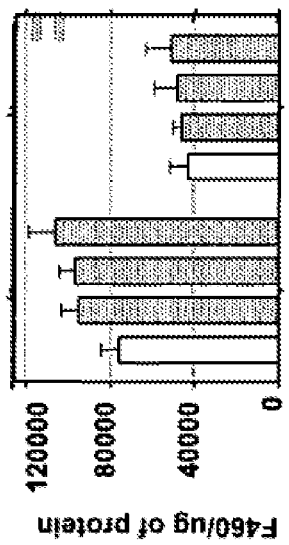
Figure 3C:
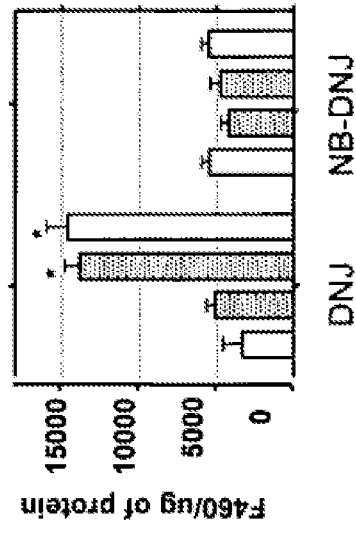
Figure 3D:
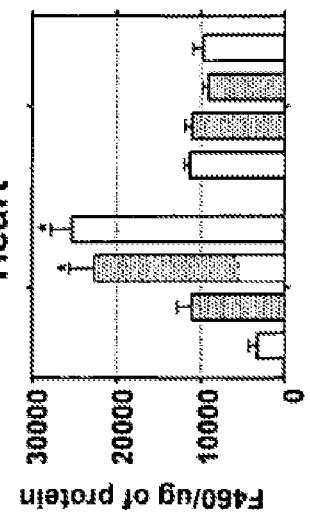
Figure 4A:
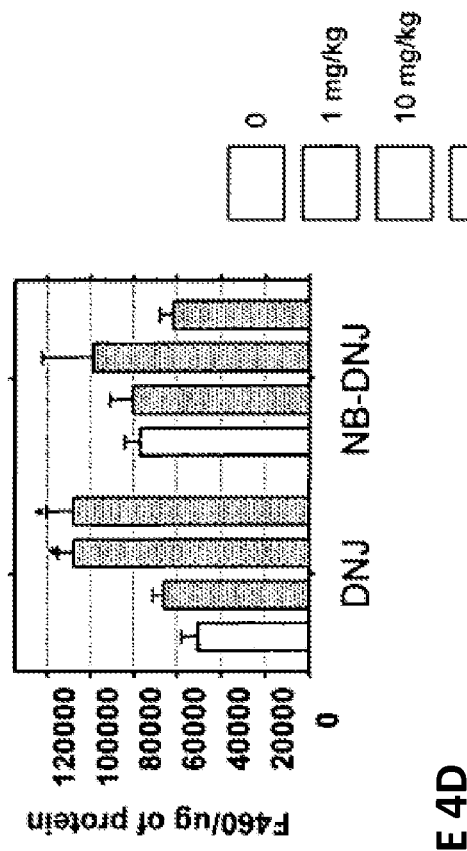
FIGS. 4A-D.
Figure 4B:
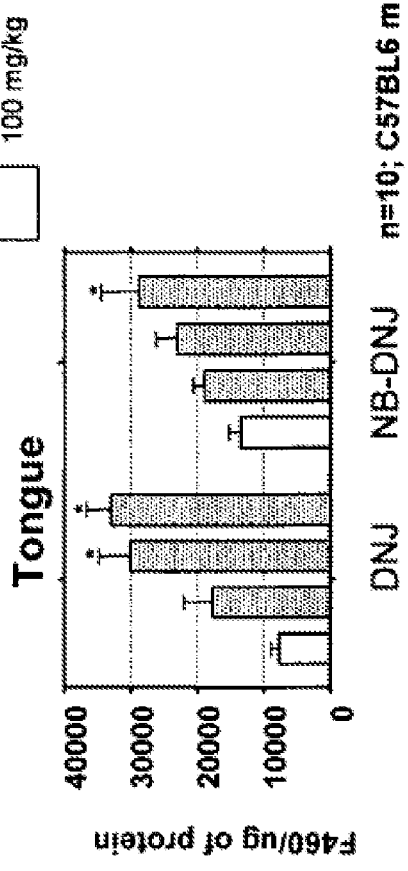
Figure 4C:
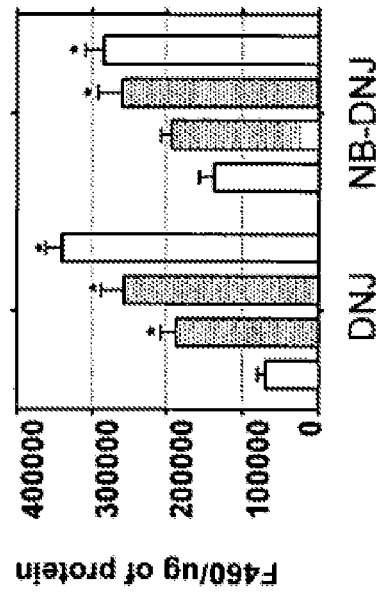
Figure 4D:
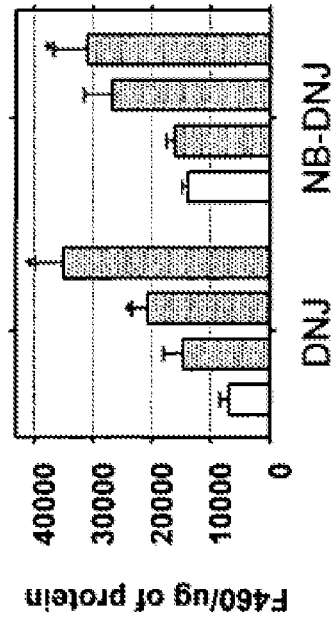
Figure 5A:
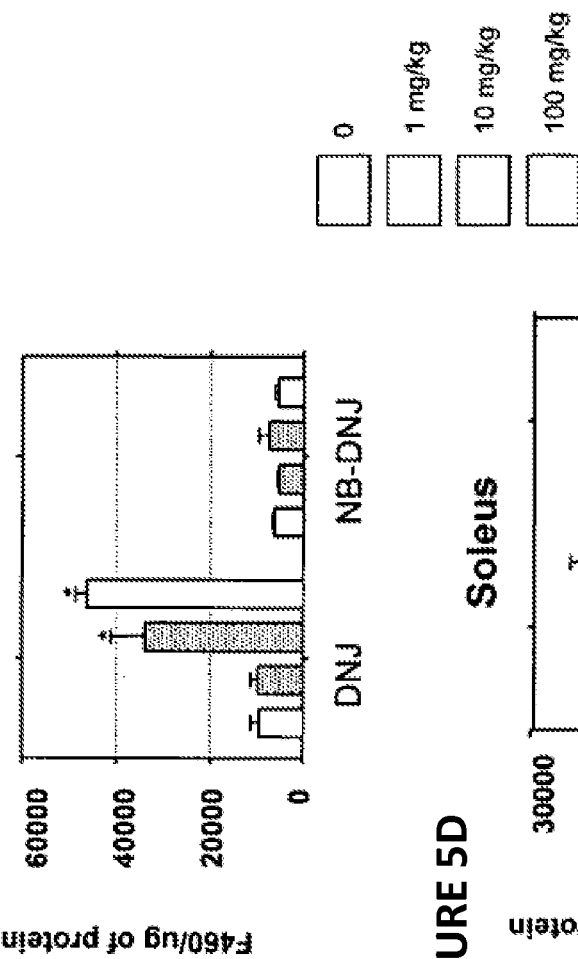
FIGS. 5A-D.
Figure 5B:
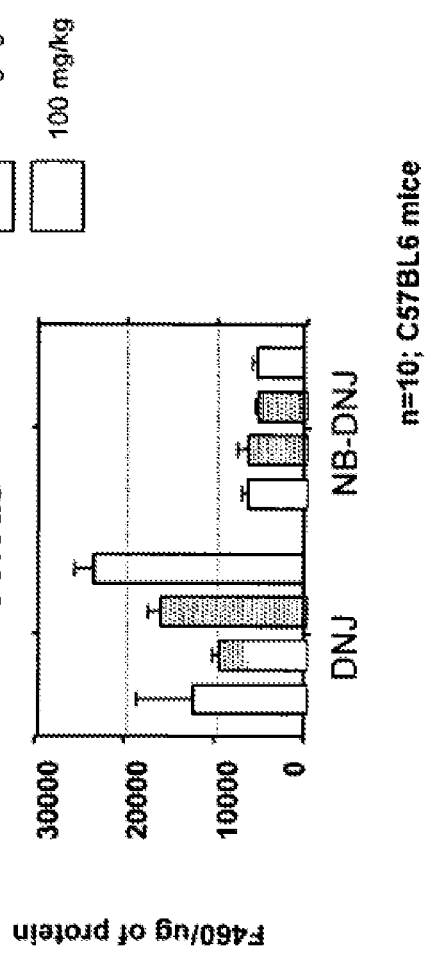
Figure 5C:
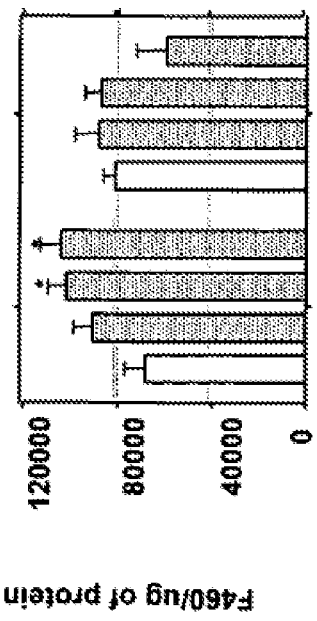
Figure 5D:
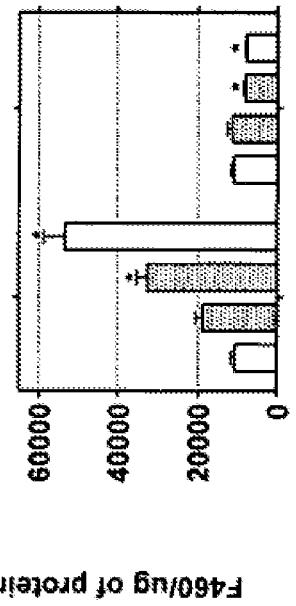

The present invention describes a method for the rescue of mutant Gaa, and the treatment of Pompe disease, using the small molecule imino sugar DNJ and derivatives of DNJ having substitutions at the ring nitrogen or ring carbon adjacent to the nitrogen as specific pharmacological chaperones. These molecules can bind to Gaa mutated proteins that are unstable and induce them to fold into a stable molecular conformation. As a result, Gaa progresses or trafficks to the lysosome and has hydrolytic activity against glycogen, thereby reducing the pathologic accumulation in muscle tissues associated with this disease.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

"Pompe disease," also referred to as acid maltase deficiency, glycogen storage disease type II (GSDII), and glycogenosis type II, is a genetic lysosomal storage disorder characterized by mutations in the Gaa gene which metabolizes glycogen. As used herein, this term includes infantile, juvenile and adult-onset types of the disease.

"Acid α-glucosidase (Gaa)" is a lysosomal enzyme which hydrolyzes alpha-1,4- and alpha-1,6-linked-D-glucose polymers present in glycogen, maltose, and isomaltose. Alternative names are as follows: glucoamylase; 1,4-α-D-glucan glucohydrolase; amyloglucosidase; gamma-amylase; and exo-1,4-α-glucosidase, and gamma-amylase. The human Gaa gene has been mapped to chromosome 17q25.2-25.3 and has nucleotide and amino acid sequences depicted in GenBank Accession No. Y00839 (depicted in SEQ ID NO: 1 and SEQ ID NO: 2, respectively). More than 70 mutations have been associated with Pompe disease. Mutations resulting in misfolding or misprocessing of the Gaa enzyme include T1064C (which changes Leu in position 355 into Pro) and C2104T (which substitutes Arg 702 into Cys) (Montalvo et al., *Mol Genet Metab.* 2004; 81(3): 203-8). In addition, Hermans et al. (*Human Mutation* 2004; 23: 47-56) describe a list of Gaa mutations which affect maturation and processing of the enzyme. Such mutations include Leu405Pro and Met519Thr. The method of the present invention is expected to be useful for mutations that cause unstable folding of α-glucosidase in the ER.

As used herein, the term "pharmacological chaperone," or sometimes "specific pharmacological chaperone" ("SPC"), refers to a molecule that specifically binds to Gaa and has one or more of the following effects: (i) enhancing the formation of a stable molecular conformation of the protein; (ii) enhances proper trafficking of the protein from the ER to another cellular location, preferably a native cellular location, i.e., preventing ER-associated degradation of the protein; (iii) preventing aggregation of conformationally unstable, i.e., misfolded proteins; (iv) restoring and/or enhancing at least partial wild-type function, stability, and/or activity of the protein; and/or (v) improving the phenotype or function of the cell harboring Gaa. Thus, a pharmacological chaperone for Gaa is a molecule that binds to Gaa, resulting in proper folding, trafficking, non-aggregation, and activity of Gaa. As used herein, this term does not refer to endogenous chaperones, such as BiP, or to non-specific agents which have demonstrated non-specific chaperone activity against various proteins, such as glycerol, DMSO or deuterated water, i.e., chemical chaperones (see Welch et al., *Cell Stress and Chaperones* 1996; 1(2):109-115; Welch et al., *Journal of Bioenergetics and Biomembranes* 1997; 29(5):491-502; U.S. Pat. Nos. 5,900,360; 6,270,954; and 6,541,195). It includes specific binding molecules, e.g., active site-specific chaperones (ASSCs), which bind in the active site of the enzyme, inhibitors or antagonists, and agonists.

As used herein, the term "specifically binds" refers to the interaction of a pharmacological chaperone with Gaa, specifically, an interaction with amino acid residues of Gaa that directly participate in contacting the pharmacological chaperone. A pharmacological chaperone specifically binds a target protein, e.g., Gaa, to exert a chaperone effect on Gaa and not a generic group of related or unrelated proteins. The amino acid residues of Gaa that interact with any given pharmacological chaperone may or may not be within the protein's "active site." As described infra, the conserved hexapeptide WiDMNE at amino acid residues 512-520 are required for activity of the Gaa protein (using SEQ ID NO:2 as a reference sequence). In addition, Trp516 and Asp518 are required for catalytic activity of Gaa (Hermans et al., *J. Biol. Chem.* 1991; 266: 13507-12). Specific binding can be evaluated through routine binding assays or through structural studies, e.g., co-crystallization, NMR, and the like.

In one non-limiting embodiment, the pharmacological chaperone is an inhibitor or antagonist of Gaa. In another non-limiting embodiment, the pharmacological chaperone is an agonist of Gaa. In yet another embodiment, the pharmacological chaperone is a mixed agonist/antagonist. As used herein, the term "antagonist" refers to any molecule that binds to a protein and either partially or completely blocks, inhibits, reduces, or neutralizes an activity of Gaa. The term "agonist" refers to any molecule that binds to a protein and at least partially increases, enhances, restores, or mimics an activity of Gaa. As discussed below, such molecules are known for Gaa.

As used herein, the terms "enhance Gaa conformational stability" or "increase Gaa conformational stability" refer to increasing the amount or proportion of Gaa that adopts a functional conformation in a cell contacted with a pharmacological chaperone specific for Gaa, relative to Gaa in a cell (preferably of the same cell-type or the same cell, e.g., at an earlier time) not contacted with the pharmacological chaperone specific for Gaa. In one embodiment, the cells do not express a conformation mutant Gaa. In another embodiment, the cells do express a mutant Gaa polynucleotide encoding a polypeptide e.g., a conformational mutant Gaa.

As used herein, the terms "enhance Gaa trafficking" or "increase Gaa trafficking" refer to increasing the efficiency of transport of Gaa to the lysosome in a cell contacted with a pharmacological chaperone specific for Gaa, relative to the efficiency of transport of Gaa in a cell (preferably of the same cell-type or the same cell, e.g., at an earlier time) not contacted with the pharmacological chaperone specific for Gaa.

As used herein, the terms "enhance Gaa activity" or "increase Gaa activity" refer to increasing the activity of Gaa, as described herein, in a cell contacted with a pharmacological chaperone specific for Gaa, relative to the activity of Gaa in a cell (preferably of the same cell-type or the same cell, e.g., at an earlier time) not contacted with the pharmacological chaperone specific for Gaa.

As used herein, the terms "enhance Gaa level" or "increase Gaa level" refer to increasing the level of Gaa in a cell contacted with a pharmacological chaperone specific for Gaa, relative to the level of Gaa in a cell (preferably of the same cell-type or the same cell, e.g., at an earlier time) not contacted with the pharmacological chaperone specific for Gaa.

The term "stabilize a proper conformation" refers to the ability of a Gaa pharmacological chaperone to induce or stabilize a conformation of a mutated Gaa protein that is functionally identical to the conformation of the wild-type Gaa protein. The term "functionally identical" means that while there may be minor variations in the conformation (almost all proteins exhibit some conformational flexibility in their physiological state), conformational flexibility does not result in (1) protein aggregation, (2) elimination through the endoplasmic reticulum-associated degradation pathway, (3) impairment of protein function, e.g., Gaa activity, and/or (4) improper transport within the cell, e.g., localization to the lysosome, to a greater or lesser degree than that of the wild-type protein.

The term "stable molecular conformation" refers to a conformation of a protein, i.e., Gaa, induced by a pharmacological chaperone, that provides at least partial wild-type function in the cell. For example, a stable molecular conformation of a mutant Gaa would be one where Gaa escapes from the ER and trafficks to the lysosome as for a wild-type Gaa, instead of misfolding and being degraded. In addition, a stable molecular conformation of a mutated Gaa may also possess full or partial Gaa activity, e.g., hydrolysis of α-1,4 and α-1,6 linkages in glycogen, maltose, and isomaltose. However, it is not necessary that the stable molecular conformation have all of the functional attributes of the wild-type protein.

The term "wild-type activity" refers to the normal physiological function of a Gaa in a cell. For example, Gaa activity includes folding and trafficking from the ER to the lysosome, with the concomitant ability to hydrolyze α-1,4- and α-1,6-linked-D-glucose polymers present in glycogen, maltose, and isomaltose.

The term "wild-type Gaa" refers to the nucleotide (SEQ ID NO. 1) sequences encoding Gaa, and polypeptide (SEQ ID NO: 2) sequences encoded by the aforementioned nucleotide sequences (human Gaa GenBank Accession No. Y00839, and any other nucleotide sequence that encodes Gaa polypeptide (having the same functional properties and binding affinities as the aforementioned polypeptide sequences), such as allelic variants in normal individuals, that have the ability to achieve a functional conformation in the ER, achieve proper localization within the cell, and exhibit wild-type activity (e.g., hydrolysis of glycogen).

As used herein the term "mutant α-glucosidase" or "mutant Gaa" refers to an α-glucosidase polypeptide translated from a gene containing a genetic mutation that results in an altered α-glucosidase amino acid sequence. In one embodiment, the mutation results in an α-glucosidase protein that does not achieve a native conformation under the conditions normally present in the ER, when compared with wild-type α-glucosidase or exhibits decreased stability or activity as compared with wild-type α-glucosidase. This type of mutation is referred to herein as a "conformational mutation," and the protein bearing such a mutation is referred as a "conformational mutant." The failure to achieve this conformation results in the α-glucosidase protein being degraded or aggregated, rather than being transported through a normal pathway in the protein transport system to its native location in the cell or into the extracellular environment. In some embodiments, a mutation may occur in a non-coding part of the gene encoding α-glucosidase that results in less efficient expression of the protein, e.g., a mutation that affects transcription efficiency, splicing efficiency, mRNA stability, and the like. By enhancing the level of expression of wild-type as well as conformational mutant variants of α-glucosidase, administration of an α-glucosidase pharmacological chaperone can ameliorate a deficit resulting from such inefficient protein expression. Alternatively, for splicing mutants or nonsense mutants which may accumulate in the ER, the ability of the chaperone to bind to and assist the mutants in exiting the ER, without restoring lysosomal hydrolase activity, may be sufficient to ameliorate some cellular pathologies in Pompe patients, thereby improving symptoms.

Exemplary conformational mutations of Gaa include the following: D645E (Lin et al., *Zhonghua Min Guo Xiao Er Ke Yi Xue Hui Za Zhi.* 1996; 37(2):115-21); D645H (Lin et al., *Biochem Biophys Res Commun.* 1995 17; 208(2):886-93); R224W, S619R, and R660H (New et al. *Pediatr Neurol.* 2003; 29(4):284-7); T1064C and C2104T (Montalvo et al., *Mol Genet Metab.* 2004; 81(3):203-8); D645N and L901Q (Kroos et al., *Neuromuscul Disord.* 2004; 14(6):371-4); G219R, E262K, M408V (Fernandez-Hojas et al., *Neuromuscul Disord.* 2002; 12(2):159-66); G309R (Kroos et al., *Clin Genet.* 1998; 53(5):379-82); D645N, G448S, R672W, and R672Q (Huie et al., *Biochem Biophys Res Commun.* 1998; 27; 244(3):921-7); P545L (Hermans et al., *Hum Mol Genet.* 1994; 3(12):2213-8); C647W (Huie et al., Huie et al., *Hum Mol Genet.* 1994; 3(7):1081-7); G643R (Hermans et al., *Hum Mutat.* 1993; 2(4):268-73); M318T (Zhong et al., *Am J Hum Genet.* 1991; 49(3):635-45); E521K (Hermans et al., *Biochem Biophys Res Commun.* 1991; 179(2):919-26); W481R (Raben et al., *Hum Mutat.* 1999; 13(1):83-4); and L552P and G549R (unpublished data).

Splicing mutants include IVSIAS, T>G, −13 and IVS8+1G>A).

Additional Gaa mutants have been identified and are known in the art. Conformational mutants are readily identifiable by one of ordinary skill in the art.

Mutations which impair folding, and hence, trafficking of Gaa, can be determined by routine assays well known in the art, such as pulse-chase metabolic labeling with and without glycosidase treatment to determine whether the protein enters the Golgi apparatus, or fluorescent immunostaining for Gaa localization within the cell. Wild-type Gaa is secreted as a 110 kD precursor which then converts to the mature Gaa of 76 kD via and intermediate of 95 kD.

Such functionality can be tested by any means known to establish functionality of such a protein. For example, assays using fluorescent substrates such as 4-α methylumbelliferyl-D-glucopyranoside can be used to determine Gaa activity. Such assays are well known in the art (see e.g., Hermans et al., above).

Certain tests may evaluate attributes of a protein that may or may not correspond to its actual in vivo activity, but nevertheless are appropriate surrogates of protein functionality, and wild-type behavior in such tests demonstrates evidence to support the protein folding rescue or enhancement techniques of the invention. One such activity in accordance with the invention is appropriate transport of a functional Gaa from the endoplasmic reticulum to the lysosome.

In vitro, e.g., in a formulation, the chaperone compound can also ensure that a wild-type or mutated protein can be maintained in its native or proper form. This effect may manifest itself practically through one or more of (i) increased shelf-life of the protein (i.e., for ERT); (ii) higher activity per unit/amount of protein; or (iii) greater in vivo efficacy. It may be observed experimentally through increased yield from the ER during expression; greater resistance to unfolding due to temperature increases, or the present of chaotropic agents, and by similar means.

The terms "endogenous expression" and "endogenously expressed" refers to the normal physiological expression of Gaa in cells in an individual not having or suspected of having a disease or disorder associated with Gaa deficiency, overexpression, or other defect, e.g., Pompe disease, such as a mutation in Gaa nucleic acid or polypeptide sequence that inhibit its expression, activity, or stability. This term also refers to the expression of Gaa in cell types in which it is normal for Gaa to be expressed and does not include expression in cells or cell types, e.g., tumors, in which Gaa is not expressed in healthy individuals.

As used herein, the term "efficiency of transport" refers to the ability of a mutant protein to be transported out of the endoplasmic reticulum to its native location within the cell, cell membrane, or into the extracellular environment.

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

Non-classical competitive inhibition occurs when the inhibitor binds remotely to the active site, creating a conformational change in the enzyme such that the substrate can no longer bind to it. In non-classical competitive inhibition, the binding of substrate at the active site prevents the binding of inhibitor at a separate site and vice versa. This includes allosteric inhibition.

A "linear mixed-type inhibitor" of an enzyme is a type of competitive inhibitor that allows the substrate to bind, but reduces its affinity, so the Km is increased and the Vmax is decreased.

A "non-competitive inhibitor" refers to a compound that forms strong bonds with an enzyme and may not be displaced by the addition of excess substrate, i.e., non-competitive inhibitors may be irreversible. A non-competitive inhibitor may bind at, near, or remote from the active site of an enzyme or protein, and in connection with enzymes, has no effect on the Km but decreases the Vmax. Uncompetitive inhibition refers to a situation in which inhibitor binds only to the enzyme-substrate (ES) complex. The enzyme becomes inactive when inhibitor binds. This differs from non-classical competitive inhibitors which can bind to the enzyme in the absence of substrate.

The term "Vmax" refers to the maximum initial velocity of an enzyme catalyzed reaction, i.e., at saturating substrate levels. The term "Km" is the substrate concentration required to achieve ½ Vmax.

An enzyme "enhancer" is a compound that binds to Gaa and increases the enzymatic reaction rate.

The terms "therapeutically effective dose" and "effective amount" refer to an amount sufficient to enhance protein processing in the ER (permitting a functional conformation), without inhibiting protein already expressed at the appropriate cellular location (in the case of an antagonist), or without inducing ligand-mediated receptor internalization of protein from the appropriate cellular location (in the case of an agonist), and enhance activity of the target protein, thus resulting in a therapeutic response in a subject. A therapeutic response may be any response that a user (e.g., a clinician) will recognize as an effective response to the therapy, including symptoms described herein and known in the art and any surrogate clinical markers. Thus, a therapeutic response will generally be an amelioration or inhibition of one or more symptoms of a disease or disorder, e.g., Pompe disease, such as those known in the art for the disease or disorder, e.g., decreased Gaa activity and progressive muscle weakness.

It should be noted that a concentration of the chaperone compound that is inhibitory during in vitro production, transportation, or storage of the purified therapeutic protein may still constitute an "effective amount" for purposes of this invention because of dilution (and consequent shift in binding due to the change in equilibrium), bioavailability and metabolism of the chaperone upon administration in vivo.

A "responder" is an individual diagnosed with Pompe disease and treated according to the presently claimed method who exhibits an improvement in, amelioration, or prevention of, one or more clinical symptoms, or improvement or reversal of one or more surrogate clinical markers that are indicators of disease pathology. Symptoms or markers of Pompe disease include but are not limited to decreased Gaa tissue activity; cardiomyopathy; cardiomegaly; progressive muscle weakness, especially in the trunk or lower limbs; profound hypotonia; macroglossia (and in some cases, protrusion of the tongue); difficulty swallowing, sucking, and/or feeding; respiratory insufficiency; hepatomegaly (moderate); laxity of facial muscles; areflexia; exercise intolerance; exertional dyspnea; orthopnea; sleep apnea; morning headaches; somnolence; lordosis and/or scoliosis; decreased deep tendon reflexes; lower back pain; and failure to meet developmental motor milestones.

The term "enzyme replacement therapy" or "ERT" refers to the introduction of a non-native, purified enzyme into an individual having a deficiency in such enzyme. The administered protein can be obtained from natural sources or by recombinant expression (as described in greater detail below). The term also refers to the introduction of a purified enzyme in an individual otherwise requiring or benefiting from administration of a purified enzyme, e.g., suffering from enzyme insufficiency. The introduced enzyme may be a purified, recombinant enzyme produced in vitro, or protein purified from isolated tissue or fluid, such as, e.g., placenta or animal milk, or from plants.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

The term "purified" as used herein refers to material, such as a Gaa nucleic acid or polypeptide, that has been isolated under conditions that reduce or eliminate unrelated materials, i.e., contaminants. For example, a purified protein is preferably substantially free of other proteins or nucleic acids with which it is associated in a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by conventional means, e.g., chromatography, gel electrophoresis, immunoassay, composition analysis, biological assay, and other methods known in the art.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Chemical Definitions

The term 'alkyl' refers to a straight or branched $C_1$-$C_{20}$ hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl). The alkyls used herein are preferably $C_1$-$C_8$ alkyls.

The term "alkenyl" refers to a $C_2$-$C_{20}$ aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronapthyl, adamantyl and norbornyl groups bridged cyclic group or sprirobicyclic groups, e.g., spiro (4,4) non-2-yl.

The term "cycloalkalkyl" refers to a cycloalkyl as defined above directly attached to an alkyl group as defined above, that results in the creation of a stable structure such as cyclopropylmethyl, cyclobutylethyl, cyclopentylethyl.

The term "alkyl ether" refers to an alkyl group or cycloalkyl group as defined above having at least one oxygen incorporated into the alkyl chain, e.g., methyl ethyl ether, diethyl ether, tetrahydrofuran.

The term "alkyl amine" refers to an alkyl group or a cycloalkyl group as defined above having at least one nitrogen atom, e.g., n-butyl amine and tetrahydrooxazine.

The term "aryl" refers to aromatic radicals having in the range of about 6 to about 14 carbon atoms such as phenyl, naphthyl, tetrahydronapthyl, indanyl, biphenyl.

The term "arylalkyl" refers to an aryl group as defined above directly bonded to an alkyl group as defined above, e.g., —$CH_2C_6H_5$, and —$C_2H_4C_6H_5$.

The term "heterocyclic" refers to a stable 3- to 15-membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolidinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The heterocyclic ring radical may be attached to the main structure at any heteroatom or carbon atom that results in the creation of a stable structure.

The term "heteroaryl" refers to a heterocyclic ring wherein the ring is aromatic.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocylic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to alkyl group. The heterocyclylalkyl radical may be attached to the main structure at carbon atom in the alkyl group that results in the creation of a stable structure.

The substituents in the 'substituted alkyl', 'substituted alkenyl' 'substituted alkynyl' 'substituted cycloalkyl' 'substituted cycloalkalkyl' 'substituted cyclocalkenyl' 'substituted arylalkyl' 'substituted aryl' 'substituted heterocyclic ring', 'substituted heteroaryl ring,' 'substituted heteroarylalkyl', or 'substituted heterocyclylalkyl ring', may be the same or different with one or more selected from the groups hydrogen, hydroxy, halogen, carboxyl, cyano, amino, nitro, oxo (=O), thio (=S), or optionally substituted groups selected from alkyl, alkoxy, alkenyl, alkynyl, aryl, arylalkyl, cycloalkyl, aryl, heteroaryl, heteroarylalkyl, heterocyclic ring, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(=N—N($R^x$)$R^y$), —$NR^xC(O)OR^y$, —$NR^xR^y$, —$NR^xC(O)R^y$—, —$NR^xC(S)R^y$—$NR^xC(S)NR^yR^z$, —$SONR^xR^y$—, —$SO_2NR^xR^y$—, —$OR^x$, —$OR^xC(O)$ $NR^yR^z$, —$OR^xC(O)OR^y$—, —$OC(O)R^x$, —$OC(O)NR^xR^y$, —$R^xNR^yR^z$, —$R^xR^yR^z$, —$R^xCF_3$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, —$ONO_2$, wherein $R^x$, $R^y$ and $R^z$ in each of the above groups can be hydrogen atom, substituted or unsubstituted alkyl, haloalkyl, substituted or unsubstituted arylalkyl, substituted or unsubstituted aryl, substituted or unsubstituted cycloalkyl, substituted or unsubstituted cycloalkalkyl substituted or unsubstituted heterocyclic ring, substituted or unsubstituted heterocyclylalkyl, substituted or unsubstituted heteroaryl or substituted or unsubstituted heteroarylalkyl.

The term "halogen" refers to radicals of fluorine, chlorine, bromine and iodine.

DNJ and DNJ Derivatives

It has been found that derivatives of 1-deoxynojirimycin (Compound 1, DNJ; 1,5-imino-1,5-dideoxy-D-glucitol-CAS No. 19130-96-2) are useful for treating Pompe disease. DNJ has molecular formula $C_6H_{13}NO_4$ and a molecular weight of 163.2. DNJ is described in U.S. Pat. No. 4,806,650 to Schroder et al. and has the following structure:

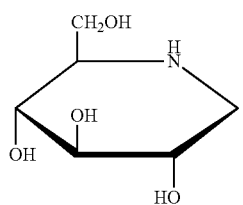

1

The derivatives of DNJ useful in the present invention can be described by the formula:

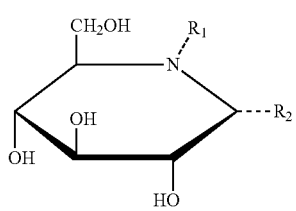

II where $R_1$ is H or a straight or branched alkyl, alkenyl, alkylether or alkyl amine containing 1-12 carbon atoms, alkylaryl, heteroaryl, or heteroaryl alkyl containing 5-12 ring atoms, where $R_1$ is optionally substituted with one or more —OH, —COOH, —Cl, —F, —CF$_3$, —OCF$_3$, —C(=O)N-(alkyl)$_2$ (i.e., —O—C(=O)N—(Me)$_2$) and $R_2$ is H; a straight or branched alkyl, cycloalkyl, alkenyl, or alkylether, containing 1-9 carbon atoms or aryl containing 5-12 carbon atoms, wherein $R_2$ is optionally substituted with —OH, —COOH, —CF$_3$, —OCF$_3$ or a heterocyclic ring.

At least one of $R_1$ and $R_2$ is not H.

Preferred DNJ derivatives include N-alkyl derivatives having 1-12 carbon atoms. More preferred, these derivatives are straight chain, branched or cyclic compounds having 1-9 carbon atoms. Exemplary compounds include, but are not limited to N-methyl-DNJ (2), N-ethyl-DNJ (3), N-propyl-DNJ (4), N-butyl-DNJ (5), N-pentyl-DNJ (6), N-hexyl-DNJ (7), N-heptyl-DNJ (8), N-octyl-DNJ (9), N-nonyl-DNJ, (10), N-methylcyclopropyl-DNJ (11) and N-methylcyclopentyl-DNJ (12).

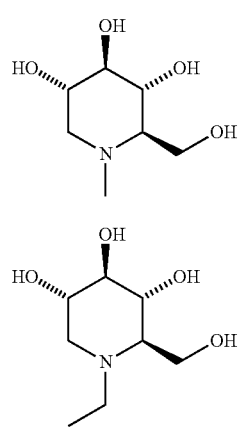

2

3

-continued

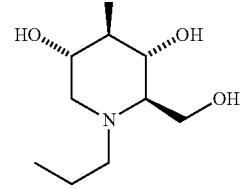

4

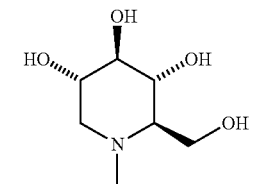

5

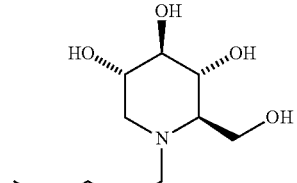

6

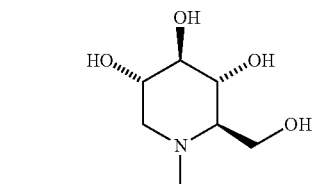

7

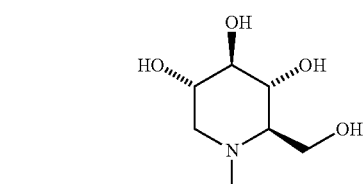

8

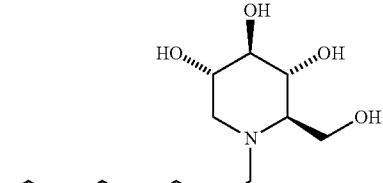

9

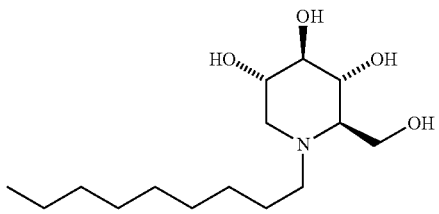

10

-continued

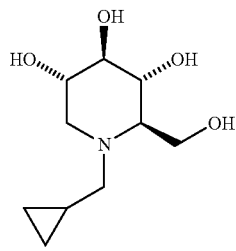

11

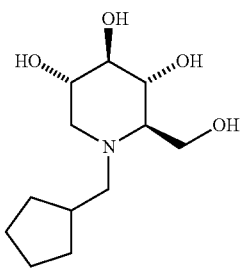

12

One preferred alkyl DNJ derivative is N-methyl-1-deoxynojirimycin (Compound 2, N-methyl DNJ; N-methylmoranoline, 1,5-(methylimino)-1,5-dideoxy-D-glucitol) is a synthetic glucose analogue which is commercially available from Toronto Research Chemicals, Cat. Number M297000, CAS 69567-1-08. N-methyl DNJ reduces the glycogenolytic rate by inhibiting the α-1,6-glucosidase of glycogen-debranching enzyme in the liver, and possesses an antihyperglycemic action by blocking α-1,4-glucosidase (Arai M et al., *Circulation*. 1998 Apr. 7; 97(13):1290-7).

Another preferred alkyl DNJ derivative is N-nonyl-deoxynojirimycin (Compound 10, N-nonyl DNJ; 1,5-(nonylimino)-1,5-dideoxy-D-glucitol), a synthetic glucose analogue that is useful for the treatment of Gaucher disease (a lysosomal storage disease characterized by glycolipid accumulation). (Sawkar A R, et al., *Proc Natl Acad Sci USA*. 2002; 26; 99(24):15428-33).

Alkyl DNJ derivatives having a substituent such as an —OH, —COOH, or OCF₃ are also preferred compounds. Exemplary substituted alkyl DNJ derivatives include, but are not limited to:

13

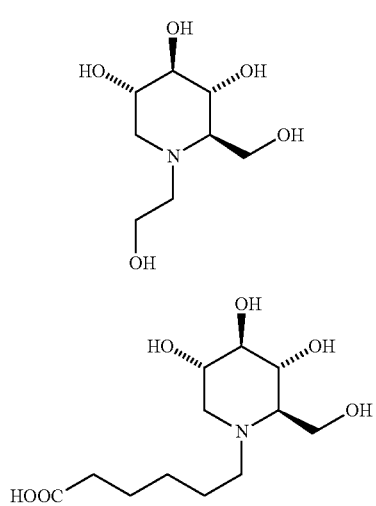

14

-continued

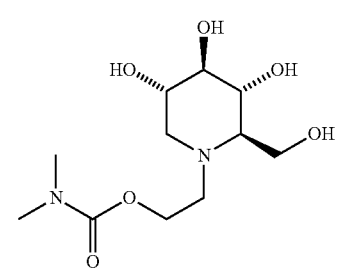

15

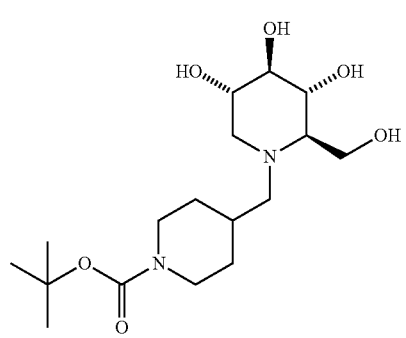

16

A preferred DNJ derivative is N-2-hydroxyethyl-deoxynojirimycin (Compound 13, N-ethoxy DNJ; 1,5-(2-hydroxyethylimino)-1,5-dideoxy-D-glucitol; miglitol), a synthetic glucose analogue used to treat Type 2 diabetes mellitus. Drent et al., *Diabetes Nutr Metab*. 2002; 15(3): 152-9; de Luis Roman D A, *Rev Clin Esp*. 2004 January; 204(1):32-4.

Another preferred DNJ derivative is 5-N-carboxypentyl deoxynojirimycin (Compound 14, 5-N-carboxypentyl DNJ; 1,5-(5-N-carboxypentylimino)-1,5-dideoxy-D-glucitol).
This synthetic glucose analogue may be synthesized by the route described by Bernotas R C, et al., *Biochem J*. 1990 Sep. 1; 270(2):539-40.

Additional DNJ derivatives are alkyl ether derivatives such as the compounds:

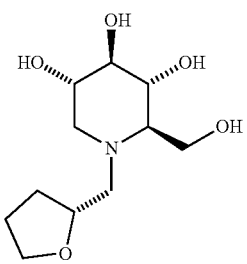

17

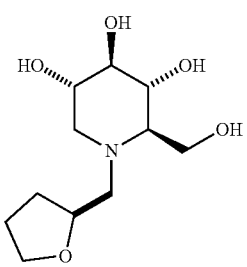

18

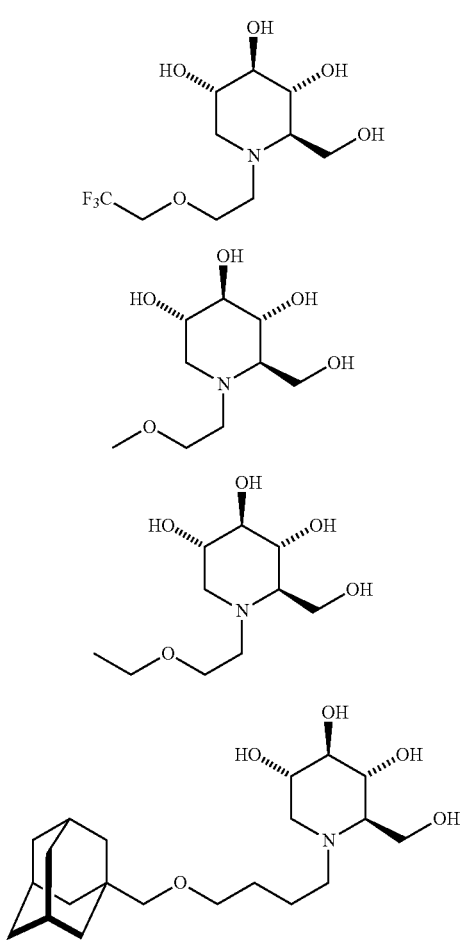
Other preferred compounds include derivatives such as the N-benzyl substituted DNJ derivatives represented by the formula:
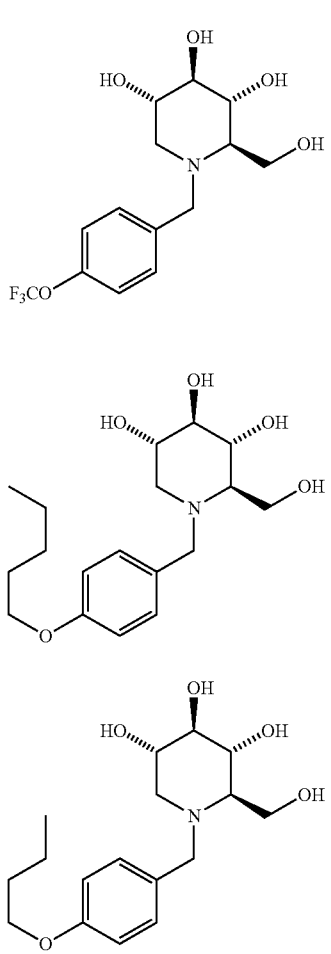
Other preferred compounds include derivatives such as the N—CH₂—Ar substituted DNJ derivatives represented by the formula, wherein Ar is an aromatic heterocycle:

23

-continued

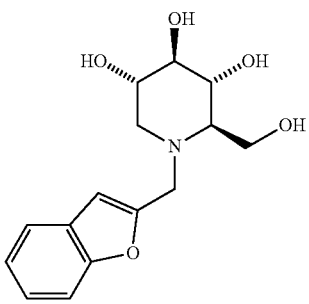
30

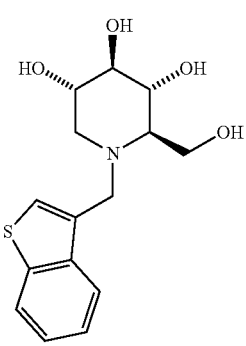
31

In addition to the nitrogen-substituted DNJ derivatives, DNJ derivatives having a substituent appended to the C-1 carbon adjacent to the ring nitrogen are also preferred compounds of the present invention. These compounds include, but are not limited to:

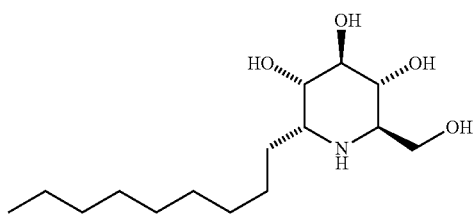
32

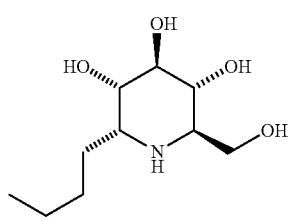
33

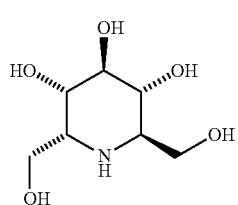
34

24

-continued

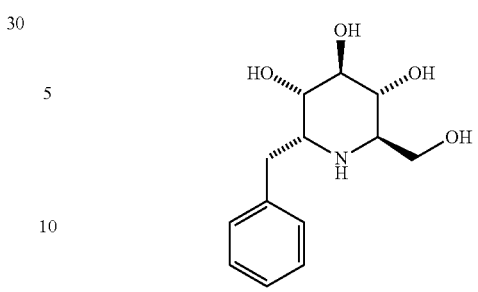
35

Where straight chain hydrocarbon analogs include but are not limited to 1-12 carbon atoms and R includes but is not limited to: branched alkyl, cycloalkyl, or alkyl optionally substituted with —OH, —COOH, —CF$_3$, —OCF$_3$, NHR, NHCOR' or an aromatic or heterocyclic ring, wherein R' is an alkyl group.

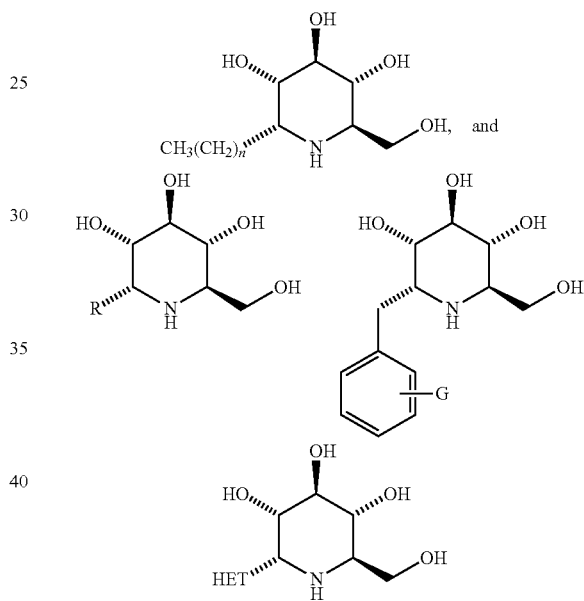

where HET is a heterocyclic group such as tetrahydrofuran, pyridine, furan, pyrrole, imidazole, triazole, tetrazole, oxazole, thiazole and the appended benzo-analogs. etc, Ar is a phenyl or substituted phenyl. Phenyl substituents may consist of G which is a functional group (e.g., CH$_3$, Cl, F, or CH$_2$—O—CF$_3$) and n is an integer between 0 and 5.

Synthesis of DNJ Derivatives

The compounds of the present invention having a substitution at R$_1$ can be synthesized from DNJ as described in: EP 49858, WO2005/063706, U.S. Pat. No. 4,639,436; WO 2004/037373; WO 95/22975; U.S. Pat. Nos. 5,399,567; 5,310,745; Bols et al., *Journal of Carbohydrate Chemistry* 2004 23(4), 223-238, Sawker et al., *Chemistry and Biology,* 2005; 12, 1235-1244, Overkleef, *Journal of Biological Chemistry.* 2005; 273(41), 26522-26527; Tan et al., *Journal of Bilogical Chemistry.* 1991, 266(22), 14504-14510; Romaniouk et al., *Glycobiology.* 2004; 14(4), 301-310; Lesur, Bioorganic and *Medicinal Chemistry Letters* 1997; 7(3), 355-360; Yoshikuni, *Agric. Biol. Chem* 1998; 52(1), 121), and by known modifications of these methods. The compounds of the present invention having a substitution at $R_2$ can be synthesized from DNJ as described in: Anzeveno, et al., *J. Org. Chem.* 1989; 54(11), 2539; WO 00/56713; U.S. Pat. No. 4,880,917; EP 0315017; and U.S. Pat. No. 5,051, 407, and by Boshagen et al, *Angewante Chemie, Int.* Ed. Engl. 1981; 20(9), 806-807, and by Additional methods that have been reported and known modifications of these methods are demonstrated in WO00/56713, U.S. Pat. No. 5,051, 407, and EP 0315017. Another approach to the synthesis of these molecules has been reported by Davis in *Angewante Chemie*, Int. Ed. Engl. 2003; 42, 3788-3792.

The compounds of the present invention can also be synthesized from a tetra-OBn gluconolactone. This synthesis can be adapted from the syntheses described in: Perrine et al., *J.Org. Chem.* 1967; 32, 664; Matos, Lopes & Lopes, *Synthesis* 1999; 4, 571; Rao & Perlin; *Can. J. Chem.* 1981; 59, 333; Hoos, Naughton and Vassella, *Helv. Chim. Acta,* 1993; 76, 1802, and Baxter & Reitz, *J. Org. Chem.* 1994; 59, 3175.

A semi-synthetic approach may also be used to form the DNJ derivatives of the present invention. This enzymatic route uses *Gluconobacter Oxydans*, and can be adapted from the methods described in: U.S. Pat. Nos. 4,266,025; 5,695, 969; 4,246,345; 4,806,650; 0,430,307; and Kinast & Schedel; *Angew. Chem. Int. Ed. Engl.,* 20, 805 (1981).

Some compounds useful in the present invention can be purchased, for example, the following compounds were purchased from Toronto Research Chemicals: 1-Deoxynojirimycin (Cat. No. D245000), 1-Deoxynojirimycin hydrochloride (Cat. No. D245005), N-Butyl-1-Deoxynojirimycin (Cat. No. B691000, CAS[21011-90-0]), Miglitol (Cat. No. M344200, CAS[72432-03-2]), N-Methyl-1-Deoxynojirimycin (Cat. No. 297000, CAS[69567-1-8], N-5-Carboxypentyl-1-Deoxynojirimycin (Cat. No. C181200), N-(5-Adamantane-1-yl-methoxy)-Pentyl-1-Deoxynojirimycin (Cat. No. A21000); α-homonnojirimycin was purchased from TCI America (Cat. No. H11144, CAS 119557-99-2.

A non-limiting listing of the compounds that may be used in the present invention include: DNJ, N-butyl DNJ, N-(cyclopropyl)methyl DNJ, N-2-(tetrahydrofuran)methyl DNJ, N-2-oxoethyl DNJ trifluoroethy ether/N-(2-(2,2,2-trifluoroethoxy)ethyl DNJ, N-ethyloxy DNJ dimethyl carbamate/N-(2-(N,N-dimethylamido)ethyloxy) DNJ, N-methyl-DNJ, 2-methoxyethyl DNJ, 2-ethoxyethyl DNJ, 4-trifluoromethyl-benzyl DNJ, α-cyano-4-trifluoromethyl-benzyl DNJ, 4-pentoxybenzyl DNJ, 4-butoxybenzyl DNJ, 4-t-BOC-piperidinylmethyl DNJ, α-C6-n-nonyl-DNJ, and α-homo-DNJ. The percent enhancement relative to 1 mM DNJ at which one-half maximal enhancement is observed are given for these compounds in the Tables 1 and 2 below (Example 2).

Additional compounds contemplated for use in this invention include N-nonyl DNJ (10); Miglitol (13); N-5-carboxypentyl-1-DNJ (14); Methyl-2-benzofuranyl DNJ (30); Methyl-2-benzothiaphenyl DNJ (31); α-C6-n-Butyl-DNJ (33); Methyl-2-furanyl DNJ (29); N-n-hexyl DNJ (7); N-ethyl DNJ (3); N-n-propyl DNJ (4); N-n-pentyl DNJ (6); and β-C6-Benzyl-DNJ (36); 2-(N-(Benzo[d][1,3]dioxol-5-yl)-N-methylamino)ethyl)-DNJ (28); and N-2-(N-methyl-N-methylenedioxyphenylamino)ethyl-DNJ (37).

Activity and Localization Assays

Enhanced activity, stability and/or trafficking of Gaa can be determined by measuring an increase in cellular Gaa polypeptide, by determining an increase in trafficking to the lysosome, e.g., or by determining increased Gaa activity or stability. Non-limiting exemplary methods for assessing each of the foregoing are described below.

Determining Gaa Intracellular Expression.

Methods for determining intracellular LPL protein levels are known in the art. Such methods include Western blotting, immunoprecipitation followed by Western blotting (IP Western), or immunofluorescence using a tagged LPL protein.

Determining Gaa Trafficking.

Assessing trafficking of proteins through the biosynthetic pathway can be achieved e.g., using pulse-chase experiments with $^{35}$S-labeled receptor protein, in conjunction with glycosidases; or, preferably, by indirect or direct immunofluorescence to determine protein modification during trafficking. These and other methods are described for example in *Current Protocols in Cell Biology* 2001; John Wiley & Sons. Exemplary immunofluorescence experiments to detect lysosomal trafficking of Gaa are described in detail in Examples 3 and 4 below.

Other methods for detecting impaired trafficking of proteins are well known in the art. For example, for proteins which are N- and/or O-glycosylated in the Golgi apparatus, pulse-chase metabolic labeling using radioactively labeled proteins, combined with glycosidase treatment and immunoprecipation, can be used to detect whether the proteins are undergoing full glycosylation in the Golgi, or whether they are being retained in the ER instead of trafficking to the Golgi for further glycosylation.

Sensitive methods for visually detecting cellular localization also include fluorescent microscopy using fluorescent proteins or fluorescent antibodies. For example, LPL proteins of interest can be tagged with e.g., green fluorescent protein (GFP), cyan fluorescent protein, yellow fluorescent protein, and red fluorescent protein, followed by multicolor and time-lapse microscopy and electron microscopy to study the fate of these proteins in fixed cells and in living cells. For a review of the use of fluorescent imaging in protein trafficking, see Watson et al., *Adv Drug Deliv Rev* 2005; 57(1):43-61. For a description of the use of confocal microscopy for intracellular co-localization of proteins, see Miyashita et al., *Methods Mol Biol.* 2004; 261:399-410.

Fluorescence correlation spectroscopy (FCS) is an ultrasensitive and non-invasive detection method capable of single-molecule and real-time resolution (Vukojevic et al., *Cell Mol Life Sci* 2005; 62(5): 535-50). SPFI (single-particle fluorescence imaging) uses the high sensitivity of fluorescence to visualize individual molecules that have been selectively labeled with small fluorescent particles (Cherry et al., *Biochem Soc Trans* 2003; 31 (Pt 5): 1028-31). For a review of live cell imaging, see Hariguchi, *Cell Struct Funct* 2002; 27(5):333-4).

Fluorescence resonance energy transfer (FRET) microscopy is also used to study the structure and localization of proteins under physiological conditions (Periasamy, *J Biomed Opt* 2001; 6(3): 287-91).

Determining an Increase in Gaa Activity.

In vitro, Gaa activity can be determined as described below in Example 2. Gaa activity can be determined in vivo following treatment with pharmacological chaperones using mixed lymphocytes as described in Okumiya et al., *Mol Genet Metab.* 2006 May; 88(1):22-8. The method employs glycogen and 4-methylumbelliferyl-alpha-d-glucopyranoside (4MU-alphaGlc) as substrates for measuring the lysosomal acid α-glucosidase activity, and incorporates acarbose to eliminate the interference of unrelated α-glucosidases (predominantly maltase-glucoamylase).

Formulation, Dosage, and Administration

In one embodiment, the chaperone compound is administered as monotherapy, preferably in an oral dosage form (described further below), although other dosage forms are contemplated. In this embodiment, it is contemplated that the dosing regimen should be one that provides a constant, steady state level of compound in the plasma of the Pompe patient. This can be obtained either by daily administration in divided doses, or controlled-release formulations, or by less frequent administration of sustained-release dosage forms. Formulations, dosage, and routes of administration for the chaperone compound are detailed below.

Formulations

In one embodiment of the invention, the chaperone compound is administered as monotherapy, and can be in a form suitable for any route of administration, including e.g., orally in the form tablets or capsules or liquid, in sterile aqueous solution for injection, or in a dry lyophilized powder to be added to the formulation of the replacement Gaa (see below) during or immediately after reconstitution to prevent enzyme aggregation in vitro prior to administration.

When the chaperone compound is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active chaperone compound.

ZAVESCA®, a chaperone compound contemplated for use in the method of the present invention, is commercially available as hard gelatin capsules, each containing 100 mg of DNJ, sodium starch glycollate, povidone (K30) and magnesium stearate. The capsule shell includes gelatin and titanium dioxide.

The pharmaceutical formulations of the chaperone compound suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the purified Gaa and the chaperone compound in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Administration

The route of administration of the chaperone compound may be oral (preferably) or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of the chaperone compound may be by periodic injections of a bolus of the preparation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780, 014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

Dosage

The amount of chaperone compound effective to rescue the endogenous mutant Gaa (and/or stabilize the administered purified Gaa-see the combination therapy section below) can be determined on a case-by-case basis by those skilled in the art. Pharmacokinetics and pharmacodynamics such as half-life ($t_{1/2}$), peak plasma concentration ($C_{max}$), time to peak plasma concentration ($t_{max}$), exposure as measured by area under the curve (AUC), and tissue distribution for both the replacement protein and the chaperone compound, as well as data for chaperone/replacement Gaa binding (affinity constants, association and dissociation constants, and valency), can be obtained using ordinary methods known in the art to determine compatible amounts required to stabilize the replacement protein, without inhibiting its activity, and thus confer a therapeutic effect.

Data obtained from cell culture assay or animal studies may be used to formulate a therapeutic dosage range for use in humans and non-human animals. The dosage of compounds used in therapeutic methods of the present invention preferably lie within a range of circulating concentrations that includes the $ED_{50}$ concentration (effective for 50% of the tested population) but with little or no toxicity. The particular dosage used in any treatment may vary within this range, depending upon factors such as the particular dosage form employed, the route of administration utilized, the conditions of the individual (e.g., patient), and so forth.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms (e.g., as determined from the cell culture assays). Appropriate dosages for use in a particular individual, for example in human patients, may then be more accurately determined using such information.

Measures of compounds in plasma may be routinely measured in an individual such as a patient by techniques such as high performance liquid chromatography (HPLC) or gas chromatography.

Toxicity and therapeutic efficacy of the composition can be determined by standard pharmaceutical procedures, for example in cell culture assays or using experimental animals to determine the $LD_{50}$ and the $ED_{50}$. The parameters $LD_{50}$ and $ED_{50}$ are well known in the art, and refer to the doses of a compound that is lethal to 50% of a population and therapeutically effective in 50% of a population, respectively. The dose ratio between toxic and therapeutic effects is referred to as the therapeutic index and may be expressed as the ratio: $LD_{50}/ED_{50}$. Chaperone compounds that exhibit large therapeutic indices are preferred.

As one exemplary dosage regimen, N-butyl-DNJ (ZAVESCA®) is administered for the treatment of Gaucher disease in oral doses of 100 to 300 mg per day in divided doses (two to three times per day). Following administration of 100 mg, the $t_{max}$ ranged from 2 to 2.5 hrs in Gaucher patients. The half-life of ZAVESCA® is about 6 to 7 hours, which predicts that steady-state will be achieved by 1.5 to 2 days following three times daily dosing. There is no evidence that ZAVESCA® is metabolized in humans.

For optimal chaperone activity of Gaa, it is expected that lower doses of the DNJ derivatives that those required to inhibit glycolipid synthesis will be effective. For example, doses of between 5 and 150 mg/day, particularly between 5-75 mg/day are preferred for the DNJ derivatives having higher Gaa-enhancing activity. Some DNJ derivatives may require slightly higher doses due to lowered Gaa-enhancing activity.

The optimal concentrations of the chaperone compound will be determined according to the amount required to stabilize and induce a proper conformation of the recombinant protein in vivo, in tissue or circulation, without preventing its activity, bioavailability of the chaperone compound in tissue or in circulation, and metabolism of the chaperone compound in tissue or in circulation. For example, where the chaperone compound is an enzyme inhibitor, the concentration of the inhibitor can be determined by calculating the $IC_{50}$ value of the specific chaperone for the enzyme. Taking into consideration bioavailability and metabolism of the compound, concentrations around the $IC_{50}$ value or slightly over the $IC_{50}$ value can then be evaluated based on effects on enzyme activity, e.g., the amount of inhibitor needed to increase the amount of enzyme activity or prolong enzyme activity of the administered enzyme. As an example, the $IC_{50}$ value of the compound deoxygalactonojiromycin (DGJ) for the α-Gal A enzyme is 0.04 µM, indicating that DGJ is a potent inhibitor. Accordingly, it is expected that the intracellular concentration of α-Gal A would be much lower than that of the α-Gal A administered.

Combination Therapy with Enzyme Replacement Therapy

Enzyme replacement therapy increases the amount of protein by exogenously introducing wild-type or biologically functional enzyme by way of infusion. This therapy has been developed for many genetic disorders including lysosomal storage disorders Gaucher disease and Fabry disease, as referenced above. The wild-type enzyme is purified from a recombinant cellular expression system (e.g., mammalian cells or insect cells-see U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al.; and U.S. Pat. No. 5,879,680 to Ginns et al.), human placenta, or animal milk (see U.S. Pat. No. 6,188,045 to Reuser et al.). After the infusion, the exogenous enzyme is expected to be taken up by tissues through non-specific or receptor-specific mechanism. In general, the uptake efficiency is not high, and the circulation time of the exogenous protein is short (Ioannu et al., Am. J. Hum. Genet. 2001; 68: 14-25). In addition, the exogenous protein is unstable and subject to rapid intracellular degradation as well as having the potential for adverse immunological reactions with subsequent treatments.

Enzyme replacement for Pompe disease has been described by several groups, Klinge et al., *Neuropediatrics*. 2005; 36(1): 6-11; Klinge et al., *Neuromuscul Disord*. 2005; 15(1): 24-31; Van den Hout et al., *J Inherit Metab Dis*. 2001; 24(2): 266-74; and Amalfitano et al., *Genet Med*. 2001; 3(2): 132-8, with limited success. Recombinant Gaa for human administration is described in Van den Hout et al., *Lancet*. 2000; 56: 397-8.

The present invention increases the effectiveness of protein replacement therapy by increasing the stability of the purified protein in vivo in Pompe patients having a mutated Gaa characterized by misfolding, by co-administration of an ASSC for the protein, and in vitro in a formulation or composition.

In one embodiment, the replacement Gaa and the chaperone compound are formulated in separate compositions. In this embodiment, the DNJ derivative chaperone compound and the replacement Gaa may be administered according to the same route, e.g., intravenous infusion, or preferably, by different routes, e.g., intravenous infusion for the replacement enzyme, and oral administration for the chaperone compound as described in the section above.

The replacement Gaa is administered by any of the routes described above for administration of the chaperone, but preferably administration is parenteral. More preferably, administration is intravenously in a sterile solution for injection.

In another embodiment, the chaperone compound and replacement Gaa are formulated in a single composition. Such a composition enhances stability of the enzyme during storage and in vivo administration, thereby reducing costs and increasing therapeutic efficacy. The formulation is preferably suitable for parenteral administration, including intravenous subcutaneous, and intraperitoneal, however, formulations suitable for other routes of administration such as oral, intranasal, or transdermal are also contemplated.

Timing of Administration.

When the replacement Gaa and chaperone compound are in separate formulations, administration may be simultaneous, or the chaperone compound may be administered prior to, or after the replacement Gaa. For example, where the replacement enzyme is administered intravenously, the chaperone compound may be administered during a period from 0 hours to 6 hours later. Alternatively, the chaperone compound may be administered from 0 to 6 hours prior to the protein.

In a preferred embodiment, where the chaperone compound and replacement protein are administered separately, and where the chaperone compound has a short circulating half-life (e.g., small molecule), the chaperone compound may be orally administered continuously, such as daily, in order to maintain a constant level in the circulation. Such constant level will be one that has been determined to be non-toxic to the patient, and optimal regarding interaction with a target replacement protein during the time of administration to confer a non-inhibitory, therapeutic effect.

In another embodiment, the chaperone compound is administered during the time period required for turnover of the replacement Gaa (which will be extended by administration of the chaperone compound).

Dose of Replacement Gaa.

According to current methods, the concentration of replacement enzyme is generally between about 0.05-5.0 mg/kg of body weight, typically administered weekly or biweekly. The enzyme can be administered at a dosage ranging from 0.1 gig/kg to about 10 mg/kg, preferably from about 0.1 mg/kg to about 2 mg/kg. For example, for the treatment of Fabry disease, the dose of recombinant α-Gal A administered is typically between 0.1-0.3 mg/kg and is administered weekly or biweekly. Regularly repeated doses of the protein are necessary over the life of the patient. Subcutaneous injections maintain longer term systemic exposure to the drug. The subcutaneous dosage is preferably 0.1-5.0 mg of the α-Gal A per kg body weight biweekly or weekly. The α-Gal A is also administered intravenously, e.g., in an intravenous bolus injection, in a slow push intravenous injection, or by continuous intravenous injection. Continuous IV infusion (e.g., over 2-6 hours) allows the maintenance of specific levels in the blood.

It is expected that the effective dose of recombinant or purified Gaa will be higher than that required in Fabry or Gaucher disease, due to the fact that the target tissue in Pompe, skeletal muscle, is shielded from recombinantly administered enzyme by endothelial and interstitial tissue. Recombinant Gaa (Myozyme, Genzyme, Inc.) is currently approved for the treatment Pompe disease. Additional trials are being conducted at Duke University in conjunction with Synpac, Inc., and in Europe. In one European study, infantile Pompe patients were started at a dose of 15 and 20 mg/kg per week of recombinant human Gaa from rabbit milk, while during the study, based on monitoring of muscle tissue activity levels, the dose was increased to 40 mg/kg in a once a week intravenous infusion. The study was continued for 144 infusions over 36 weeks (Van den Hout et al., *Pediatrics*. 2004; 113: 448-57). In one trial in several late-onset Pompe patients, recombinant human Gaa from rabbit milk was administered intravenously as a 1 to 2 mg/ml solution in saline with 5% glucose and 0.1% human serum albumin, initially in weekly doses of 10 mg/kg, increasing up to 20 mg/kg (Winkel et al., *Ann Neurol*. 2004; 55: 495-502).

Combination Therapy with Gene Therapy

Although not yet approved for therapeutic treatment in the United States, gene therapies (both ex vivo and direct transfer) for numerous genetic disorders are under investigation. The present invention also contemplates use of the chaperone compound in combination with gene therapy to replace the defective Gaa in Pompe disease. Such a combination will enhance the efficacy of gene therapy by increasing the level of expression of the therapeutic Gaa in vivo, since, in addition to enhancing folding and processing of mutated enzymes, small molecule chaperones have been shown to enhance folding and processing of the wild-type or conformationally stable counterparts (see, e.g., U.S. Pat. No. 6,274,597 to Fan et al., Example 3).

Recently, Sun et al. (*Mol Ther*. 2005; 11(1): 57-65) have employed an adeno-associated virus (AAV) vector encoding human Gaa (hGaa; pseudotyped as AAV8 (AAV2/8)) for intravenous injection into an immunodeficient mouse model of Pompe disease (Gaa knock-out/SCID mice). High levels of hGaa were maintained in plasma for 24 weeks following AAV2/8 vector administration. Gaa deficiency in the heart and skeletal muscle was corrected with the AAV2/8 vector in male mice, while female mice had correction only in the heart Any of the methods for gene therapy which are or become available in the art can be used to deliver therapeutic genes. Exemplary methods are described below. For general reviews of the methods of gene therapy, see Goldspiel et al., *Clinical Pharmacy* 1993, 12:488-505; Wu and Wu, Biotherapy 1991, 3:87-95; Tolstoshev, *Ann. Rev. Pharmacol. Toxicol*. 1993, 32:573-596; Mulligan, *Science*. 1993, 260: 926-932; and Morgan and Anderson, *Ann. Rev. Biochem*. 1993, 62:191-217; May, *TIBTECH* 1993, 11:155-215. Methods commonly known in the art of recombinant DNA technology that can be used are described in Ausubel et al., (eds.), 1993, *Current Protocols in Molecular Biology*, John Wiley & Sons, NY; Kriegler, 1990, Gene Transfer and Expression, *A Laboratory Manual*, Stockton Press, NY; and in Chapters 12 and 13, Dracopoli et al., (eds.), 1994, *Current Protocols in Human Genetics*, John Wiley & Sons, NY; and Colosimo et al., *Biotechniques* 2000; 29(2):314-8, 320-2, 324.

The Gaa gene to be administered for the methods of the present invention can be isolated and purified using ordinary molecular biology, microbiology, and recombinant DNA techniques within the skill of the art. For example, nucleic acids encoding the target protein can be isolated using recombinant DNA expression as described in the literature. See, e.g., Sambrook, Fritsch & *Maniatis, Molecular Cloning: A Laboratory Manual*, Second Edition (1989) Cold Spring Harbor Laboratory Press, Cold Spring Harbor, N.Y.; *DNA Cloning: A Practical Approach*, Volumes I and II (D. N. Glover ed. 1985); Oligonucleotide Synthesis (M. J. Gait ed. 1984); Nucleic Acid Hybridization [B. D. Hames & S. J. Ê Higgins eds. (1985)]; Transcription And Translation [B. D. Hames & S. J. Higgins, eds. (1984)]; *Animal Cell Culture* [R. I. Freshney, ed. (1986)]; Immobilized Cells And Enzymes [IRL Press, (1986)]; B. E Perbal, *A Practical Guide To Molecular Cloning* (1984). The nucleic acid encoding the protein may be full-length or truncated, so long as the gene encodes a biologically active protein.

The identified and isolated Gaa gene can then be inserted into an appropriate cloning vector. Vectors suitable for gene therapy include viruses, such as adenoviruses, adeno-associated virus (AAV), vaccinia, herpesviruses, baculoviruses and retroviruses, parvovirus, lentivirus, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

In a preferred embodiment, the vector is a viral vector. Viral vectors, especially adenoviral vectors can be complexed with a cationic amphiphile, such as a cationic lipid, polyL-lysine (PLL), and diethylaminoethyldextran (DE-LAE-dextran), which provide increased efficiency of viral infection of target cells (See, e.g., PCT/US97/21496 filed Nov. 20, 1997, incorporated herein by reference). Preferred viral vectors for use in the present invention include vectors derived from vaccinia, herpesvirus, AAV and retroviruses. In particular, herpesviruses, especially herpes simplex virus (HSV), such as those disclosed in U.S. Pat. No. 5,672,344, the disclosure of which is incorporated herein by reference, are particularly useful for delivery of a transgene to a neuronal cell. AAV vectors, such as those disclosed in U.S. Pat. Nos. 5,139,941, 5,252,479 and 5,753,500 and PCT publication WO 97/09441, the disclosures of which are incorporated herein, are also useful since these vectors integrate into host chromosomes, with a minimal need for repeat administration of vector. For a review of viral vectors in gene therapy, see McConnell et al., *Hum Gene Ther.* 2004; 15(11):1022-33; Mccarty et al., *Annu Rev Genet.* 2004; 38:819-45; Mah et al., *Clin. Pharmacokinet.* 2002; 41(12): 901-11; Scott et al., *Neuromuscul. Disord.* 2002; 12 Suppl 1:S23-9. In addition, see U.S. Pat. No. 5,670,488. Beck et al., *Curr Gene Ther.* 2004; 4(4): 457-67, specifically describe gene therapy in cardiovascular cells.

The coding sequences of the gene to be delivered are operably linked to expression control sequences, e.g., a promoter that directs expression of the gene. As used herein, the phrase "operatively linked" refers to the functional relationship of a polynucleotide/gene with regulatory and effector sequences of nucleotides, such as promoters, enhancers, transcriptional and translational stop sites, and other signal sequences. For example, operative linkage of a nucleic acid to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

In one specific embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, *Proc. Natl. Acad. Sci. USA*. 1989, 86:8932-8935; Zijlstra et al., *Nature*. 1989, 342:435-438; U.S. Pat. No. 6,244,113 to Zarling et al.; and U.S. Pat. No. 6,200,812 to Pati et al.).

Gene Delivery

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

Direct Transfer.

In a specific embodiment, the vector is directly administered in vivo, where it enters the cells of the organism and mediates expression of the gene. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-(3-1-64-N-acetylglucosamine polysaccharide; see U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, *J. Biol. Chem.* 1987, 62:4429-4432), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., *Mol. Therapy*. 2000, 2:339-47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Recently, a technique referred to as magnetofection has been used to deliver vectors to mammals. This technique associates the vectors with superparamagnetic nanoparticles for delivery under the influence of magnetic fields. This application reduces the delivery time and enhances vector efficacy (Scherer et al., *Gene Therapy*. 2002; 9:102-9). Additional targeting and delivery methodologies are contemplated in the description of the vectors, below.

In a specific embodiment, the nucleic acid can be administered using a lipid carrier. Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, *Nature.* 1989; 337:387). Intravenous injection of cationic lipid-plasmid complexes into mice has been shown to result in expression of the DNA in lung (Brigham et al., *Am. J. Med. Sci.* 1989; 298:278). See also, Osaka et al., *J. Pharm. Sci.* 1996; 85(6):612-618; San et al., *Human Gene Therapy.* 1993; 4:781-788; Senior et al., *Biochemica et Biophysica Acta.* 1991; 1070:173-179); Kabanov and Kabanov, *Bioconjugate Chem.* 1995; 6:7-20; Liu et al., *Pharmaceut. Res.* 1996; 13; Remy et al., *Bioconjugate Chem.* 1994; 5:647-654; Behr, J-P., *Bioconjugate Chem.* 1994; 5:382-389; Wyman et al., *Biochem.* 1997; 36:3008-3017; U.S. Pat. No. 5,939,401 to Marshall et al; and U.S. Pat. No. 6,331,524 to Scheule et al.

Representative cationic lipids include those disclosed, for example, in U.S. Pat. No. 5,283,185; and e.g., U.S. Pat. No. 5,767,099, the disclosures of which are incorporated herein by reference. In a preferred embodiment, the cationic lipid is N4-spermine cholesteryl carbamate (GL-67) disclosed in U.S. Pat. No. 5,767,099. Additional preferred lipids include N4-spermidine cholestryl carbamate (GL-53) and 1-(N4-spermine)-2,3-dilaurylglycerol carbamate (GL-89)

Preferably, for in vivo administration of viral vectors, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors. In that regard, it is advantageous to employ a viral vector that is engineered to express a minimal number of antigens.

Indirect Transfer.

Somatic cells may be engineered ex vivo with a construct encoding a wild-type protein using any of the methods described above, and re-implanted into an individual. This method is described generally in WO 93/09222 to Selden et al. In addition, this technology is used in Cell Based Delivery's proprietary ImPACT technology, described in Payumo et al., *Clin. Orthopaed. and Related Res.* 2002; 403S: S228-S242. In such a gene therapy system, somatic cells (e.g., fibroblasts, hepatocytes, or endothelial cells) are removed from the patient, cultured in vitro, transfected with the gene(s) of therapeutic interest, characterized, and reintroduced into the patient. Both primary cells (derived from an individual or tissue and engineered prior to passaging), and secondary cells (passaged in vitro prior to introduction in vivo) can be used, as well as immortalized cell lines known in the art. Somatic cells useful for the methods of the present invention include but are not limited to somatic cells, such as fibroblasts, keratinocytes, epithelial cells, endothelial cells, glial cells, neural cells, formed elements of the blood, muscle cells, other somatic cells that can be cultured, and somatic cell precursors. In a preferred embodiment, the cells are fibroblasts or mesenchymal stem cells.

Nucleic acid constructs, which include the exogenous gene and, optionally, nucleic acids encoding a selectable marker, along with additional sequences necessary for expression of the exogenous gene in recipient primary or secondary cells, are used to transfect primary or secondary cells in which the encoded product is to be produced. Such constructs include but are not limited to infectious vectors, such as retroviral, herpes, adenovirus, adenovirus-associated, mumps and poliovirus vectors, can be used for this purpose.

Transdermal delivery is especially suited for indirect transfer using cell types of the epidermis including keratinocytes, melanocytes, and dendritic cells (Pfutzner et al., *Expert Opin. Investig. Drugs.* 2000; 9:2069-83).

Mesenchymal stem cells (MSCs) are non-blood-producing stem cells produced in the bone marrow. MSCs can be made to differentiate and proliferate into specialized non-blood tissues. Stem cells transfected with retroviruses are good candidates for the therapy due to their capacity for self-renewal. This ability precludes repetitive administration of the gene therapy. Another advantage is that if the injected stem cells reach the target organ and then differentiate, they can replace the damaged or malformed cells at the organ.

In Vitro Stability

Ensuring the stability of a pharmaceutical formulation during its shelf life is a major challenge. Prior to development of a protein pharmaceutical, inherent or latent instabilities within the active ingredients must be explored and addressed. Instability of protein and peptide therapeutics is classified as chemical instability or physical instability. Examples of chemical instability are hydrolysis, oxidation and deamidation. Examples of physical instability are aggregation, precipitation and adsorption to surfaces. In addition, a protein may be subjected to stresses such as pH, temperature, shear stress, freeze/thaw stress and combinations of these stresses.

One of the most prevalent formulation problems is product aggregation, resulting in a loss in bioactivity. The addition of excipients may slow the process but may not completely prevent it. Activity losses may or may not be detected by physical assays and are only evident in bioassays or potency assays with large (sometimes 15-20%) coefficients of variation, making it difficult to determine actual losses.

In addition to stabilizing the replacement enzyme to be administered, the presence of a chaperone compound may enable the pharmaceutical formulation to be stored at a neutral pH of about 7.0-7.5. This will confer a benefit to enzymes that normally must be stored at a lower pH to preserve stability. For example, lysosomal enzymes, including Gaa, retain a stable conformation at a low pH (e.g., 5.0 or lower). However, extended storage of the replacement enzyme at a low pH may expedite degradation of the enzyme and/or formulation. The addition of a stabilizing chaperone compound may mitigate the need to store the replacement protein in acid.

Examples

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1: Synthesis of DNJ and Derivatives

Tetra-O-benzyl-1-Deoxynorjirimycin [General Iminosugar Prep-1]

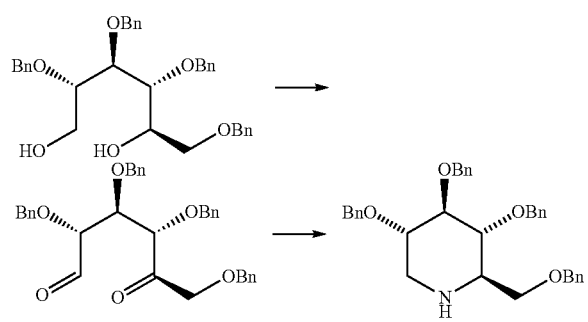

A solution of DMSO (4.4 mL, 0.124 mol) in dry CH$_2$Cl$_2$ (75 mL) is placed under an Argon atmosphere and cooled to −78° C. A solution of trifluoroacetic anhydride (6.1 mL, 0.088 mol) in dry CH$_2$Cl$_2$ (50 mL) is slowly added maintaining the temperature at −78° C. After the addition is complete, the reaction is stirred an additional 30 minutes, A solution of 2,3,4,6-Tetra-O-benzylglucitol (5.4 g, 10 mmol) in CH$_2$Cl$_2$ is added dropwise. Reaction is stirred at −78° C. for 90 minutes and then quenched by the addition of triethylamine (11.2 mL, 0.08 mol) in CH$_2$Cl$_2$ (50 mL). The reaction is warmed to 0° C. and is then concentrated using a rotovap. The residue is diluted with MeOH (75 mL) and a solution of 2M NH$_3$ in MeOH (10.0 mL, 20.0 mmol) is added followed by formic acid (0.77 mL, 20.0 mmol), 3 Å molecular sieves and finally NaCNBH$_3$ (1.57 g, 25.0 mmol). The mixture is stirred overnight at room temperature. The solvent was evaporated using a rotovap. The residue is dissolved in EtOAc and washed with 10% Na$_2$CO$_3$, then dried over Na$_2$SO$_4$. After filtration, the solvent is evaporated and the product purified by flash chromatography (step gradient 20-40% EtOAc in hexane) to give 2,3,4,6-tetrabenzyl-1-deoxynnorjirimycin.

1-Deoxynorjirimycin Hydrochloride (Compound 1)

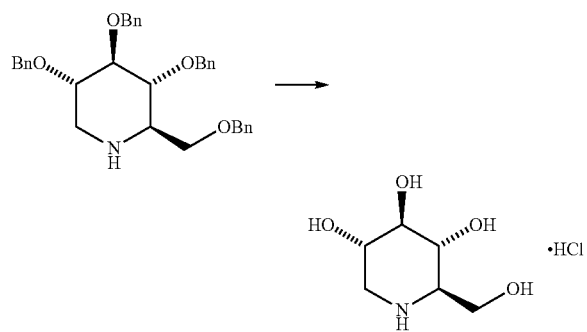

A solution of 2,3,4,6-tetrabenzyl-1-deoxynnorjirimycin (5.0 g, 9.5 mmol) in EtOH (100 mL) is stirred with 5N HCl in 2-PrOH (3.0 mL, 15.0 mmol) and then evaporated using a rotovap. The residue is dissolved in EtOH and evaporated again using a rotovap. The residue is dissolved in EtOH (150 mL) and hydrogenated (50 psi) over 0.5 g Pd(OH)$_2$ overnight at room temperature. The catalyst is removed by filtration and the filter cake washed with EtOH/H$_2$O and then finally EtOH. The filtrate is evaporated on a rotovap and then co-evaporated with EtOH to give a white solid. The solid is triturated with EtOH and filtered to give a white solid. Recrystallization from EtOH/H$_2$O gives the title compound as a white solid. MP 212-215° C., MH$^+$=164.

N-(2-hydroxyethyl)-1-deoxynojirimycin dimethyl carbamate (Compound 15)

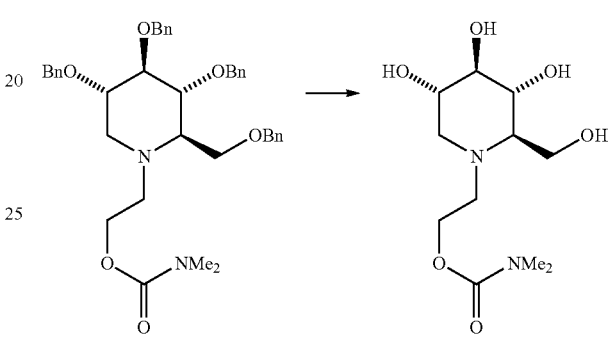

N-(2-hydroxyethyl)-tetra-O-benzyl-1-deoxynojirimycin dimethyl carbamate (0.63 g, 0.99 mmol) is dissolved in 50 ml of methanol and is treated with 130 microliters of concentrated hydrochloric acid (1.6 mmol) and 20% palladium hydroxide (0.2 g, 0.3 mmol) as catalyst. The heterogeneous reaction mixture is placed under an atmosphere of hydrogen and stirred for 15 h. The catalyst is removed by filtration through Celite which is washed with additional methanol. The filtrate is concentrated using a rotovap and the crude product is purified using flash silica-gel chromatography eluting with chloroform:methanol (4:1). The appropriate fractions are concentrated using a rotovap and then are lyophilized from water to give the N-(2-hydroxyethyl)-1-deoxynojirimycin dimethyl carbamate derivative (V, Compound 14) (MS=279.4, M+H).

N-(2-(2,2,2-Trifluorethoxyethyl)-1-deoxynojirimycin (Compound 19)

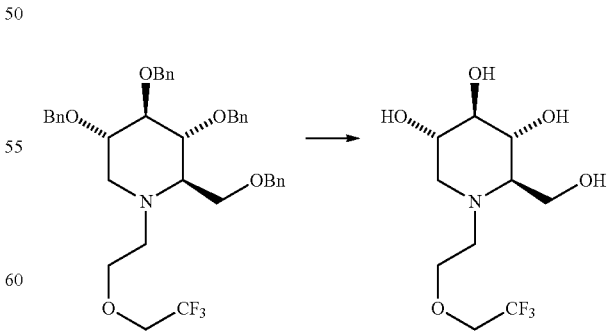

Trifluoroethyl ether intermediate (IX) (0.40 g, 0.62 mmol) is dissolved in 150 ml of methanol and treated with 130 microliters of concentrated hydrochloric acid (1.6 mmol) and 20% palladium hydroxide (0.2 g, 0.3 mmol). The heterogeneous reaction mixture is placed under an atmosphere of hydrogen and pressurized to 40 psi using a Parr shaker. After 32 h the catalyst wi removed by filtration through Celite which is washed with additional methanol. The filtrate is concentrated using a rotovap and the crude product is purified using flash silica-gel chromatography eluting with chloroform:methanol (4:1). The appropriate fractions are concentrated using a rotovap and then lyophilized from water to give N-(2-(2,2,2-Trifluorethoxyethyl)-1-deoxynojirimycin as a yellow foam (MS=290.2, M+H).

N-(Methoxyethyl) DNJ (Compound 20)

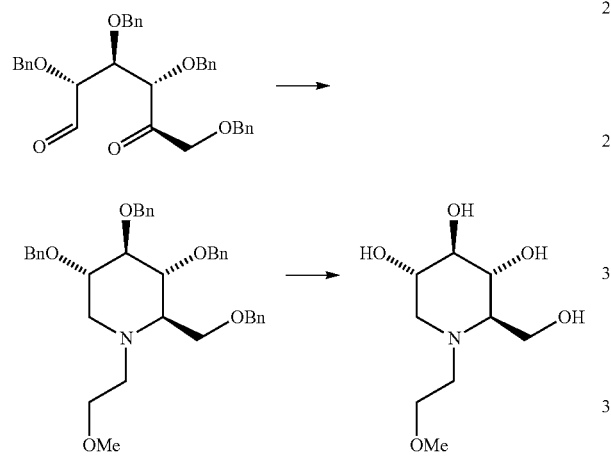

General iminosugar prep-1 is used except 2-methoxyethyl amine is used in place of NH$_3$ to give the title compound. MS (ES+): 222 [M+1].

N-(Ethoxyethyl) DNJ (Compound 21)

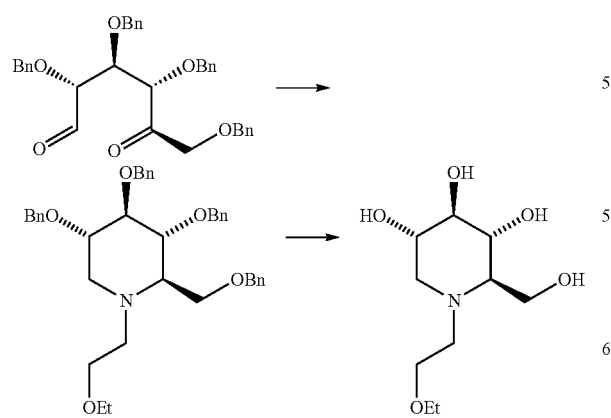

General iminosugar prep-1 is used except 2-ethoxyethyl amine is used in place of NH$_3$ to give the title compound. MS (ES+): 258 [M+Na].

N—R-(−)-Tetrahydrofuryanylmethyl-1-deoxynojirimycin (Compound 17)

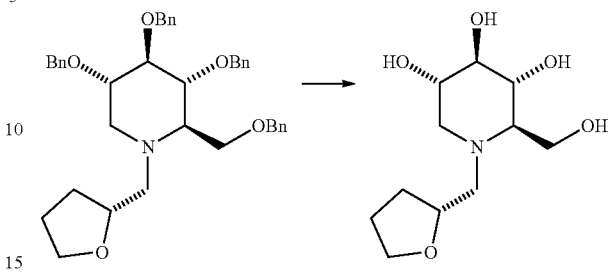

Tetrahydrofuryanylmethyl-tetra-O-benzyl-1-deoxynojirimycin is debenzylated using palladium hydroxide in ethanol under a hydrogen atmosphere at 60 psi with warming to 60 C. The crude product is purified using flash silica-gel chromatography eluting with a mixture of chloroform:methanol:ammonium hydroxide (80:20:2) to give the free base of title compound as a white foam. The purified free base is then converted to the hydrochloride salt by treatment with 1.0 equivalent of anhydrous hydrochloric acid in 2-propanol. The solvent is removed by evaporation using a rotovap to give the desired hydrochloride salt as a white solid (MS=248.2, M+H).

N—S-(+)-Tetrahydrofuryanylmethyl-1-deoxynojirimycin (Compound 18)

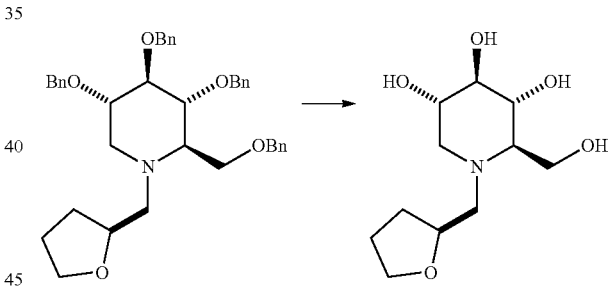

N—S-(+)-Tetrahydrofuryanylmethyl-tetra-O-benzyl-1-deoxynojirimycin is debenzylated using palladium hydroxide in methanol under a hydrogen atmosphere at 60 psi with warming to 60 C. The crude product is purified using flash silica-gel chromatography eluting with a mixture of chloroform:methanol:ammonium hydroxide (80:20:2) to give the title compound as a white foam (MS=248.2, M+H).

N-Ethyl-DNJ (Compound 3) [General Iminosugar Prep-2]

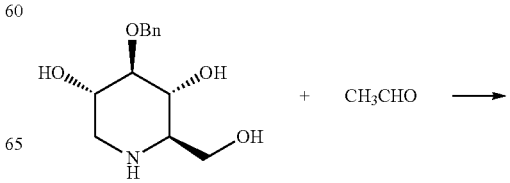

-continued

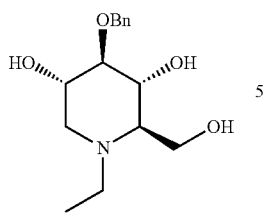

A mixture of 1-DNJ (1.0 g, 6.1 mmol), methanol (60 mL), DI water (3.0 mL), acetaldehyde (6.2 g, 141 mmol) and Pd black (50 mg) is rapidly stirred and hydrogenated at 20-22° C. under 60 psi pressure of $H_2$ for 20 h. The catalyst removed by filtration through a bed of Celite-545. The filtrate is evaporated using a rotovap. The non-volatile residue is applied to a flash silica gel column and eluted with a mixture comprised of methylene chloride:methanol: 29% and conc. $NH_4OH$ (70:30:5). The appropriate fractions are collected, combined, evaporated using a rotovap. Lyophilized affords the desired isolated product. MP 168.3-169.6° C., m/z 192 (ES, $[M+H]^+$).

N-Propyl-DNJ (Compound 4)

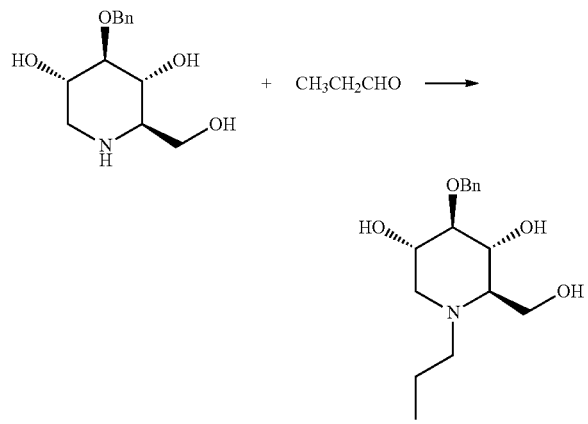

A mixture of 1-DNJ (1.0 g, 6.1 mmol), methanol (60 mL), DI water (10.0 mL), propionaldehyde (8.1, 139 mmol) and Pd black (100 mg) is rapidly stirred and is treated using similar conditions as described for the preparation of N-Ethyl-DNJ. The title compound is obtained as a white solid. MP: 56.6-57.2° C., m/z 206 (ES, $[M+H]^+$).

N-Pentyl-DNJ (Compound 6)

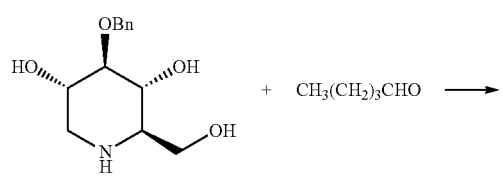

-continued

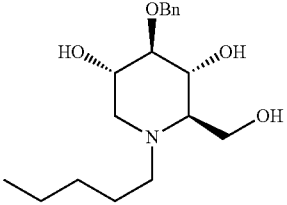

A mixture of 1-DNJ (1.0 g, 6.1 mmol), methanol (100 mL), DI water (10.0 mL), valeraldehyde (4.22 g, 49 mmol) and Pd black (100 mg) is rapidly stirred and is treated using similar conditions as described for the preparation of N-Ethyl-DNJ. The title compound is obtained as a white solid. MP 70-71° C., m/z 234 (ES, $[M+H]^+$).

N-Hexyl-DNJ (Compound 7)

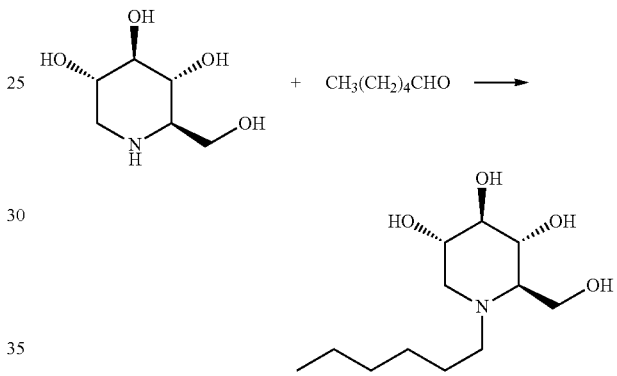

A mixture of 1-DNJ (1.0 g, 6.1 mmol), methanol (100 mL), DI water (3.0 mL), hexanal (4.3 g, 42.9 mmol) and Pd black (50 mg) is rapidly stirred and is treated using similar conditions as described for the preparation of N-Ethyl-DNJ. The title compound is obtained as a white solid. MP 64.4-65.6° C., m/z 248 (ES, $[M+H]^+$).

N-Heptyl-DNJ (Compound 8)

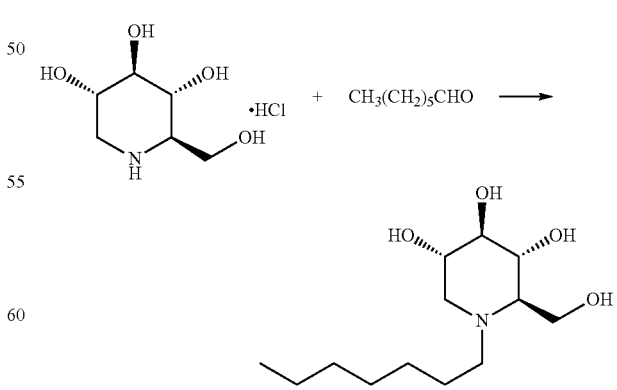

A mixture of 1-DNJ-HCl (1.0 g, 5.0 mmol), Methanol (100 mL), heptaldehyde (4.9 g, 42.9 mmol) and Pd black (50 mg) is rapidly stirred and is treated using similar conditions as described for the preparation of N-Ethyl-DNJ. The title compound is obtained as a white solid. MP 107-108° C., m/z 262 (ES, [M+H]$^+$).

N-Octyl-DNJ (Compound 9)

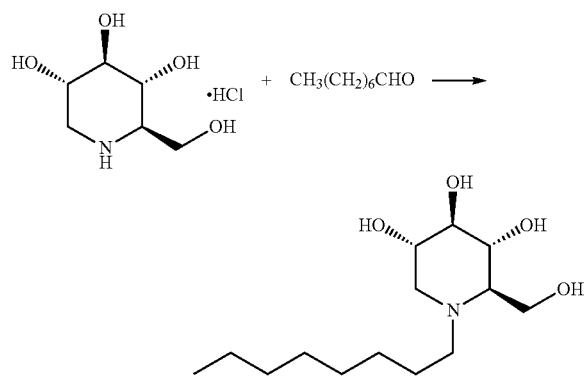

A mixture of 1-DNJ-HCl (1.0 g, 5.0 mmol), methanol (100 mL), octyl aldehyde (4.9 g, 42.9 mmol) and Pd black (50 mg) is rapidly stirred and is treated using similar conditions as described for the preparation of N-Ethyl-DNJ. The title compound is obtained as a white solid. MP 193-195° C., m/z 276 (ES, [M+H]$^+$).

N-((Benzofuran-2-yl)methyl)deoxynorjirimycin (Compound 30)

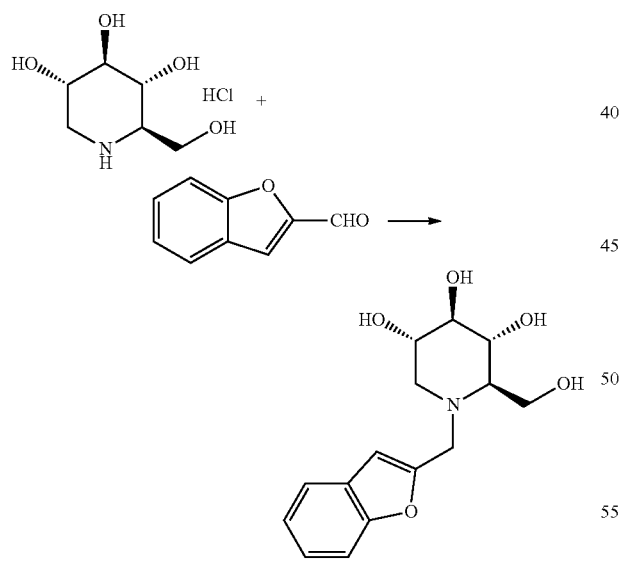

A suspension of deoxynorjirimycin hydrochloride (0.5 g, 2.5 mmol) in EtOH (30 mL) is treated with benzofuran-2-carboxaldehyde (0.55 g, 3.75 mmol), HOAc (0.15 mL, 3.75 mmol) and sodium cyanoborohydride (0.23 g, 3.75 mmol). The mixture is stirred for 24-36 hrs at room temperature. The solvent is evaporated using a rotovap and the residue is dissolved in a mixture of 9/1 MeOH/NH$_4$OH and evaporated onto silica. Purification is accomplished using flash chromatography with a gradient from 0 to 20% (9/1 MeOH/ NH$_4$OH) in CHCl$_3$. The appropriate fractions are combined and the solvent is evaporated to give the title compound as a white solid mp 169-175° C. MH$^+$=294.

N-((Benzothiophen-3-yl)methyl)deoxynorjirimycin (Compound 31)

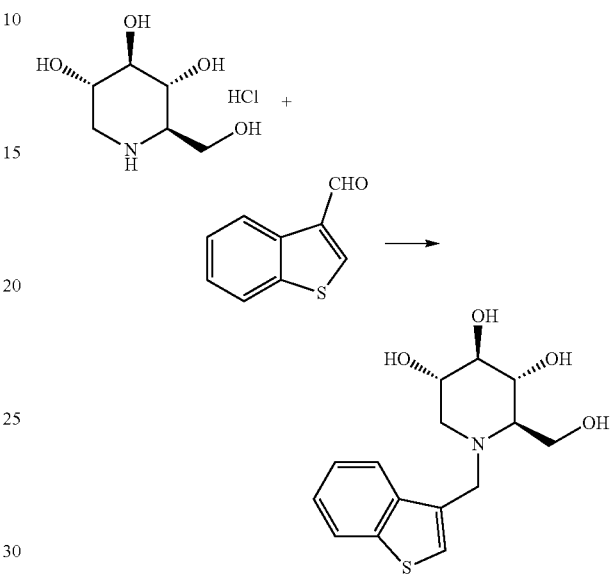

The method described for the compound directly above was used except benzothiophene-3-carboxaldehyde was used in place of benzofuran-2-carboxaldehyde to give the title compound as a white solid mp 145-149° C. MH$^+$=310.

N-((Furan-2-yl)methyl)deoxynorjirimycin (Compound 29)

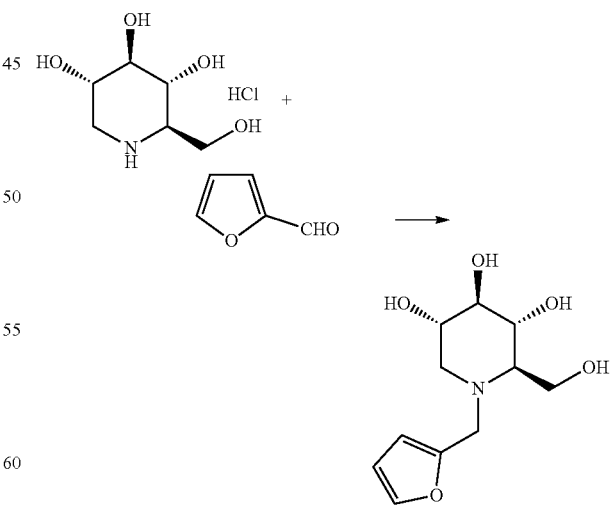

The method described for the compound above was used except furfural was used in place of benzofuran-2-carboxaldehyde to give the title compound as a colorless oil. MH$^+$=244.

N-((1,4-Benzodioxan-6-yl)methyl)deoxynorjirimycin (Compound 28)

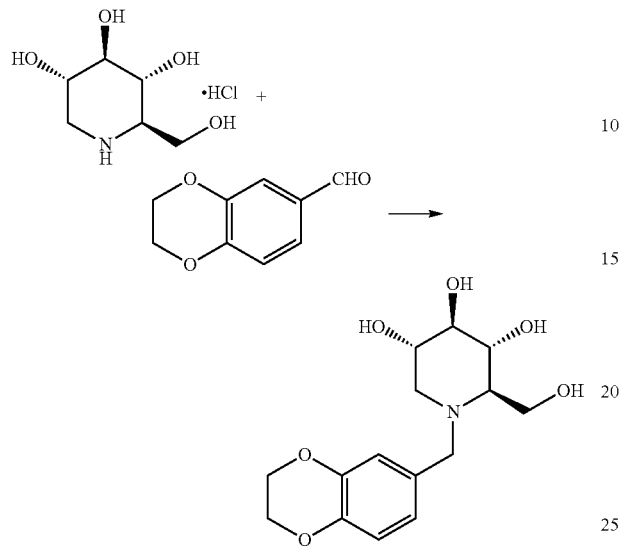

The method described above was used except 1,4-benzodioxane-6-carboxaldehyde was used in place of benzofuran-2-carboxaldehyde to give the title compound as an amorphous solid MH+=312.

N-Cyclopropylmethyl-1-deoxynojirimycin (Compound 11)

General Iminosugar Prep-3

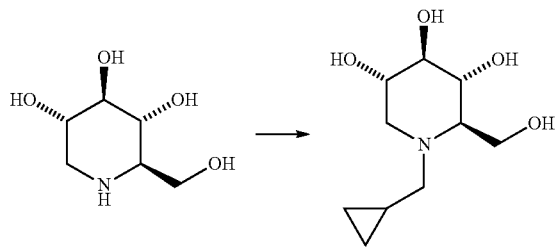 [SMILES: OC[C@H]1NC[C@H](O)[C@@H](O)[C@@H]1O ; OC[C@@H]1[C@@H](O)[C@H](O)[C@@H](O)CN1CC1CC1]

1-Deoxynojirimycin (Toronto Research Chemicals, Cat. No. D245000, 3.0 g, 18.4 mmol) dissolved in 300 ml of anhydrous methanol and is combined with cyclopropane carboxaldehyde (Aldrich, 2.5 ml, 33.1 mmol). 3 Angstrom molecular sieves (6.0 g) are added and the mixture is stirred for 15 min. MP-Cyanoborohydride (Argonaut Technologies, 19.2 g, 46.0 mmol) is added followed by glacial acetic acid (1.1 ml, 18.4 mmol). The reaction mixture is warmed to 45 C for 48 h. The solution is concentrated using a rotovap and the crude product purified using flash silica-gel chromatography eluting first with chloroform then with 5:1 chloroform:methanol/ammonium hydroxide (10/1), then 3:1 chloroform:methanol/ammonium hydroxide (10/1) and finally 1:1 chloroform:methanol/ammonium hydroxide (10/1). Upon concentration of the appropriate fractions using a rotovap, compound the title compound is isolated as a white foam (MS=218.8, M+H).

4-Trifluoromethyl(benzyl)-DNJ (Compound 23) and

Alpha-cyano-4-Trifluoromethyl(benzyl)-DNJ (Compound 24)

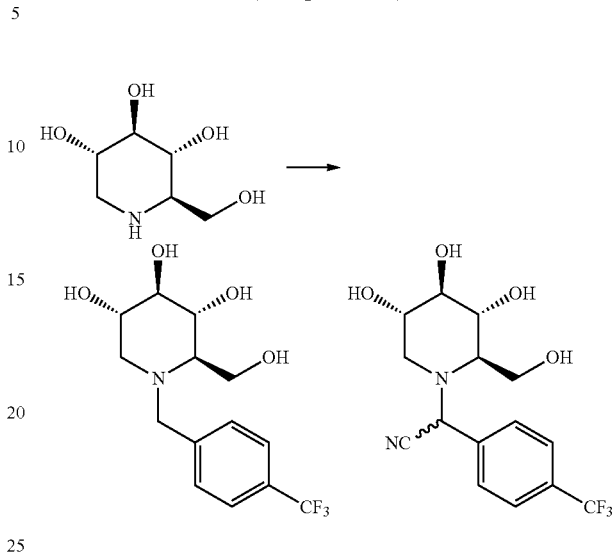

Using general iminosugar prep-3, 1-deoxynojirimycin (300 mg, 1.839 mmol), 4-trifluoromethylbenzaldehyde (Aldrich, 576.2 mg, 3.309 mmol), MP-cyanoborohydride (Argonaut Technologies, 1.92 g, 4.596 mmol), acetic acid (110.4 mg, 1.839 mmol) are combined and stirred as described in the general procedure. Purification is accomplished using flash silica-gel chromatography eluting first with chloroform then 10:1 chloroform:methanol/ammonium hydroxide (10:1), then 8:1 chloroform:methanol/ammonium hydroxide (10:1), then 6:1 chloroform:methanol/ammonium hydroxide (10:1), then 4:1 chloroform:methanol/ammonium hydroxide (10:1) to give 4-Trifluoromethyl(benzyl)-DNJ as a white solid (MS=322, M+H) and alpha-cyano-4-Trifluoromethyl(benzyl)-DNJ as a white solid (MS=347, M+H).

4-Trifluoromethoxy(benzyl)-DNJ (Compound 25)

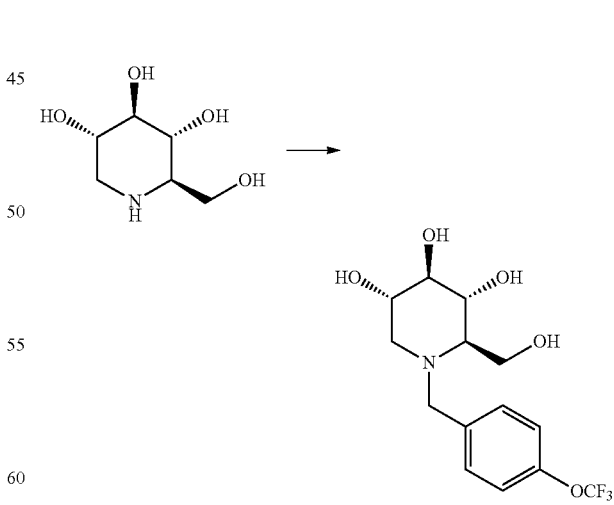

Using general iminosugar prep-3, 1-deoxynojirimycin (300 mg, 1.839 mmol), 4-trifluoromethoxylbenzaldehyde (Aldrich, 629.2 mg, 3.309 mmol), MP-cyanoborohydride (Argonaut Technologies, 1.92 g, 4.596 mmol), acetic acid (110.4 mg, 1.839 mmol) are combined and stirred as described in the general procedure. Purification is accomplished using flash silica-gel chromatography, eluting first with chloroform then 10:1 chloroform:methanol/ammonium hydroxide (10:1), then 8:1 chloroform:methanol/ammonium hydroxide (10:1), then 6:1 chloroform:methanol/ammonium hydroxide (10:1), then 4:1 chloroform:methanol/ammonium hydroxide (10:1) to give the title compound as a white solid (MS=338, M+H, MP 101-103° C.).

4-n-Butoxy(benzyl)-DNJ (Compound 27)

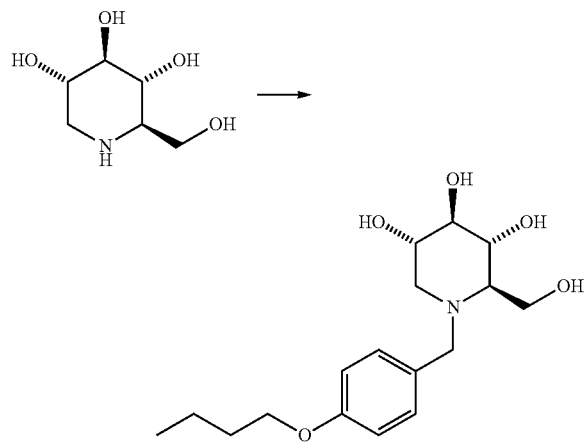

Using general iminosugar prep-3, 1-deoxynojirimycin (1.0 g, 6.1 mmol), 4-butoxybenzaldehyde (Aldrich, 2.0 g 11.2 mmol), MP-cyanoborohydride (Argonaut Technologies, 6.4 g, 15.3 mmol), acetic acid (0.37 ml, 6.4 mmol) are combined and stirred as described in the general procedure. Purification is accomplished using flash silica-gel chromatography, eluting first with chloroform then 10:1 chloroform:methanol/ammonium hydroxide (10:1), then 8:1 chloroform:methanol/ammonium hydroxide (10:1), then 6:1 chloroform:methanol/ammonium hydroxide (10:1), then 4:1 chloroform:methanol/ammonium hydroxide (10:1) to give the title compound as a white solid (MP 153-155° C.).

4-n-Pentoxy(benzyl)-DNJ (Compound 26)

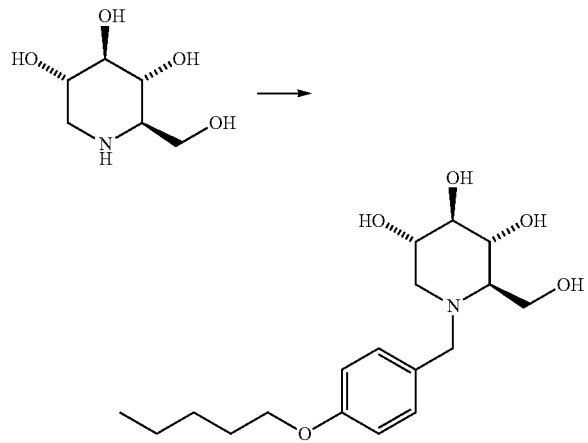

Using general iminosugar prep-3, 1-deoxynojirimycin (1.0 g, 6.1 mmol), 4-butoxybenzaldehyde (Alfa Aesar, 2.2 g 11.2 mmol), MP-cyanoborohydride (Argonaut Technologies, 6.4 g, 15.3 mmol), acetic acid (0.37 ml, 6.4 mmol) are combined and stirred as described in the general procedure. Purification is accomplished using flash silica-gel chromatography, eluting first with chloroform then 10:1 chloroform:methanol/ammonium hydroxide (10:1), then 8:1 chloroform:methanol/ammonium hydroxide (10:1), then 6:1 chloroform:methanol/ammonium hydroxide (10:1), then 4:1 chloroform:methanol/ammonium hydroxide (10:1) to give the title compound as a white solid (MS=340, M+H; MP 155-157° C.).

N-(1-(tert-butoxycarbonyl)-4-piperidinylmethyl)-1-deoxynojirimycin (Compound 16)

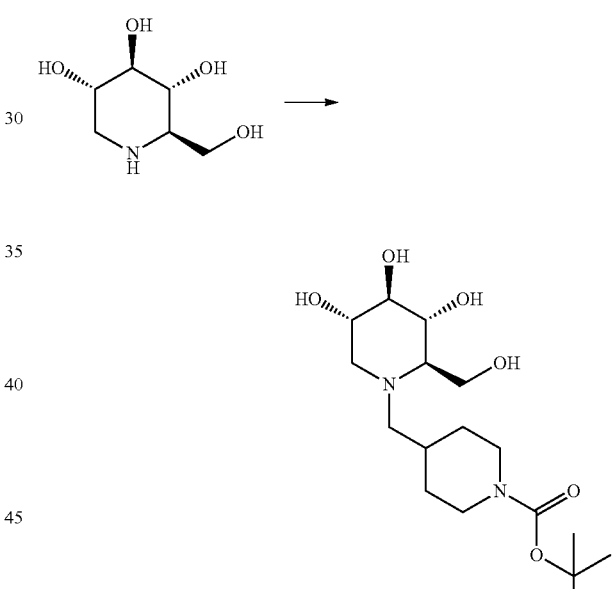

Using general iminosugar prep-3, 1-deoxynojirimycin (500 mg, 3.064 mmol), 1-(tert-butoxycarbonyl)-4-piperidinecarboxaldehyde (CNH Technologies, 1.18 g, 5.516 mmol), MP-cyanoborohydride (Argonaut Technologies, 3.19 g, 4.596 mmol), acetic acid (184 mg, 3.064 mmol) are combined and stirred as described in the general procedure. Purification is accomplished using flash silica-gel chromatography eluting first with chloroform then 10:1 chloroform:methanol/ammonium hydroxide (10:1) to give N-(1-(tert-butoxycarbonyl)-4-piperidinylmethyl)-1-deoxynojirimycin as an off white solid (MS=361, M+H, MP 46-50° C.).

N-Cyclopentylmethyl-1-deoxynojirimycin (Compound 12)

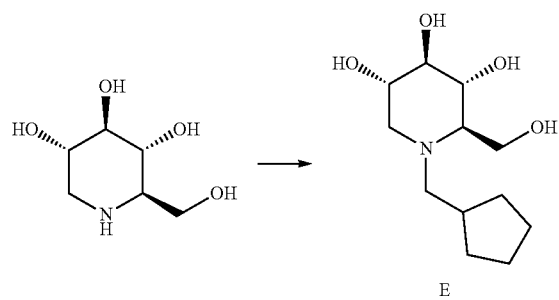 [SMILES: OC[C@H]1NC[C@H](O)[C@@H](O)[C@@H]1O ; OC[C@@H]1[C@@H](O)[C@H](O)[C@@H](O)CN1CC1CCCC1]

E

Using general iminosugar prep-3, 1-deoxynojirimycin (500 mg, 3.064 mmol), cyclopentanecarboxaldehyde (Aldrich, 541 mg, 5.516 mmol), MP-cyanoborohydride (Argonaut Technologies, 3.19 g, 7.661 mmol), acetic acid (184 mg, 3.064 mmol) are combined and stirred as described in the general procedure. Purification is accomplished using flash silica-gel chromatography eluting first with chloroform 8:1 chloroform:methanol/ammonium hydroxide (10:1), then 4:1 chloroform:methanol/ammonium hydroxide (10:1) to provide N-Cyclopentylmethyl-1-deoxynojirimycin as a viscous tan oil (MS=246, M+H).

C-1-α-Nonyl-1-deoxynojirimycin and C-1-j-Nonyl-1-deoxynojirimycin (Compound 32) [General Iminosugar Prep-4]

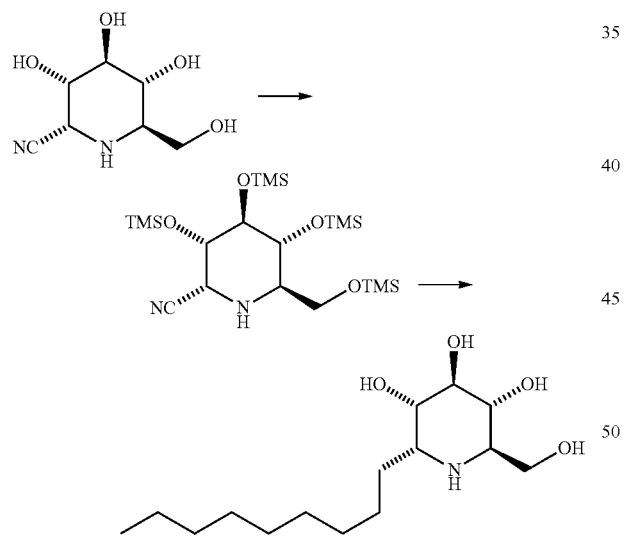

Using a analogous procedure as that described by Boshagen, Geiger and Junge (*Angewante Chemie*, Int. Ed. Engl., 20(9), 806-807 (1981). 1-α-Cyano-1-deoxynojirimycin is prepared according to the method of Marcuccio (WO00/56713) (1.0 g, 5.3 mmol) and is suspended in hexamethyldisilazane (11 mL). The suspension is treated with imidazole (156.3 mg, 2.5 mmol) and heated to 60° C. for 5 h under an Argon atmosphere. The mixture is filtered to remove the solids and the filtrate is concentrated using a rotovap at 55-60° C. The residue is dissolved in dry THF (50 mL) and a solution of n-nonylmagnesiumbromide (1M in ether, 31.9 mmol, 38 mL) is added at 15-20° C. The mixture is warmed to room temperature and stirred for 5 h. The mixture is cooled in ice-bath and stirred with 1N HCl (30 mL) for 3 h. The pH of the mixture is adjusted to 8.0 by adding 2N NaOH. The organic layer is removed and the aqueous phase is lyophilized. The residue is dissolved in methanol (50 mL) and filtered to remove the solids. The filtrate is evaporated to dryness under vacuum. The residue obtained after the evaporation is chromatographed on a silica gel column using methylene chloride:methanol: 29% $NH_4OH$ (85:15:1.5). The appropriate fractions containing the β-isomer (Rf 0.5) are combined and evaporated using a rotovap and then lyophilized to obtain C-1-β-Nonyl-DNJ (MS=m/z 290).

C1-α-Butyl-DNJ (Compound 33)

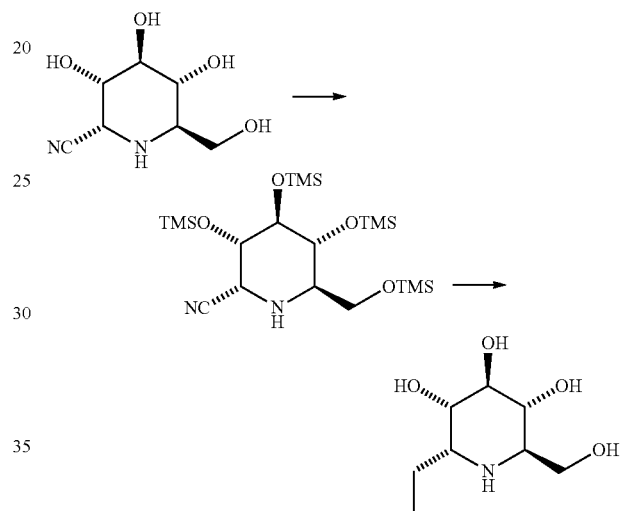

Using general iminosugar prep-4, 1-α-Cyano-1-deoxynojirimycin (2.0 g, 9.5 mmol) is converted to C-1-α-Butyl-DNJ. The product is purified by silica gel chromatography using methylene chloride:methanol:29% $NH_4OH$ in the following ratio: (85:15:1.5). The appropriate fractions, containing α-isomer (Rf 0.3), are combined and evaporated to remove the solvent and the lyophilized to obtain the title compound (MS=m/z 220).

C1-α-Benzyl-DNJ (Compound 35)

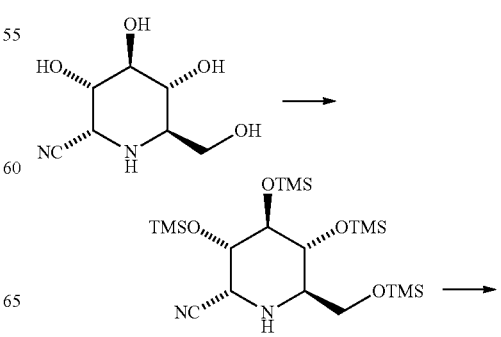

-continued

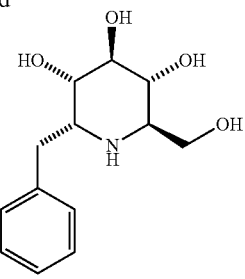

Tetra-(O-trimethylsilyl)-1-α-cyano-1-deoxynojirimycin (2.0 g, 9.448 mmol) is prepared using general iminosugar prep-4. The protected compound is dissolved in dry THF (20 mL) and benzylmagnesiumbromide (2.0M in THF, 20 mL) is added dropwise. The mixture is stirred and heated at 45° C. overnight. The mixture is cooled to room temperature, 2N HCl (30 mL) is added, and the mixture is stirred for 3 h. The solvent is evaporated using a rotovap and the residue is treated with a solution of 29% $NH_4OH$ to neutralize the acid. The solution is washed with ether (2×20 mL) and the aqueous phase is separated and lyophilized. The solid is stirred with methylene chloride:methanol: 29% $NH_4OH$ (80:20:4), filtered and the filtrate is evaporated using a rotovap. The residue is chromatographed on a silica gel column using methylene chloride:methanol: 29% $NH_4OH$ (80:20:4). The appropriate fractions containing α-isomer (Rf 0.3) are combined and evaporated using a rotovap and then lyophilized to obtain the title compound (MP=73-74° C., MS=m/z 254). $^1$H-NMR, 300 MHz (D2O) 2.28 (m, 2H), 2.55 (ddd, 1H, J=2.8, 5.6.10 Hz), 2.99 (m, 2H), 3.06 (dd, 1H, J=2.8, 13.6 Hz), 3.11 (m, 1H), 3.22 (dd, 1H, J=7.6, 11.2 Hz), 3.56 (dd, 1H, J=3.2, 11.6 Hz), and 7.2 (m, 5H).

Example 2: Enhancement of Gaa with DNJ and DNJ Derivatives

Experiments described below indicate that DNJ and DNJ derivative N-butyl-DNJ, known inhibitors of enzymes responsible for glycolipid synthesis, also can bind to and enhance the activity of mutant Gaa without inhibiting glycolipid synthesis.

Methods

Cell Culture and Seeding.

The PM11 (P545L), PM8 and PM12 (both slicing defect), fibroblast cell lines was used for enhancement experiments. These cells are fibroblasts isolated from a Pompe patient. Cells were seeded at about 5000 cells per well in 180 μL media in sterile black clear-bottom 96 well Costar plates and incubated for about 3-6 hours at 37° C. with 5% $CO_2$. Media consisted of DMEM with 10% FBS and 1% penicillin/streptomycin.

Drug Treatment.

All test compounds are dissolved in 1:1 DMSO:H2O to a stock concentration of 100 mM. Serial dilutions of the cells using another sterile black clear-bottom Costar plate were performed as follows:

1. 20 μL L of 1:1 DMSO:$H_2O$ and 180 μL media were added to rows 3-11, and row 1, columns E-H for a concentration of 5% DMSO, 5% $H_2O$ in media.

2. 20 μL of 100 mM DNJ and 180 μL media were added to row 1, columns A-D for a concentration of 10 mM DNJ 3. 30 μL of each 100 mM stock solution to be tested were added to an appropriate well in row 2 along with 270 μL media for a concentration of 10 mM)

4. Row 1 was mixed up and down three times using multi-channel pipet.

5. Row 2 was mixed as above and 100 μL was transferred from row 2 to row 3. Row 3 was mixed as described above, and 100 μL was transferred to sequentially to each of rows 4 through 11 (row 12 is left blank) in order to generate serial three-fold dilutions.

4. 20 μL was transferred from serial dilution plate according to Table 1.

5. The plate was incubated at 37° C., 5% $CO_2$ for 6 days with day 1 equal to the day of dosing.

Enzyme Activity Assay.

Cells were washed two times with 200 μL dPBS followed by the addition of 70 μL of substrate (2.11 mM 3 mM 4-MU-α-D-glu) in citrate-phosphate buffer (30 mM sodium citrate, 40 mM sodium phosphate dibasic, pH 4.0), and 2.5% DMSO to rows 1-12. Following incubation at 37° C. with 5% $CO_2$ for about 3 h, 70 L of stop buffer (0.4 M glycine pH 10.8) was added to rows 1-12. The plate was read in a Victor$^2$ multilabel counter-Wallac fluorescent plate reader and the fluorescence at F460 nm was determined b at an excitation of 355 nm and emission of 460 nm using 1 second read time per well. Enzyme activity per μg of protein in the supernatant was calculated from the amount of fluorescence emitted, which is directly proportional to the amount of substrate hydrolyzed, and hence, the amount of Gaa activity in the lysate. The enhancement ratio is the Gaa activity in the presence of the DNJ derivative divided by the Gaa activity without the compound.

Results

DNJ, NB-DNJ, and N-(cyclopropyl)methyl DNJ.

As shown in FIG. 1, cells treated with DNJ (1), N-butyl-DNJ, (5) and N-(cyclopropyl)methyl DNJ (11), exhibited dose-dependent increases in Gaa activity compared to untreated control cells in the PM11 cell line. The highest concentration of DNJ, 1 mM, increases Gaa activity about 7.8-fold compared to Gaa activity in untreated cells (data not shown).

DNJ and NB-DNJ also significantly increased Gaa activity (more than 2-fold) in the PM12 cell lines at a concentration of 50 μM. No increases in Gaa activity in the PM8 cell line by DNJ were also observed (data not shown). Enhancement of Gaa by DNJ and NB-DNJ is dose-dependent, with increasing enhancement demonstrated at a range from 3.0-100 μM prior to plateau (data not shown).

Other DNJ Derivatives.

As reported in Tables 1 and 2, below, DNJ derivatives N-methyl-DNJ, N-(2-(N,N-dimethylamido)ethyloxy-DNJ (15), N-4-t-butyloxycarbonyl-piperidnylmethyl-DNJ (16), N-2-R-tetrahydrofuranylmethyl-DNJ (17), N-2-R-tetrahydrofuranylmethyl-DNJ (18), N-(2-(2,2,2-trifluoroethoxy)ethyl-DNJ (19), N-2-methoxyethyl-DNJ (20), N-2-ethoxyethyl-DNJ (21), N-4-trifluoromethylbenzyl-DNJ (23), N-alpha-cyano-4-trifluoromethylbenzyl-DNJ (24), N-4-trifluoromethoxybenzyl-DNJ (25), N-4-n-pentoxybenzyl-DNJ (26), and N-4-n-butoxybenzyl-DNJ (27) also significantly increased Gaa activity in the PM-11. Increased Gaa activity using N-methyl DNJ and N-carboxypentyl DNJ was dose dependent from about 3-100 μM (data not shown).

% $E_{max}$ refers to the percent maximal enhancement of an experimental compound relative to enhancement observed in the presence of 1 mM DNJ. It is calculated as the top of the theoretical nonlinear regression curve analyzed using GraphPad Prism version 3.02. Enhancement is defined as the average of multiple fluorescence counts normalized to the average maximum counts in the presence of 1 mM DNJ and to the minimum average counts in the absence of compound. Fluorescence counts were background subtracted. Background is defined by the average counts in the presence minus the absence of cells $EC_{50}$ (μM) refers to the concentration of compound that achieves 50% of $E_{max}$.

Without being limited to a particular mechanism, it is presumed that DNJ and the DNJ derivatives bind to mutant Gaa in the ER and induce a proper folding of the mutated protein, permitting the enzyme to exit the ER and traffic to the lysosome where it may exhibit some amount of enzymatic activity.

TABLE 1

N-ALKYL DERIVATIVES OF 1-DEOXYNOJIRIMYCIN

| Cmpd No. | Structure | Name | $EC_{50}$ (μM) | % $E_{max}$ (μM) |
|---|---|---|---|---|
| 1 | 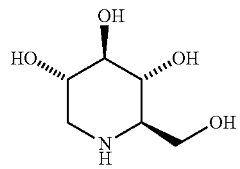 [SMILES: OC[C@H]1NC[C@H](O)[C@@H](O)[C@@H]1O] | DNJ | 98.8 ± 12.9 (n = 6) | 110.8 ± 3.5 (n = 6) |
| 2 | 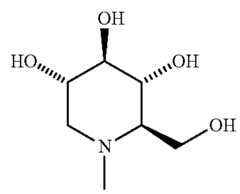 | N-Methyl-DNJ | 74.5 ± 9.5 (n = 3) | 67.3 ± 6.0 (n = 3) |
| 5 | 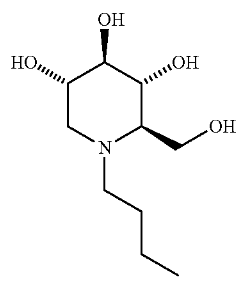 | N-Butyl-DNJ | 11.8 ± 2.2 (n = 6) | 138.9 ± 3.9 (n = 6) |
| 11 | 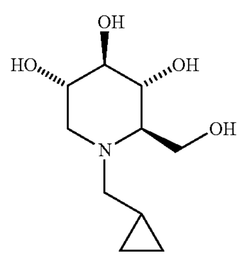 [SMILES: OC[C@@H]1[C@@H](O)[C@H](O)[C@@H](O)CN1CC1CC1] | N-(cyclopropyl)-methyl DNJ | 47.7 ± 6.5 (n = 8) | 156.3 ± 4.5 (n = 8) |
| 15 | 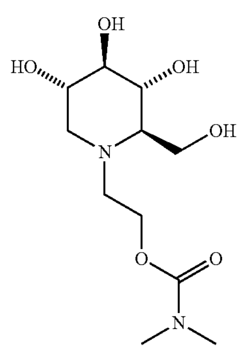 [SMILES: CN(C)C(=O)OCCN1C[C@H](O)[C@@H](O)[C@H](O)[C@H]1CO] | N-ethyloxy DNJ dimethyl carbamate/ N-(2-(N,N-dimethyl-amido)ethyloxy) DNJ | 584.1 ± 89.9 (n = 3) | 50.6 ± 3.3 (n = 3) |

TABLE 1-continued

| Cmpd No. | Structure | Name | EC$_{50}$ (μM) | % E$_{max}$ |
|---|---|---|---|---|
| 16 | 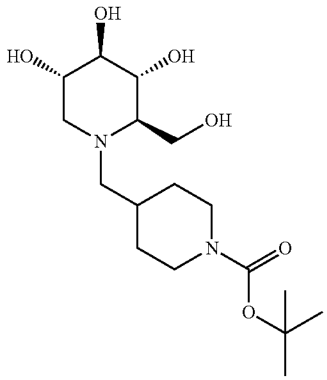 [SMILES: CC(C)(C)OC(=O)N1CCC(CN2C[C@H](O)[C@@H](O)[C@H](O)[C@H]2CO)CC1] | 4-t-BOC-Piperidinylmethyl DNJ | 69.7 ± 9.7 (n = 3) | 80.0 ± 1.9 (n = 3) |
| 17 | 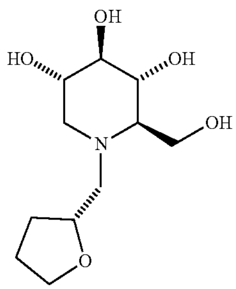 [SMILES: OC[C@@H]1[C@@H](O)[C@H](O)[C@@H](O)CN1C[C@H]1CCCO1] | N-2-(tetrahydrofuran)-methyl DNJ | 653.2 ± 93.2 (n = 3) | 100.5 ± 3.0 (n = 3) |
| 18 | 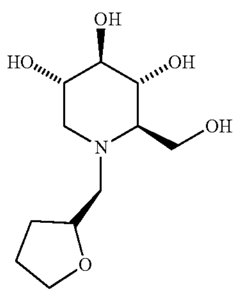 | N-2-(tetrahydrofuran)-methyl DNJ | 103.5 ± 10.9 (n = 5) | 125.1 ± 6.9 (n = 5) |
| 19 | 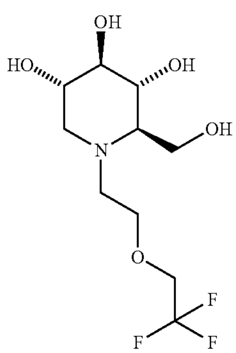 [SMILES: OC[C@@H]1[C@@H](O)[C@H](O)[C@@H](O)CN1CCOCC(F)(F)F] | N-2-oxoethyl DNJ trifluoroethy ether/ N-(2-(2,2,2-trifluoroethoxy)-ethyl DNJ | 371.8 ± 43.1 (n = 3) | 107.2 ± 12.3 (n = 3) |
| 20 | 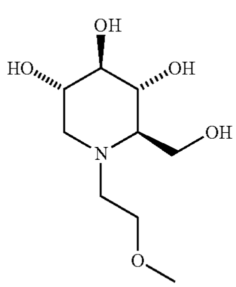 | 2-methoxyethyl DNJ | 467.7 ± 6.0 (n = 3) | 119.9 ± 10.5 (n = 3) |

TABLE 1-continued
| | | | | |
|---|---|---|---|---|
| 21 | 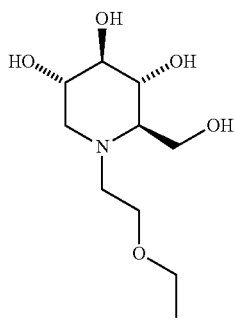 [SMILES: CCOCCN1C[C@H](O)[C@@H](O)[C@H](O)[C@H]1CO] | 2-ethoxyethyl DNJ | 209.5 ± 13.1 (n = 3) | 115.0 ± −5.7 (n = 3) |
| 23 | 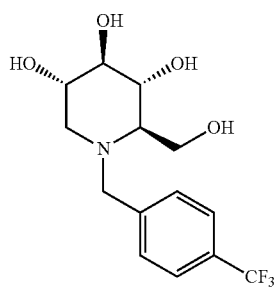 [SMILES: OC[C@@H]1[C@@H](O)[C@H](O)[C@@H](O)CN1Cc1ccc(C(F)(F)F)cc1] | 4-Trifluoromethyl-benzyl DNJ | 121.0 ± 11.4 (n = 5) | 91.6 ± 7.5 (n = 5) |
| 24 | 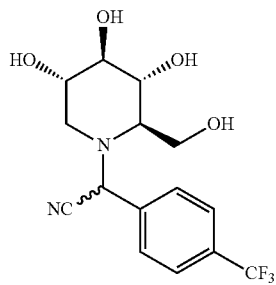 [SMILES: N#CC(c1ccc(C(F)(F)F)cc1)N1C[C@H](O)[C@@H](O)[C@H](O)[C@H]1CO] | α-cyano-4-Trifluoromethyl-benzyl DNJ | 77.1 ± 10.4 (n = 3) | 104.0 ± 6.8 (n = 3) |
| 25 | 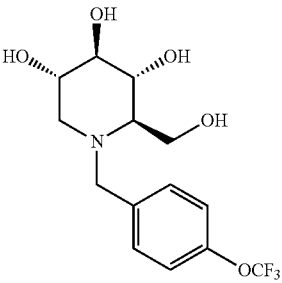 [SMILES: OC[C@@H]1[C@@H](O)[C@H](O)[C@@H](O)CN1Cc1ccc(OC(F)(F)F)cc1] | 4-Trifluoromethoxy-benzyl DNJ | 66.5 ± 6.2 (n = 3) | 100.2 ± 6.3 (n = 3) |
| 26 | 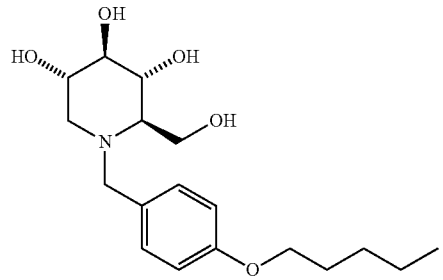 [SMILES: CCCCCOc1ccc(CN2C[C@H](O)[C@@H](O)[C@H](O)[C@H]2CO)cc1] | 4-pentoxybenzyl DNJ | 6.6 ± 0.9 (n = 3) | 47.7 ± 3.9 (n = 3) |

TABLE 1-continued

| 27 | (structure) | 4-butoxybenzyl DNJ | 17.3 ± 1.6 (n = 3) | 68.5 ± 6.9 (n = 3) |
|---|---|---|---|---|

TABLE 2

DERIVATIVES OF 1-DEOXYNOJIRIMYCIN WITH C-SUBSTITUTION

| Cmpd No. | Structure | Name | $EC_{50}$ (µM) | % $E_{max}$ (µM) |
|---|---|---|---|---|
| 32 | (structure) | α-C6-n-Nonyl-DNJ | 7.0 ± 1.8 (n = 5) | 38.9 ± 3.6 (n = 5) |
| 34 | (structure) | α-homo-DNJ | 281.0 ± 95.2 (n = 3) | 58.2 ± 2.1 (n = 3) |

Example 3: In Vivo Gaa Activity Upon Treatment with DNJ and DNJ Derivatives

Drug Administration.

This Example provides information on the effects of DNJ derivatives on mice. The DNJ derivative test compounds were administered to the mice at 0, 1 mg/kg/day; 10 mg/kg/day; and 100 mg/kg/day; organs and plasma were collected at 2 and 4 weeks after initiation of the study. Twenty male C57BL6 (25 g) mice per group were used. The drug was given in the drinking water, therefore water consumption was monitored daily.

In the control group (0 mg/kg/day), the mice were dosed daily in the drinking water (no drug) and divided into two groups. Ten animals were euthanized after 2 weeks of treatment, blood was collected from the descending aorta or vena cava, and tissues were harvested and then necroposied. After 4 weeks of treatment, the remaining 10 animals were euthanized, and subjected to the same evaluation.

In the first test group, 20 mice were dosed daily in the drinking water with an administration aim of 1 mg/kg/day (assuming a 25 g mouse has daily drinking rate of 5 mL/day then the drinking water should have a concentration of 0.025 mg/5 ml or 5 micrograms/ml). Similar to the control, 10 mice were euthanized after 2 weeks of treatment and evaluated. After 4 weeks of treatment, the remaining 10 animals will be euthanized and evaluated.

For test compounds aiming for 10 mg/kg-day, 20 mice were dosed daily in the drinking water (estimating a compound concentration of 50 micrograms/ml) and divided into two groups for testing as described for the groups above.

For test compound at aiming for 100 mg/kg-day, 20 mice were dosed daily in the drinking water (estimating a compound concentration of 500 micrograms/ml) and divided into two groups were tested as described for the groups above.

The blood samples were drawn into lithium heparin and spun for plasma. After bleeding, the heart, liver, gastrocnemius muscle, soleus muscle, tongue, kidney, and brain were removed and placed into vials. The vials were put into dry ice for rapid freezing. The tissues and plasma were then analyzed for tissue levels of Gaa and glycogen.

Tissue Preparation.

Small portions of tissue were removed and added to 500 µl lysis buffer (20 mM sodium citrate and 40 mM disodium hydrogen phosphate, pH 4.0, including 0.1% Triton X-100). Tissues were then homogenized using a microhomogenizer for a brief time, followed by centrifugation at 10,000 rpt for 10 minutes at 4° C. Supernatants were transferred to a new tube and used for the enzyme assay.

Tissue Enzyme Assay.

To 2.5 µl of supernatant (in 96-well plates) was added 17.5 µl reaction buffer (citrate phosphate buffer, no Triton), and 50 µl of 4-methyl umbelliferone (4-MU)-labeled substrate, α-glucopyranoside, or labeled negative controls, β-glucopyranoside and α-galacatopyranoside. Plates were incubated at 370 for 1 hour, followed by the addition of 70 l stop buffer (0.4 M glycine-NaOH, pH 10.6). Activity of Gaa was determined by measuring the absorbance at 460 nm by exciting at 355 nm using a 1 second read time per well (Victor2 multilabel counter-Wallac) Enzyme activity was normalized to the amount in p of lysate added, and enzyme activity per µl of lysate was estimated. The enhancement ratio is equal to the activity with the compound over the activity without the compound.

Results

As demonstrated by FIGS. 2A-D and 3A-D, Gaa levels were increased following two weeks of treatment with DNJ and N-butyl-DNJ in the brain, liver, gastrocnemius muscle, tongue (FIG. 2A-D), and also in the kidney, diaphragm, heart and soleus muscle (FIG. 3A-D). The results were significant for a linear trend. For DNJ, the increases were dose-dependent in the brain, gastrocnemius muscle, tongue, kidney, diaphragm, heart, and soleus (significant for linear trend). For N-butyl-DNJ, the increases were dose-dependent in the brain liver, gastrocnemius muscle, tongue and kidney.

After 4 weeks of treatment, Gaa activity increases were observed following treatment with DNJ in the brain, liver, gastrocnemius muscle and tongue (FIG. 4A-D), and also in the kidney, diaphragm, heart and soleus (FIG. 5A-D). Results for N-butyl DNJ were similar except for the diaphragm, heart and soleus, where increases were not observed. Increases appeared to be dose-dependent in the brain, gastrocnemius muscle, tongue, kidney (DNJ only), diaphragm (DNJ only), heart (DNJ only) and soleus (DNJ only).

These results confirm that the specific pharmacological chaperones can increase the activity of non-mutated Gaa in vivo.

Example 4: Accumulation and Localization of Gaa with and without Exposure to DNJ Derivatives In this experiment, four cell lines derived from Pompe patients who exhibited little to no residual Gaa activity were compared with wild-type fibroblasts for accumulation and localization of Gaa.

Methods

Cell Lines.

PM8, PM9, PM11, and PM12 cell lines were evaluated. PM8 harbors a splicing defect resulting in some residual Gaa activity (IVSIAS, T) G, −13); PM9 harbors a nonsense mutation on one allele (R854X) and 3 missense mutations on the other (D645E, V816I, and T9271) and has essentially no residual Gaa activity (<1%); PM11 contains a missense mutation (P545L) and has some residual Gaa activity. PM12 also has a splicing defect (IVS8+G>A/M519V).

Immunofluorescence and Microscopy.

Cells cultured for 5 days with or without were grown for 5 days on glass coverslips with NB-DNJ. Cells were fixed with 3.7% paraformaldehyde for 15 minutes, permeabilized with 0.5% saponin for 5 minutes, then labeled with a 1:300 dilution of rabbit anti-human Gaa (gift from Barry Byrne) and/or mouse monoclonal anti-LAMP1 (BD Pharmingen, catalog #555798) for 1 hour at room temperature. Secondary antibodies, goat anti-rabbit IgG conjugated with AlexaFluor 488, and goat-anti-mouse IgG conjugated with AlexaFluor 594 (Molecular Probes) were then added at a 1:500 dilution and incubated for 1 hour at room temperature. Coverslips were placed on slides with 10 µl Vectashield, sealed with fast-drying nail polish, and viewed with an 90i Nikon C1 confocal microscope.

Results

PM8.

Figures 6E, 6F, 6G, 6H:
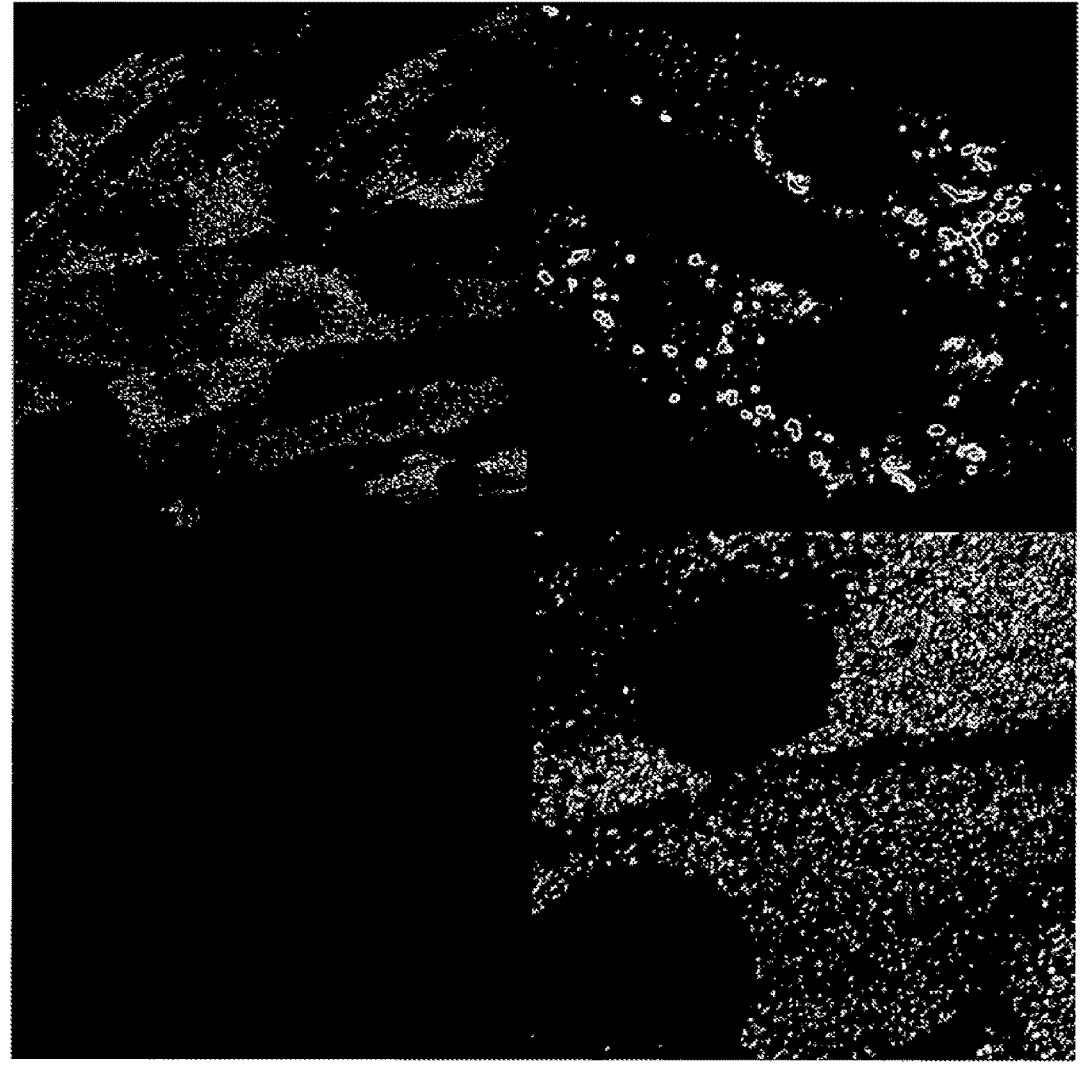

Despite having little residual Gaa activity, PM8 cells exhibited increased LAMP-1 and Gaa cytosolic staining, and had a different staining pattern, compared to wild-type fibroblasts. As shown in FIG. 6, wild-type fibroblasts treated with NB-DNJ exhibited a punctuate staining pattern for both LAMP-1 and Gaa (FIG. 6C-D), which appeared to co-localize in the lysosomes. By contrast, in the PM8 fibroblasts, staining was pervasive in the cytoplasm for both LAMP-1 and Gaa (FIGS. 6A-B and 6E-F). The overlay of both LAMP-1 and Gaa in confluent wild-type fibroblasts confirms co-localization to the lysosomes (FIG. 6H), whereas the overlay in confluent PM8 fibroblasts confirms the cytosolic excess of LAMP-1 and Gaa (FIG. 6G). The above results suggests a possible defect in lysosome formation or the presence of large aggregates of abnormally formed endosome/lysosme structures (aggresomes).

PM9.

PM9 fibroblasts also exhibited an excess of Gaa (FIGS. 7B and 7D) and LAMP-1 (FIG. 7E) staining in the cytosol (FIG. 7B). An overlay shows the formation of Gaa aggregates that resemble aggresomes (FIGS. 7A, 7C and 7F, arrows and inlay show aggresomes). It is anticipated that treatment with DNJ derivatives will restore localization of Gaa to the lysosomes, and reduce aggresome formation. It is anticipated that treatment with DNJ derivatives will restore proper localization of Gaa to the lysosomes, and reduce the presence of cytosolic aggresomes.

PM11.

PM11 fibroblasts exhibit reduced Gaa activity. When treated with NB-DNJ (50 µM) and DNJ (100 µM), the PM11 cells exhibit an increase in intensity for labeling of Gaa in lysosomes as assessed by co-labeling with lysosmal marker LAMP-1, indicating restoration of trafficking (FIG. 8). Untreated PM11 fibroblasts exhibit some Gaa staining, little of which co-localizes with LAMP-1.

In addition, to confirm that the defect in PM11 cells is trafficking of lysosmal enzymes (Gaa) to the lysosomes, wild-type fibroblasts and PM1 cells were stained for early and late endosome markers EEA1 and M6PR, respectively. There was no difference in the localization patterns for early and late endosomes between wild type fibroblasts and Pompe PM11 fibroblasts (data not shown).

PM12.

Significant increases in Gaa staining intensity was also observed in PM12 fibroblasts treated with NB-DNJ (data not shown).

DISCUSSION

This example demonstrates that the pharmacological chaperones of the present invention can restore the phenotype of cells harboring mutations in Gaa other than (and in addition to) those mutations which cause Gaa to become unstable and fail to exit the ER during synthesis.

This supports a hypothesis where improving the trafficking of mutant Gaa from the ER to the lysosome may be sufficient to ameliorate some pathogenic effects of Pompe disease in tissues such as muscle, even without restoring Gaa hydrolase activity in the lysosome. It is clear that glycogen turnover is not enough to improve the patient phenotype in Pompe disease. Thus, one hypothesis for why improvements in trafficking may improve Pompe pathology is that lack of Gaa activity causes a glucose deficiency in cells, which may trigger or perpetuate an autophagic response (to use cytoplasmic glycogen for quick release of glucose). This autophagic response impairs trafficking through the endosomal trafficking pathways, resulting in the mistrafficking of membrane stabilizing proteins, and the ultimate breakdown of muscle fibers.

Chaperone therapy may rescue Gaa activity, alleviate the glucose deficiency and autophagic response induced by the glucose deficiency, and ultimately restore trafficking of membrane stabilizing proteins to prevent further muscle damage.

Example 5: Effect of DNJ Derivatives on Intestinal Gaa: Counterscreening

The ideal specific pharmacological chaperone, at sub-inhibitory concentrations, will enhance lysosomal Gaa without inhibiting intestinal Gaa. Accordingly, intestinal Gaa activity was evaluated in crude extracts from the mouse intestine at a pH of 7.0. In addition, an intestinal Gaa enzyme inhibition assay was established to determine whether compounds such as DNJ and NB-DNJ exerted an inhibitory effect on intestinal Gaa.

Methods

Tissue Preparation.

Crude extracts were prepared from mouse intestines from C57BK6 mice as described above. Supernatants were transferred to a new tube and used for the enzyme assay.

Results

DNJ was a more potent inhibitor of intestinal Gaa with an $IC_{50}$ value of 1 μM, while NB-DNJ had an $IC_{50}$ inhibitory value of 21 μM (data not shown).

Example 6: Treatment of Pompe Patients with DNJ Derivatives

In view of the results above, treatment of Pompe patients with the DNJ and DNJ derivatives of the present invention will reduce the pathologic accumulation of glycogen in muscle tissue, thereby ameliorating the disease state. In view of the fact that the currently approved sole treatment for Pompe disease, ERT, is ineffective in reducing glycogen accumulation in skeletal muscle since the recombinant enzyme cannot penetrate muscle tissue, this method solves a long-felt need in the art.

Methods

Patient Population.

Patients with diagnosed infantile, juvenile and/or adult-onset Pompe disease will be recruited and evaluated in a randomized, double-blind, multiple-dose, open-label trial of orally administered DNJ derivative. In order to qualify, patients must have at least of the following: a) cardiomyopathy, defined as a left ventricular mass index (LVMI) determined by cross-sectional echocardiography; b) a requirement for invasive or non-invasive ventilatory support, where non-invasive ventilation is defined as any form of ventilatory support applied without the use of an endotracheal tube; or c) severe motor delay, defined as failure to perform gross motor skills achieved by 90% of normal aged peers on the Denver Developmental Screening Test (DDST-2; Hallioglo et al., *Pediatr Int.* 2001; 43(4):400-4).

Drug Administration.

Two groups of 10 subjects will receive either 50 or 100 mg of DNJ or a DNJ derivative twice a day for 24 weeks. This is below the amount indicated for substrate deprivation of glycosphingolipids in Gaucher disease.

Endpoints.

Clinical efficacy will be evaluated by ventilator-free survival, left ventricular mass index, motor development and skeletal muscle function e.g., as measured using the Denver Developmental Screening Test and the Alberta Infant Motor Scale (Piper et al., *Motor Assessment of the Developing Infant*. Philadelphia, Pa., W.B. Saunders Co., 1994), the Bayley Scales of Infant Development II (BSIDII; Bayley et al., *Bayley Scores of Infant Development*. $2^{nd}$ Ed., San Antonio, Tex.: Harcourt Brace & Co. 1993), as well as histologic and biochemical analysis of muscle biopsies, i.e., a determination of glycogen levels in treated versus untreated patients using periodic acid-Schiff (PAS)-positive staining and enzyme activity assays, and measurement of Gaa activity in fibroblasts obtained from the patients. Clinical measurements will be assessed bi-weekly, except for muscle biopsies which will be assessed at 4, 12 and 24 weeks.

Results

Treatment with a DNJ derivative will be effective for the treatment of Pompe disease by ameliorating some of the symptoms and reducing the muscle tissue levels of glycogen. For example, it is expected that within 12 weeks, increases in Gaa activity in muscle will be observed, and that the accumulation of glycogen in muscle will be reduced. In addition, it is expected that LVMI will be reduced and respiratory symptoms will improve. Lastly, progress in motor development and muscle tone, especially in young patients, is expected.

CONCLUSION

The method of the invention provides an unexpected benefit in the treatment of Pompe disease, for which the only current treatment is ERT. Administration of a small molecule chaperone, preferably orally, is cost-effective and permits rescue of the enzyme in tissues impenetrable to ERT, i.e., the brain. In addition, combination therapy with the chaperone compound and replacement protein may reduce the number of infusions and/or amount of recombinant or purified enzyme required, thereby reducing costs and providing a benefit to patients. Lastly, formulation of replacement Gaa in combination with a chaperone compound of the invention may stabilize the recombinant enzyme and prevent aggregation and/or degradation, thereby increasing the shelf-life of the enzyme.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, accession numbers, and protocols are cited throughout this application, the disclosures of which are incorporated herein by reference in their entireties for all purposes.

What is claimed is:

1. A method of stabilizing acid-alpha glucosidase (Gaa) in a patient in need thereof, comprising administering to the patient an effective amount of N-butyldeoxynojirimycin (NB-DNJ) or a pharmaceutically acceptable salt thereof in combination with Gaa, wherein the Gaa is administered at a dose of from 10 mg/kg to 20 mg/kg, wherein the NB-DNJ or the pharmaceutically acceptable salt thereof is administered at a dose of from 1 mg to 300 mg per day, and wherein upon administration the NB-DNJ or pharmaceutically acceptable salt thereof stabilizes the Gaa.

2. The method of claim 1, wherein the Gaa is administered at dose of 20 mg/kg.

3. The method of claim 1, wherein the NB-DNJ or pharmaceutically acceptable salt thereof is administered in an oral dosage form.

4. The method of claim 3, wherein the oral dosage form is a tablet or a capsule.

5. The method of claim 1, wherein the NB-DNJ or pharmaceutically acceptable salt thereof and the Gaa are administered by different routes.

6. The method of claim 5, wherein the NB-DNJ or pharmaceutically acceptable salt thereof is administered orally and the Gaa is administered intravenously.

7. The method of claim 1, wherein the NB-DNJ or pharmaceutically acceptable salt thereof is administered from 0 to 6 hours prior to the administration of Gaa.

8. The method of claim 1, wherein the ratio of Gaa activity in the presence of the NB-DNJ or pharmaceutically acceptable salt thereof over Gaa activity without the NB-DNJ or pharmaceutically acceptable salt thereof is at least 1.5-fold.

9. The method of claim 1, wherein the ratio of Gaa activity in the presence of the NB-DNJ or pharmaceutically acceptable salt thereof over Gaa activity without the NB-DNJ or pharmaceutically acceptable salt thereof is at least 5-fold.

10. The method of claim 1, wherein the patient has Pompe disease.

* * * * *

SEQUENCE LISTING

<160> NUMBER OF SEQ ID NOS: 2

<210> SEQ ID NO 1
<211> LENGTH: 3624
<212> TYPE: DNA
<213> ORGANISM: Homo sapiens

<400> SEQUENCE: 1

| | | | | | | |
|---|---|---|---|---|---|---|
| cagttgggaa | agctgaggtt | gtcgccgggg | ccgcgggtgg | aggtcgggga | tgaggcagca | 60 |
| ggtaggacag | tgacctcggt | gacgcgaagg | accccggcca | cctctaggtt | ctcctcgtcc | 120 |
| gcccgttgtt | cagcgaggga | ggctctgggc | ctgccgcagc | tgacgggaa | actgaggcac | 180 |
| ggagcgggcc | tgtaggagct | gtccaggcca | tctccaacca | tgggagtgag | gcacccgccc | 240 |
| tgctcccacc | ggctcctggc | cgtctgcgcc | ctcgtgtcct | tggcaaccgc | tgcactcctg | 300 |
| gggcacatcc | tactccatga | tttcctgctg | gttccccgag | agctgagtgg | ctcctcccca | 360 |
| gtcctggagg | agactcaccc | agctcaccag | cagggagcca | gcagaccagg | gccccgggat | 420 |
| gcccaggcac | accccggccg | tcccagagca | gtgcccacac | agtgcgacgt | ccccccccaac | 480 |
| agccgcttcg | attgcgcccc | tgacaaggcc | atcacccagg | aacagtgcga | ggcccgcggc | 540 |
| tgctgctaca | tccctgcaaa | gcaggggctg | caggagccc | agatggggca | gccctggtgc | 600 |
| ttcttcccac | ccagctaccc | cagctacaag | ctggagaacc | tgagctcctc | tgaaatgggc | 660 |
| tacacggcca | ccctgacccg | taccaccccc | accttcttcc | ccaaggacat | cctgaccctg | 720 |
| cggctggacg | tgatgatgga | gactgagaac | cgcctccact | tcacgatcaa | agatccagct | 780 |
| aacaggcgct | acgaggtgcc | cttggagacc | ccgcgtgtcc | acagccgggc | accgtcccca | 840 |
| ctctacagcg | tggagttctc | cgaggagccc | ttcggggtga | tcgtgcaccg | gcagctggac | 900 |
| ggccgcgtgc | tgctgaacac | gacggtggcg | ccctgttct | ttgcggacca | gttccttcag | 960 |
| ctgtccacct | cgctgccctc | gcagtatatc | acaggcctcg | ccgagcacct | cagtcccctg | 1020 |
| atgctcagca | ccagctggac | caggatcacc | ctgtggaacc | gggaccttgc | gcccacgccc | 1080 |
| ggtgcgaacc | tctacgggtc | tcacccttc | tacctggcgc | tggaggacgg | cgggtcggca | 1140 |
| cacgggtgt | tcctgctaaa | cagcaatgcc | atggatgtgg | tcctgcagcc | gagccctgcc | 1200 |
| cttagctgga | ggtcgacagg | tgggatcctg | gatgtctaca | tcttcctggg | cccagagccc | 1260 |
| aagagcgtgg | tgcagcagta | cctggacgtt | gtgggatacc | cgttcatgcc | gccatactgg | 1320 |
| ggcctgggct | tccacctgtg | ccgctggggc | tactcctcca | ccgctatcac | ccgccaggtg | 1380 |
| gtggagaaca | tgaccagggc | ccacttcccc | ctggacgtcc | aatggaacga | cctggactac | 1440 |
| atggactccc | ggagggactt | cacgttcaac | aaggatggct | tccgggactt | cccggccatg | 1500 |
| gtgcaggagc | tgcaccaggg | cggccggcgc | tacatgatga | tcgtggatcc | tgccatcagc | 1560 |
| agctcgggcc | ctgccgggag | ctacaggccc | tacgacgagg | tctgcggag | ggggttttc | 1620 |
| atcaccaacg | agaccggcca | gccgctgatt | gggaaggtat | ggcccgggtc | cactgccttc | 1680 |
| cccgacttca | ccaaccccac | agccctggcc | tggtgggagg | acatggtggc | tgagttccat | 1740 |
| gaccaggtgc | ccttcgacgg | catgtggatt | gacatgaacg | agccttccaa | cttcatcaga | 1800 |
| ggctctgagg | acgctgcccc | caacaatgag | ctggagaacc | cacctacgt | gcctggggtg | 1860 |
| gttgggggga | ccctccaggc | ggccaccatc | tgtgcctcca | gccaccagtt | tctctccaca | 1920 |

```
cactacaacc tgcacaacct ctacggcctg accgaagcca tcgcctccca cagggcgctg    1980
gtgaaggctc gggggacacg cccatttgtg atctcccgct cgacctttgc tggccacggc    2040
cgatacgccg gccactggac gggggacgtg tggagctcct gggagcagct cgcctcctcc    2100
gtgccagaaa tcctgcagtt taacctgctg ggggtgcctc tggtcgggc cgacgtctgc    2160 ggcttcctgg gcaacacctc agaggagctg tgtgtgcgct ggacccagct gggggccttc    2220
taccccttca tgcggaacca caacagcctg ctcagtctgc cccaggagcc gtacagcttc    2280
agcgagccgg cccagcaggc catgaggaag ccctcaccc tgcgctacgc actcctcccc    2340
cacctctaca cactgttcca ccaggcccac gtcgcggggg agaccgtggc ccggcccctc    2400
ttcctggagt tccccaagga ctctagcacc tggactgtgg accaccagct cctgtggggg    2460
gaggccctgc tcatcacccc agtgctccag gccgggaagg ccgaagtgac tggctacttc    2520
cccttgggca catggtacga cctgcagacg gtgccaatag aggcccttgg cagcctccca    2580
cccccacctg cagctccccg tgagccagcc atccacagcg aggggcagtg ggtgacgctg    2640
ccggcccccc tggacaccat caacgtccac ctccgggctg ggtacatcat ccccctgcag    2700
ggccctggcc tcacaaccac agagtcccgc cagcagccca tggccctggc tgtggccctg    2760
accaagggtg agagggcccg aggggagctg ttctgggacg atggagagag cctggaagtg    2820
ctggagcgag gggcctacac acaggtcatc ttcctggcca ggaataacac gatcgtgaat    2880
gagctggtac gtgtgaccag tgaggagct ggcctgcagc tgcagaaggt gactgtcctg    2940
ggcgtggcca cggcgcccca gcaggtcctc tccaacggtg tccctgtctc caacttcacc    3000
tacagccccg acaccaaggt cctggacatc tgtgtctcgc tgttgatggg agagcagttt    3060
ctcgtcagct ggtgttagcc gggcggagtg tgttagtctc tccagaggga ggctggttcc    3120
ccagggaagc agagcctgtg tgcgggcagc agctgtgtgc gggcctgggg gttgcatgtg    3180
tcacctggag ctgggcacta accattccaa gccgccgcat cgcttgtttc cacctcctgg    3240 gccgggctc tggccccaa cgtgtctagg agagctttct ccctagatcg cactgtgggc    3300
cggggcctgg agggctgctc tgtgttaata agattgtaag gtttgccctc ctcacctgtt    3360
gccggcatgc gggtagtatt agccaccccc tccatctgt tcccagcacc ggagaagggg    3420
gtgctcaggt ggaggtgtgg ggtatgcacc tgagctcctg cttcgcgcct gctgctctgc    3480
cccaacgcga ccgcttcccg gctgcccaga gggctggatg cctgccggtc ccgagcaag    3540 cctgggaact caggaaaatt cacaggactt gggagattct aaatcttaag tgcaattatt    3600
ttaataaaag gggcatttgg aatc                                           3624
```

<210> SEQ ID NO 2
<211> LENGTH: 952
<212> TYPE: PRT
<213> ORGANISM: Homo sapiens

<400> SEQUENCE: 2

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr

```
                65                  70                  75                  80
        Gln Cys Asp Val Pro Pro Asn Ser Arg Phe Asp Cys Ala Pro Asp Lys
                            85                  90                  95
        Ala Ile Thr Gln Glu Gln Cys Glu Ala Arg Gly Cys Cys Tyr Ile Pro
                           100                 105                 110
        Ala Lys Gln Gly Leu Gln Gly Ala Gln Met Gly Gln Pro Trp Cys Phe
                           115                 120                 125
        Phe Pro Pro Ser Tyr Pro Ser Tyr Lys Leu Glu Asn Leu Ser Ser Ser
                    130                 135                 140
        Glu Met Gly Tyr Thr Ala Thr Leu Thr Arg Thr Thr Pro Thr Phe Phe
        145                 150                 155                 160
        Pro Lys Asp Ile Leu Thr Leu Arg Leu Asp Val Met Met Glu Thr Glu
                            165                 170                 175
        Asn Arg Leu His Phe Thr Ile Lys Asp Pro Ala Asn Arg Arg Tyr Glu
                            180                 185                 190
        Val Pro Leu Glu Thr Pro Arg Val His Ser Arg Ala Pro Ser Pro Leu
                    195                 200                 205
        Tyr Ser Val Glu Phe Ser Glu Glu Pro Phe Gly Val Ile Val His Arg
        210                 215                 220
        Gln Leu Asp Gly Arg Val Leu Leu Asn Thr Thr Val Ala Pro Leu Phe
        225                 230                 235                 240
        Phe Ala Asp Gln Phe Leu Gln Leu Ser Thr Ser Leu Pro Ser Gln Tyr
                            245                 250                 255
        Ile Thr Gly Leu Ala Glu His Leu Ser Pro Leu Met Leu Ser Thr Ser
                    260                 265                 270
        Trp Thr Arg Ile Thr Leu Trp Asn Arg Asp Leu Ala Pro Thr Pro Gly
                275                 280                 285
        Ala Asn Leu Tyr Gly Ser His Pro Phe Tyr Leu Ala Leu Glu Asp Gly
                    290                 295                 300
        Gly Ser Ala His Gly Val Phe Leu Leu Asn Ser Asn Ala Met Asp Val
        305                 310                 315                 320
        Val Leu Gln Pro Ser Pro Ala Leu Ser Trp Arg Ser Thr Gly Gly Ile
                            325                 330                 335
        Leu Asp Val Tyr Ile Phe Leu Gly Pro Glu Pro Lys Ser Val Val Gln
                    340                 345                 350
        Gln Tyr Leu Asp Val Val Gly Tyr Pro Phe Met Pro Pro Tyr Trp Gly
                355                 360                 365
        Leu Gly Phe His Leu Cys Arg Trp Gly Tyr Ser Ser Thr Ala Ile Thr
                370                 375                 380
        Arg Gln Val Val Glu Asn Met Thr Arg Ala His Phe Pro Leu Asp Val
        385                 390                 395                 400
        Gln Trp Asn Asp Leu Asp Tyr Met Asp Ser Arg Arg Asp Phe Thr Phe
                            405                 410                 415
        Asn Lys Asp Gly Phe Arg Asp Phe Pro Ala Met Val Gln Glu Leu His
                    420                 425                 430
        Gln Gly Gly Arg Arg Tyr Met Met Ile Val Asp Pro Ala Ile Ser Ser
                        435                 440                 445
        Ser Gly Pro Ala Gly Ser Tyr Arg Pro Tyr Asp Glu Gly Leu Arg Arg
                    450                 455                 460
        Gly Val Phe Ile Thr Asn Glu Thr Gly Gln Pro Leu Ile Gly Lys Val
        465                 470                 475                 480
        Trp Pro Gly Ser Thr Ala Phe Pro Asp Phe Thr Asn Pro Thr Ala Leu
                            485                 490                 495
```

-continued

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
                515                 520                 525

Ser Glu Asp Gly Cys Pro Asn Asn Glu Leu Glu Asn Pro Pro Tyr Val
                530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
                595                 600                 605

Tyr Ala Gly His Trp Thr Gly Asp Val Trp Ser Ser Trp Glu Gln Leu
                610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
                690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                755                 760                 765

Leu Gly Thr Trp Tyr Asp Leu Gln Thr Val Pro Ile Glu Ala Leu Gly
                770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
                820                 825                 830

Thr Thr Glu Ser Arg Gln Gln Pro Met Ala Leu Ala Val Ala Leu Thr
                835                 840                 845

Lys Gly Gly Glu Ala Arg Gly Glu Leu Phe Trp Asp Asp Gly Glu Ser
                850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
                900                 905                 910

```
Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950
```